(12) United States Patent
Ohyu et al.

(10) Patent No.: US 6,187,032 B1
(45) Date of Patent: Feb. 13, 2001

(54) MEASUREMENT OF INTRACARDIAC ELECTROPHYSIOLOGICAL PHENOMENA

(75) Inventors: Shigeharu Ohyu, Otawara; Izumi Watanabe, Tochigi-ken; Yoichi Takada, Otawara; Yoshihiro Sakuma, Tochigi-ken, all of (JP)

(73) Assignee: Kabushiki Kaisha Toshiba, Kawasaki (JP)

( * ) Notice: Under 35 U.S.C. 154(b), the term of this patent shall be extended for 0 days.

(21) Appl. No.: 09/182,412

(22) Filed: Oct. 30, 1998

(30) Foreign Application Priority Data

Oct. 30, 1997 (JP) .................................................. 9-299111

(51) Int. Cl.[7] ......................................................... A61B 5/05
(52) U.S. Cl. .............................................................. 607/409
(58) Field of Search ..................................... 600/407, 409, 600/411, 413, 416, 425, 428, 437, 443

(56) References Cited

U.S. PATENT DOCUMENTS

| 5,228,443 | * | 7/1993 | Tatar ..................................... | 600/409 |
| 5,285,385 | * | 2/1994 | Igarashi et al. ....................... | 600/409 |
| 5,594,849 | * | 1/1997 | Kuc et al. ............................. | 600/409 |
| 5,601,081 | * | 2/1997 | Tomita et al. ........................ | 600/409 |

FOREIGN PATENT DOCUMENTS 8-289877   11/1996   (JP) .

OTHER PUBLICATIONS

H. Roozen, et al., Med. & Biol. Eng. & Comput., No. 25, pp. 250–260, "Computing the Activation Sequence at the Ventricular Heart Surface from Body Surface Potentials", 1987.

Geertjan Huiskamp, et al., IEEE Transactions on Biomedical Engineering, vol. 35, No. 12, pp. 1047–1058, "The Depolarization Sequence of the Human Heart Surface Computed from Measured Body Surface Potentials", Dec. 1988.

Shigeharu Ohyu, et al., T. IEE Japan, vol. 116–A, No. 8, pp. 698–704, "A Method to Solve the Magnetocardiographic Inverse Problem Based on a Ventricular Excitation Model", 1996.

* cited by examiner

*Primary Examiner*—William E. Kamm
(74) *Attorney, Agent, or Firm*—Oblon, Spivak, McClelland, Maier & Neustadt, P.C.

(57) ABSTRACT

A diagnostic system for intracardiac electrophysiological phenomena is provided. The phenomena are inferred based on at least one of a potential obtained from a patient and a magnetic field obtained from the patient. The system comprises inferbly analyzing element for analyzing the at least one information so as to obtain a characteristic quantity associated with at least one of a magnitude and an interval of a myocardial electroaction amount of the patient; and visualizing element for displaying the characteristic quantity as a distribution image.

72 Claims, 68 Drawing Sheets

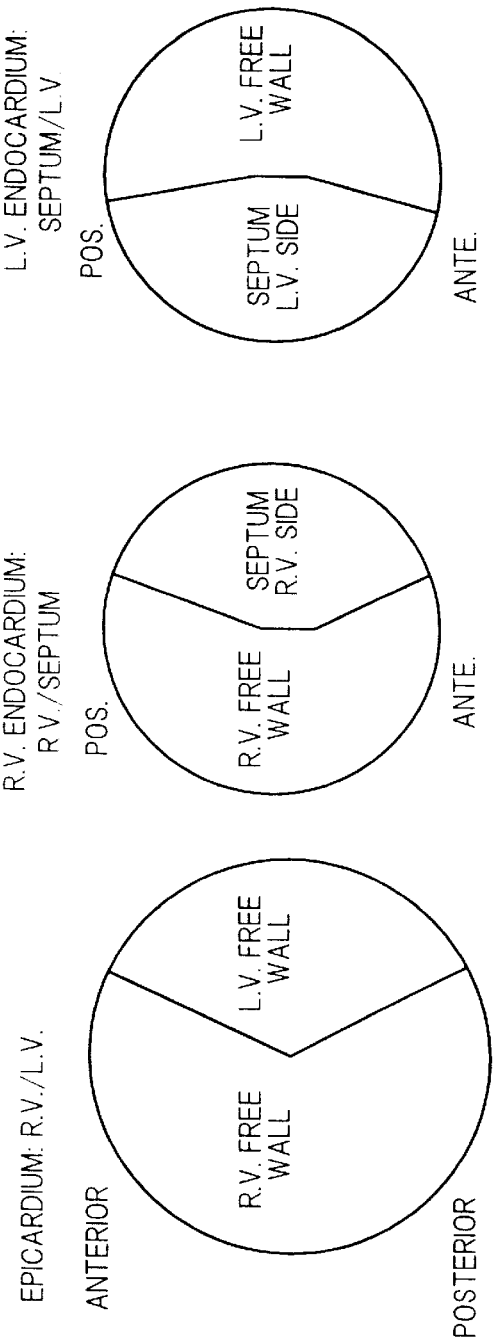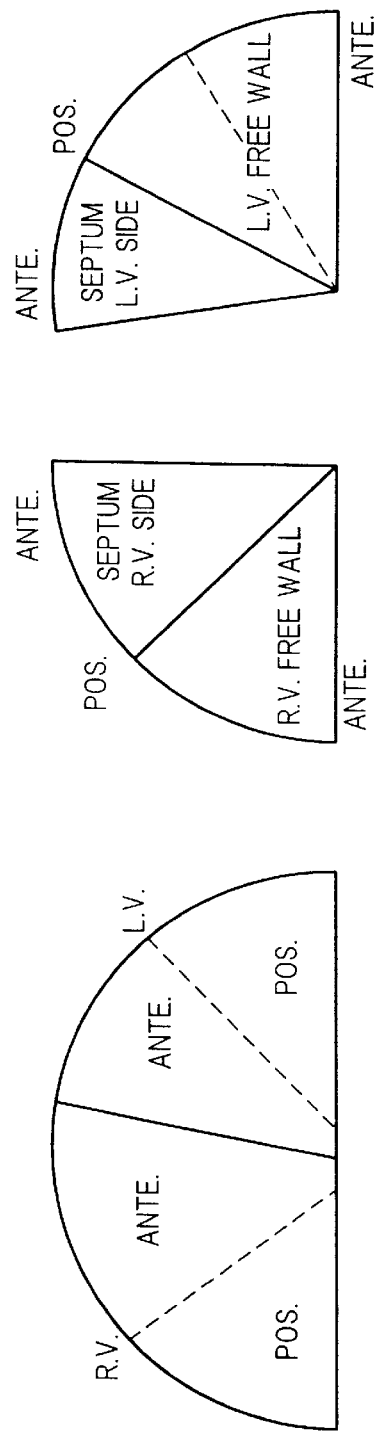

| ACTION POTENTIAL AMPLITUDE[mV] AVERAGE | R.V. FREE WALL | | SEPTUM | | L.V. FREE WALL | |
|---|---|---|---|---|---|---|
| | ANTE. | POS. | ANTE. | POS. | ANTE. | POS. |
| BASE SIDE | 89.6 | 88.2 | 79.6 | 91.3 | 80.6 | 93.1 |
| APEX SIDE | 68.1 | 82.3 | 63.8 | 79.6 | 71.0 | 88.2 |

| ACTION POTENTIAL AMPLITUDE[mV] MAX. | R.V. FREE WALL | | SEPTUM | | L.V. FREE WALL | |
|---|---|---|---|---|---|---|
| | ANTE. | POS. | ANTE. | POS. | ANTE. | POS. |
| BASE SIDE | 91.6 | 89.8 | 88.6 | 93.2 | 88.9 | 94.6 |
| APEX SIDE | 86.2 | 91.2 | 81.2 | 91.3 | 86.3 | 93.1 |

| ACTION POTENTIAL AMPLITUDE[mV] MIN. | R.V. FREE WALL | | SEPTUM | | L.V. FREE WALL | |
|---|---|---|---|---|---|---|
| | ANTE. | POS. | ANTE. | POS. | ANTE. | POS. |
| BASE SIDE | 85.3 | 84.8 | 85.9 | 87.2 | 75.1 | 88.1 |
| APEX SIDE | 43.4 | 74.3 | 32.0 | 65.3 | 55.4 | 84.0 |

FIG. 66

MEASUREMENT OF INTRACARDIAC ELECTROPHYSIOLOGICAL PHENOMENA

BACKGROUND OF THE INVENTION

The present invention relates to a system for measuring electrophysiological phenomena generated in a human heart, and more particularly to providing novel approaches to not only inferably analyze electrophysiological phenomena generated in the heart by detecting potentials and magnetic fluxes generated therefrom but also visualize the analyzed results in consideration of easier interpretation and/or broader applications to cardiac diseases.

One conventional technique for the solution of the electrocardiogram and magnetocardiogram inverse problems is proposed by the inventors in a Japanese patent Laid-open Publication No. 8-289977. In this publication, a diagnostic system provides processing as shown by a flowchart in FIG. 1. The system has a computer in which a heart model is set therein with software, excitation conduction of the heart is efficiently simulated on the model using known methods, and an electrocardiogram or magnetocardiogram is obtained from the simulation results.

For using this approach, data including the shapes, positions, and directions of the ventricles, one or more early excitation positions and excitation time instants thereat, excitation conduction velocities in the ventricles, and conductance distributions in the ventricles are should be given as parameters.

In the above publication, the present inventors also propose a solution method of an inverse problem on the above propagated excitation simulation method. Specifically, some of the parameters (for example, early excitation positions and excitation time instants thereat) given to the ventricle model are corrected such that differences between measured electrocardiograms or magnetocardiograms and simulated electrocardiograms or magnetocardiograms with the above methods are lowered to values as small as possible. The possible lowest values are outputted as inferred results. The remaining parameters other than the parameters selected (for example, parameters for a distribution of propagated excitation velocities and a distribution of action potential amplitudes, except early excitation positions and excitation time instants thereat) are given as appropriate values, and those parameters are treated as fixed values in the inferring calculation.

Another conventional art is concerned with a method of inferring a distribution of excitation onset times on a ventricular surface from QRS complexes in multi-channels electrocardiograms detected the body surface, which is reported by the paper "H. Roozen et al., "Computing the activation sequence at the ventricular heart surface from body surface potentials", Medical & Biological Engineering & Computing, may 1987". In the paper, assumption is made that the conductance in a cardiac muscle is uniform and isotropic and its action potential amplitude is constant, and a volume integral equation (whose integral region is over the entire cardiac muscle) expressing the relationship between a distribution of excitation onset times in the cardiac muscle and QRS complexes guided channel by channel is converted into a boundary integral equation. By solving the equation, the distribution of the excitation onset times on the ventricular surface is analyzed from the measure results of QRS complexes in the electrocardiograms.

however, the forgoing conventional approaches still have various problems which should be overcome.

In the diagnostic system according to the first conventional approach, a magnetocardiogram and parameters to be inferred are in nonlinear relation. To infer the parameters requires calculation to be repeated tremendously many times and a simulation for propagated excitation to be performed every calculation. The simulation needs lots of calculation time. In consequence, a first problem is that time to perform one derivation of the simulation becomes extremely long.

A method of inferring intracardiac electrophysiological phenomena according to the first conventional approach is exemplified in a paper "T.IEE Japan, Vol. 116-A, No. 8, 1996, 698–704", where an early excitation region and its early excitation time are inferred as variables and distributions of both excitation onset times and action potential amplitudes are given as fixed values.

Owing to the fact that the paper treats a distribution of excitation onset times or action potential amplitudes as fixed values, a problem that inferred information does not fit to actual situations may be brought about. For example, if the inferring method according to the first conventional approach is actually applied to patients having myocardial infraction, a delay in propagated excitation will be caused by the infraction portion and an action potential amplitude will be decreased. Moreover, because an initial excitation portion and/or excitation time vary largely depending on individuals, it is difficult to treat as any fixed value an excitation conduction velocity distribution, action potential amplitude distribution, conductance distribution, initial excitation portion, and initial excitation time. In other words, these parameters should be treated as variables.

On one hand, if those parameters are all handled as variables, the number of parameters to be inferred outstandingly increases, the sizes of parameter spaces to be searched become huge, and it is extremely difficult to stably infer quantities. A second problem is that it is almost inadequate to diagnose abnormalities by applying in actual clinical fields the first conventional approach to patients having myocardial infraction or others.

On the other hand, in the case that the inferring method according to the first conventional approach is applied to patients who suffer from cardiac dysrhythmia and others, but not principal diseases such a myocardial infraction, it is considered that an excitation conduction velocity distribution, action potential amplitude distribution, and/or conductance distribution be given as fixed amounts, and only an early excitation region and early excitation time be inferred, as stated in the foregoing paper.

In this case, a steady analysis requires that propagated excitation velocities and action potential amplitudes in the cardiac muscle as well as a conductance distribution in the heart be given in detail. However, because information about those amounts is not known in detail at present, approximated information is compelled to be given. It is therefore difficult to simulate the propagated excitation in higher accuracy. A third problem is that inferred results are largely influenced by ambiguous amounts of propagated excitation velocities, action potential amplitudes, and conductance values, which have been pre-given, resulting in unstable inferred results.

It is actually frequent that patients who suffer from cardiac dysrhythmia have principal diseases, such as myocardial infraction or myocardial ischemia. A fourth problem is that, as long as an inferring system for intracardiac electrophysiological phenomena is used for patients who have only cardiac dysrhythmia, but do not have such principal diseases, applicable patients are extremely limited, thereby lowering versatility in application.

On one hand, the second conventional approach does not need the simulation for propagated excitation to be performed. Hence a problem that a huge amount of time needs for analysis is lightened. But the approach is based on the assumption that an action potential amplitude distribution and a conductance value distribution are uniform. This assumption is requisite when a volume integral equation adopted as a basic equation is converted into a boundary integral equation in this approach. It is therefore not allowed to apply the second conventional approach to patients who suffer from diseases, such as myocardial infraction. A fifth problem is that patients to which diagnosis according to the second conventional approach is applied are limited, lowering versatility, like the first conventional approach.

Moreover, there are some problems concerning a ventricular model and a chest conductance distribution model, which are caused in common from the first and second conventional approaches.

In the first and second conventional approaches, increasing inferred accuracy in an excitation onset time distribution and others needs to use a ventricular model fit to an individual ventricular shape in order to perform accurate analysis. However, the present situation is that the size and position of each patient's heart are measured by hand from his or her MRI image, and a typical ventricular model having a representative shape is made to enlarge or reduce according to the measured values.

it is difficult to automatically detect the heart size. Hence, completely extracting the heart shape from three-dimensional images acquired with MRI or X-CT in an automatic fashion is difficult. Producing a ventricular model fit to each of many patients as a routine work is not practical.

In magnetocardiogram inverse problems, in general, it is pointed out that a chest conductance distribution model fit to the chest shape and conductance distribution of each patient is required to be used in calculating magnetic fields. However, since the conventional approaches use the boundary element method or finite element method as means for taking account of patient's actual conductance distribution, it is required that tissue boundaries between the ventricles and the chest are configured with triangular meshes or the chest region is configured with tetrahedral meshes and other polyhedral meshes. The configuration requires to make the meshes fit to the tissue boundaries. Such fitting processing is difficult to be automatically performed. Thus it is actually difficult to produce the chest conductance distribution model routinely every day for each of many patients.

It is therefore concluded that an inferring method which considers the chest shape and the chest conductance distribution both of which is fit to each patient has not been practiced, lowering accuracy in inferring an excitation onset time distribution. This is a sixth problem posed by the conventional approaches.

On the other hand, for displaying analyzed results by the foregoing various approaches, typical display methods includes methods of displaying a single dipole, displaying a current source distribution, and displaying an excitation onset time distribution.

The method of displaying a single dipole concentrates on a conventional generally-used analysis that approximately assumes a single current dipole existing in the heart as a current or flux source, and on this assumption, infers the position, direction and magnitude of the current dipole. Thus, by this display method, those analyzed results are visualized with symbols such as arrows.

The cardiac muscle is in action, analyzed values of the position, direction and magnitude of a current dipole changes from time to time. Thus analysis during a certain interval produces a locus of the current dipole.

In the display of such locus, a topographic image acquired by clinical imaging modalities, such as MRI systems or X-CT scanners, is used. Generally, symbols such as arrows are placed on inferred positions on such topographic image. FIG. 2 shows one such example, which exemplifies that an inferred position of a single current dipole is in the cardiac septum and temporal loci (times 1 to 4) indicating changes in positions of the inferred current dipole are expressed by arrows.

However, applications that can be approximated by a single current dipole are limited; for example, only current sources activated in an internal corresponding to the early QRS, current sources corresponding to an early interval of ventricular extrasystole, or some other current sources can be approximated. In general, because current sources are spread in the heart, it is difficult to express such spread sources with a single current dipole. The display method relied on a single current dipole is, in fact, limited for use. Although this display is used for limited particular applications, such as inferring accessory conduction paths for WPW syndromes, or early excitation regions in ventricular extrasystole, it is almost difficult to apply this display to other diseases including myocardial infraction and cardiac dysrhythmia.

A method of displaying current source distributions is on trail. On the assumption that electroaction sources in the heart may be approximately expressed by current dipoles distributed therein, this display method is used to display in colors distribution data of inferred current dipoles. According to this approximate inferring, different sets of current dipole distribution data are obtained in a certain ventricular section for different analysis times. FIG. 3 illustrates density images indicating current dipole density distributions at times 1 to 3 in a certain interval. This display fairly improves difficulties encountered in the foregoing single dipole display.

However, the display method with current source distributions visualizes only a given section of the ventricles. When considering a situation that the ventricles should be observed from many directions thereof, different types of plural sections are required to be displayed. If a plurality of such images are produced and displayed, it is probably possible that temporal changes in current dipole distributions can be observed. If doing so, a number of images are required. Even if those images are produced and displayed, an operator is obliged to interpret a number of images displayed in turn. Of course, the interpretation involves bothersome operation such as scrolling images. Scrolling images is apt to lose information interpreted from the former images, having influence on accuracy in interpretation. Scrolling also increases operational work. Further, even when there are a plurality of monitors for interpretation, to observe the monitor screens separately needs plenty of interpretation work, lowering efficiency in interpretation.

This display method with current source distributions also poses a problem that resolution displayed are rather low, being inferior in providing effective diagnosis information.

A further method of displaying distributions of excitation onset times is proposed by, for example, the above-cited paper "T.IEE Japan, Vol. 116-A, No. 8, 1996, 698–704. According to this paper, ventricular excitation onset time distributions are analyzed based on measured magnetocardiogram data, and the distributions are visualized. Another approach for this kind of display is disclosed by "H. Roozen et at,: "Computing the activation sequence at the ventricular heart surface from body surface potentials", Medical &

Biological Engineering & Computing, May, 1987". In this paper, excitation onset time distrubitons of the ventricular surface are inferred from QRS waveforms in electrocardiogram acquired from the body surface, and inferred results are displayed.

However, in these display methods, the analysis and display are restricted to the myocardial excitation conduction process. In case where lesions in excitation conduction, which includes bundle branch block, WPW syndrome, and ventricular extrasystole, with no action potential lowered, the displayed images are still useful. To the contrary, where diseases that involves large decreases in the action potential amplitude compared with troubles in excitation conduction, as seen from myocardial infraction or myocardial ishemia, it is difficult to distinguish diseases in the displayed images. Application for these display methods is also restricted.

SUMMARY OF THE INVENTION

Therefore, a first object of the present invention is to infer or estimate an intracardiac conduction process of excitation (excitation onset times, action potential amplitudes, and other of the cardiac muscle) in a faster, more stable, and more accurate manner than the conventional approaches, without previously requiring detailed information about a distribution of intracardiac conduction velocities of excitation.

A second object of the present invention is to not only infer or estimate an intracardiac conduction process of excitation in a faster, more stable, and more accurate manner than the conventional approaches, without previously requiring detailed information about a distribution of intracardiac conduction velocities excitation, but also provide versatility for an inferring or estimating system by making it applicable to even patients who suffer from diseases, such as myocardial infraction.

A third object of the present invention is to automatically obtain the ventricular shape and the chest conductance distribution patient by patient, and to increase practicality by enabling an easier diagnosis for many patients.

A fourth object of the present invention is to provide visualized images that is able to permit interpreters to quickly and accurately distinguish a variety of diseases in the images with less work, including, not limited to those simply accompanying troubles in excitation conduction, diseases with less action potential amplitudes such as cardiac dysrhythmia, myocardial infraction, or myocardial ischemia.

In the present invention, intracardiac electrophysiological phenomena are understood as an intracardiac excitation conduction process as well as a myocardial electroaction amount. Typically, the excitation conduction process is expressed by excitation onset times or excitation conduction velocities. On one hand, the myocardial electroaction quantity is a representative indicative of amounts including an action potential amplitude in changes in an action potential of the cardiac muscle, a conductance distribution of the cardiac muscle, an absolute of a current dipole density made by multiplication of both the amplitude and the distribution, and various other quantities relevant to those. The myocardial electroaction amount represents various magnitudes relevant to an electroaction at each point on the cardiac muscle, and is not referred to as only an instantaneous amplitude of action potentials.

In order to realize the above objects, there is provided a diagnostic system for intracardiac electrophysiological phenomena, in which the phenomena are inferred based on at least one of a potential obtained from a patient having a heart and a magnetic field obtained from the patient: inferably analyzing means for analyzing the at least one information so as to obtain a characteristic quantity associated with at least one of a magnitude and an interval of an electroaction in a cardiac muscle of the patient; and visualizing means for displaying the characteristic quantity as a distribution image.

It is preferred that the analyzing means are composed of means for analyzing not only the at least one information so as to obtain the characteristic quantity but also a further characteristic quantity associated with at temporal sequence of excitation of the cardiac muscle, and the visualizing means is composed of means for displaying not only the characteristic quantity as the distribution image but also the further characteristic quantity as a further distribution image.

It is also preferred the characteristic quantity is first information about a distribution of myocardial electroaction consisting of at least one of an action potential amplitude distribution on the cardiac muscle, a conductance distribution of the cardiac muscle, and a current dipole density of the cardiac muscle, and the further characteristic quantity is second information about a propagated excitation process consisting of at least one of an excitation onset time distribution on the cardiac muscle, an excitation conduction velocity distribution on the cardiac muscle, and a divergence distribution of excitation onset times of the cardiac muscle.

Preferably, the visualizing means has a visualizing apparatus having a visualizing area and means for representing both the first information and second information on the visualizing area of the visualizing apparatus. For example, the visualizing apparatus is one of an electric monitor, a printing apparatus, and an imaging apparatus with a film. For example, the representing means is means that represents separately both the first information and the second on the visualizing area of the visualizing apparatus.

It is preferred that, in the above basic configuration, further comprising measuring means for measuring the magnetic field from a measuring point on a body surface of the patient, wherein the analyzing means comprising expressing means for expressing with a plurality of parameters information about the electrophysiological phenomena including the characteristic quantity, calculating means for calculating a temporal waveform of the magnetic field at each measuring point on the basis of the electrophysiological phenomena expressed with the plurality of parameters, and inferring means for inferably determining each value of the plurality of parameters by searching different values assigned to the plurality of parameters such that a difference between the calculated temporal waveform and information about the measure magnetic field is made small.

It is preferred that the measuring means is multi-channel type SQUID flux meter measuring the magnetic field.

It is also preferred that the electrophysiological phenomena includes not only the characteristic quantity but also a further characteristic quantity associated with a temporal sequence of excitation of the cardiac muscle, and visualizing means is composed of means for displaying not only the characteristic quantity as the distribution image but also the further characteristic quantity as a further distribution image.

For example, the further characteristic quantity associated with the temporal sequence of excitation of the cardiac muscle is an excitation onset time as part of a propagated excitation process of the cardiac muscle. For example, the analyzing means further comprising model setting means for setting a heart model from image information of the patient.

It is preferred that the expressing means consist of means for expressing both a first distribution of the excitation onset time and a second distribution of an amount of the myocardial electroaction with the parameters in number less than representative points of the heart model, and the analyzing means comprises means for computing the first and second distributions using the less parameters.

BRIEF DESCRIPTION OF THE DRAWINGS

In the accompanying drawings:

FIGS. 41A to 41F pictorially show a variety of types of developed views prepared;

FIG. 66 is a table displayed in a nineteenth embodiment of the present invention, wherein representative values of analyzed results are listed as figures;

DETAILED DESCRIPTION OF THE PREFERRED EMBODIMENTS

Referring to FIGS. 4 to 10, a first embodiment of the present invention will be described.

Figure 1:
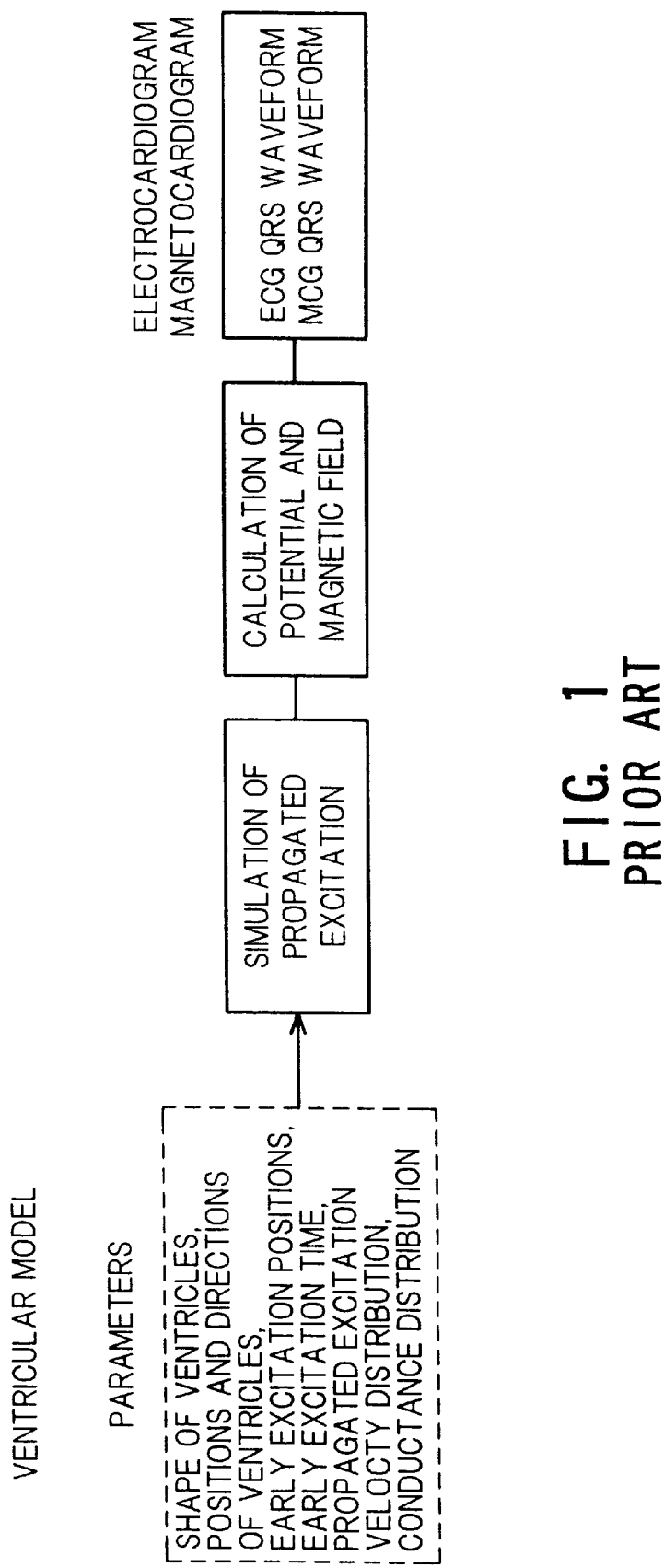
FIG. 1 functionally shows procedures for one example of the conventional analysis.
Figure 2:
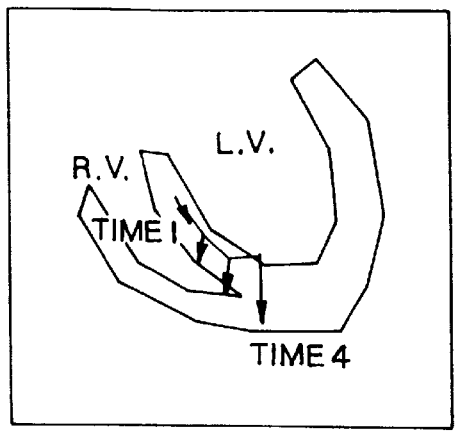
FIG. 2 shows one example of conventional displayed images.
Figure 3:
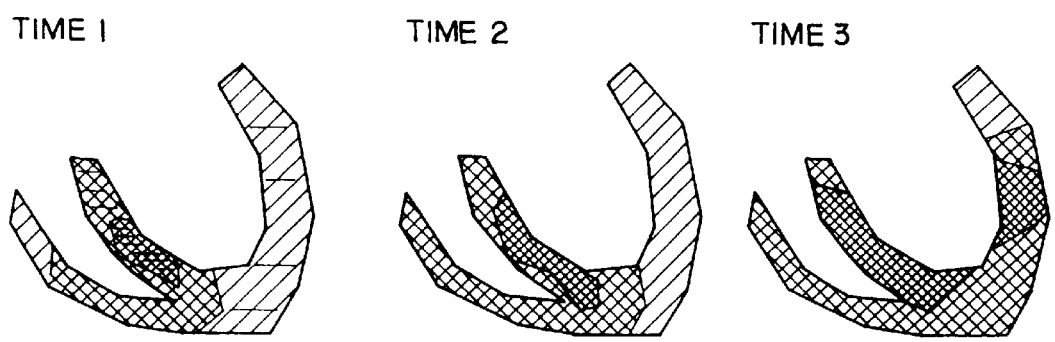
FIG. 3 shows another example of conventional displayed images.
Figure 4:
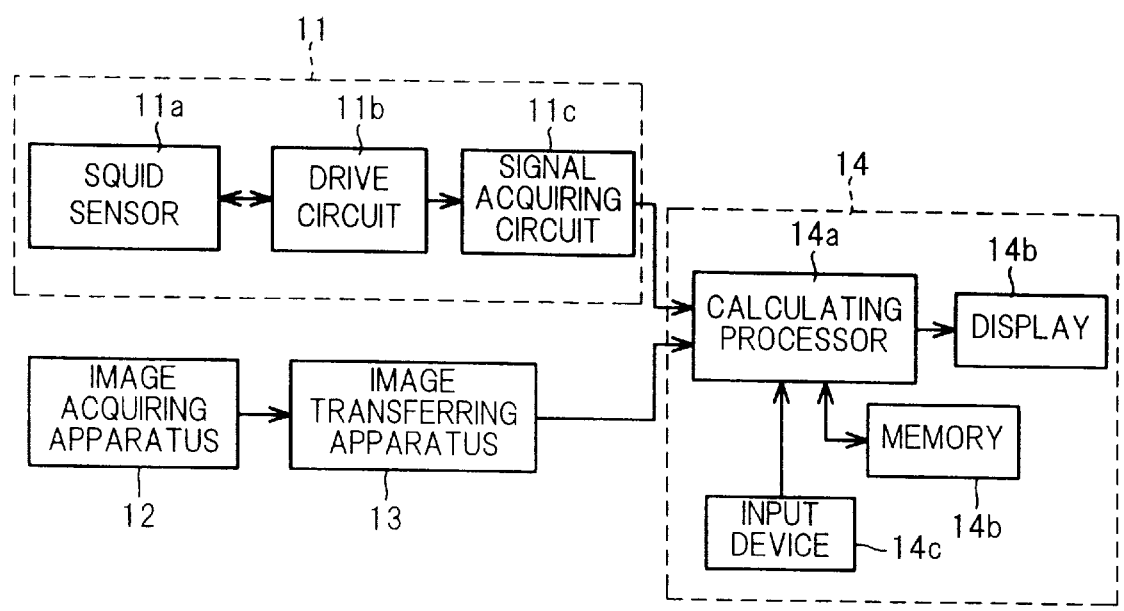
FIG. 4 is a schematic block diagram of a diagnostic system for intracardiac electrophysiological phenomena of a first to fourth embodiments of the present invention.
Figure 5:
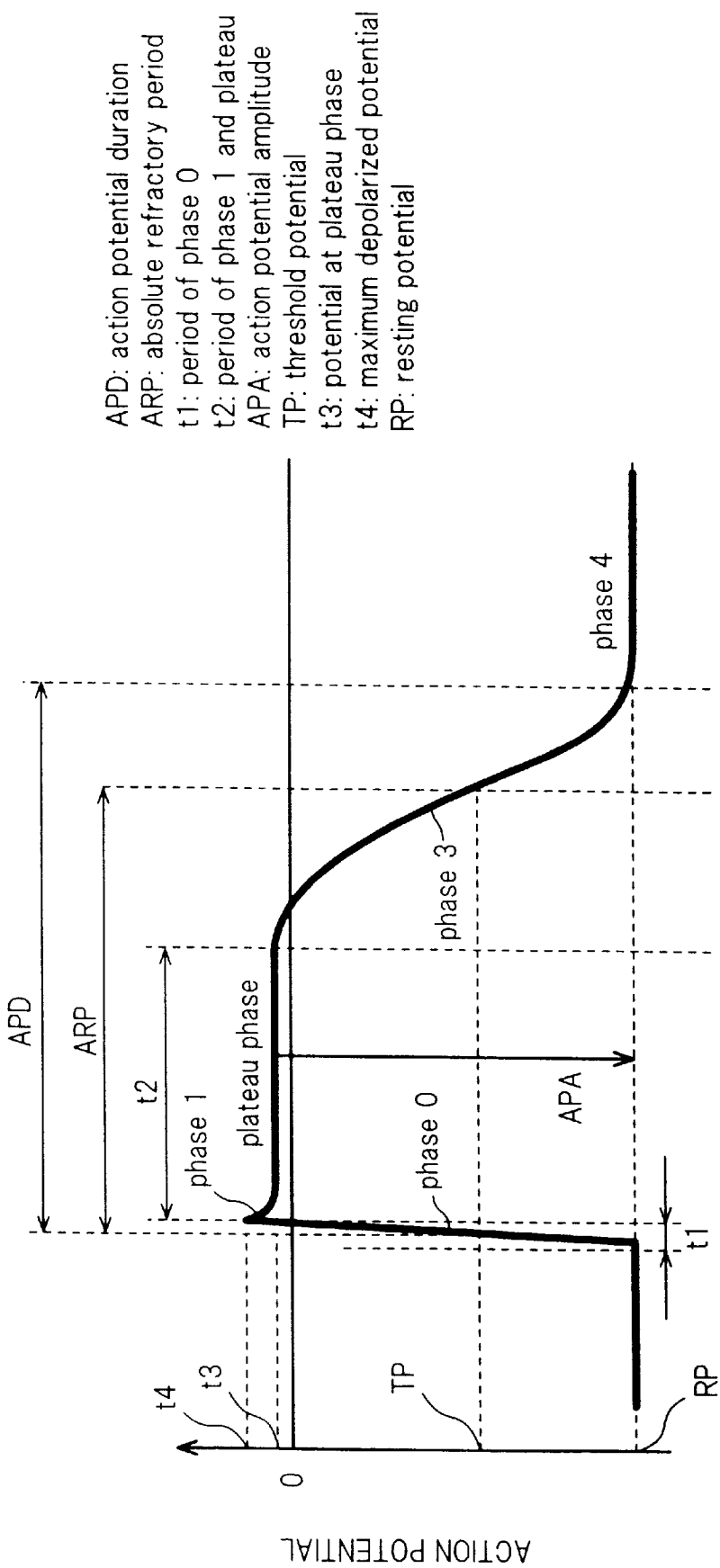
FIG. 5 pictorially shows the cross section of the heart.
Figure 6:
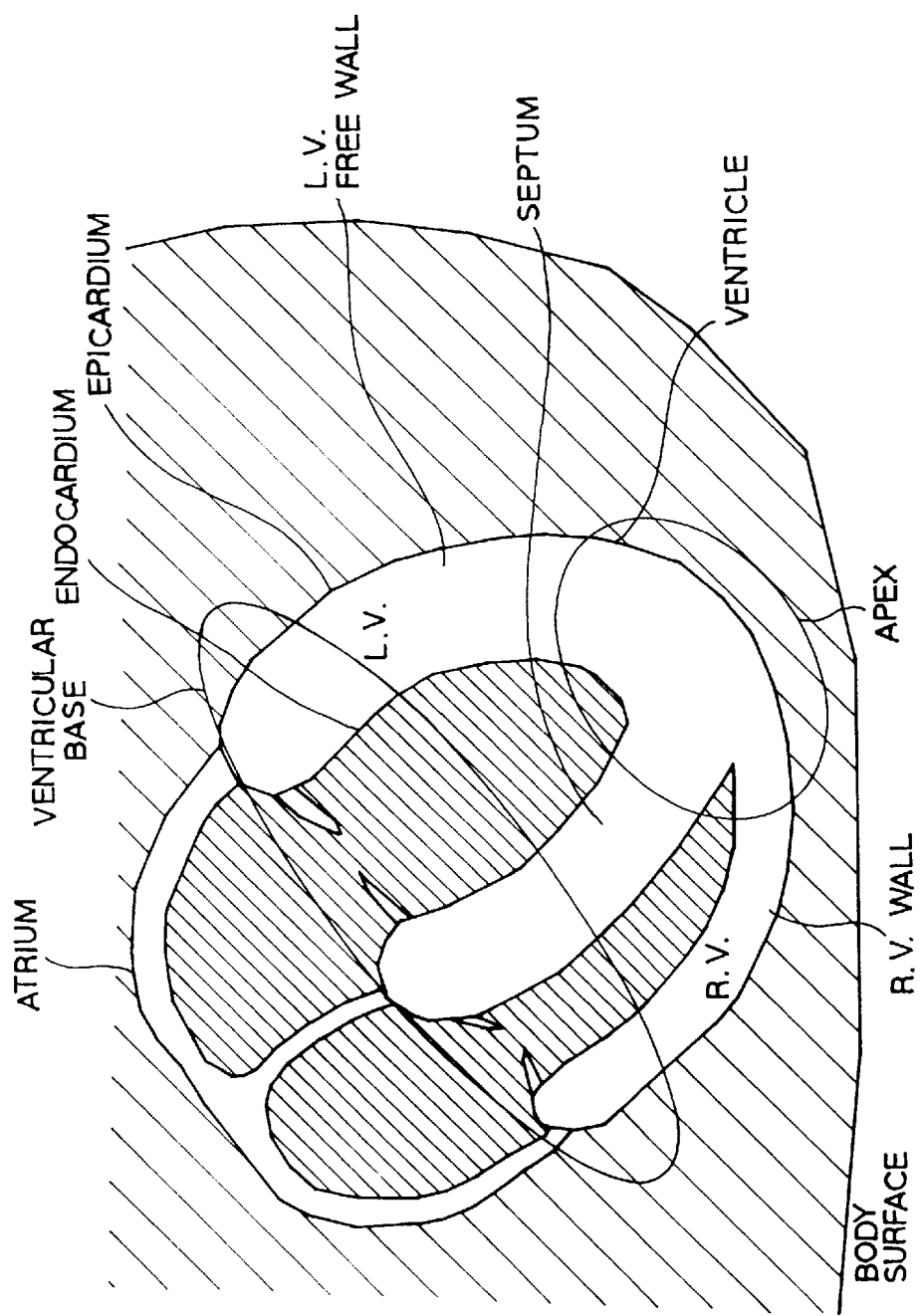
FIG. 6 illustrates one example of temporal waves of action potentials.

FIG. 4 schematically shows the configuration of a diagnostic system for intracardiac electrophysiological phenomena according to the embodiment. The system concentrates on diagnosis of the heart of patients as objects to be examined. Thus, prior to the detailed description, as references, a cross sectional configuration of the human heart is illustrated in FIG. 5, and a temporal wave of an action potential is exemplified in FIG. 6, which is one characteristic quantity of myocardial electroaction amounts of the human heart.

The diagnostic system comprises a SQUID (Superconducting QUantum Interference Device) flux meter 11, image acquiring apparatus 12, imaging transferring apparatus 13, and computer system 14.

The SQUID flux meter 11 comprises a SQUID sensor 11a, drive circuit 11b, and signal acquiring circuit 11c, which compose a multi-channel SQUID flux meter acting as a high-sensitive magnetic sensor. In the SQUID flux meter 11, the SQUID sensor 11a is used to detect flux waveforms of the heart at a plurality (a few) measuring points set on the chest surface of a patient, the waveform signals are amplified/filtering-processed, converted into corresponding digital data by an A/D converter. The digital-amount flux waveform data are thus sent to the computer system 14.

The image acquiring apparatus 12 is composed of one or more of clinical imaging modalities including, for example, an MRI (magnetic resonance imaging) apparatus, X-ray CT scanner and diagnostic ultrasound apparatus, which can acquire three-dimensional image data. By this apparatus 12, image data (unprocessed image data) are acquired from a patient and sent to the image transferring apparatus 13. The apparatus 13 is provided with a CPU and a memory, for example, where image data received are temporarily stored and provide them for the computer system 14 responsively to a command therefrom. It is preferred that the image transferring apparatus 13 provides the computer system 14 image data via a network or recording medium, and/or, if necessary, performs the conversion of image formats and/or the reconstruction of three-dimensional image data.

Figure 7:
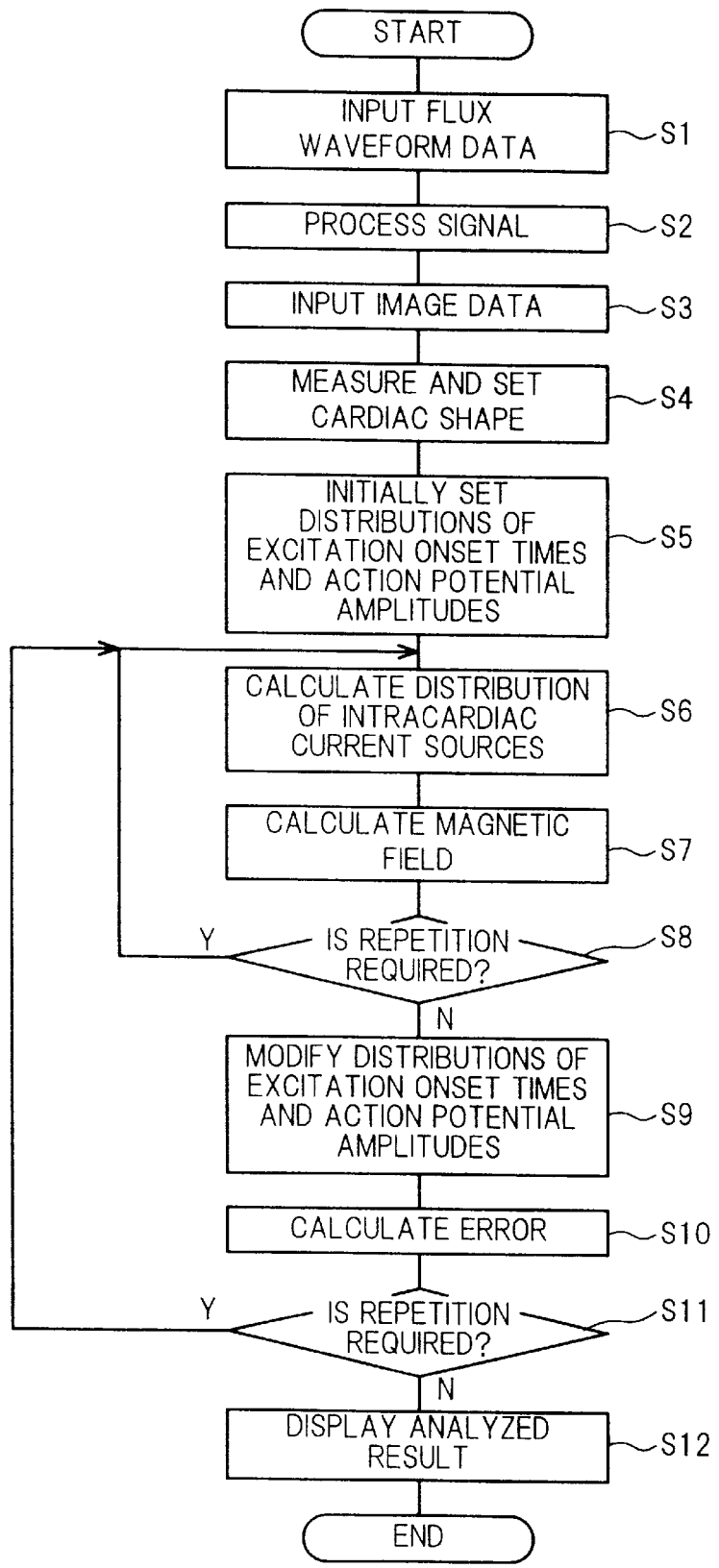
FIG. 7 is a flow chart showing inferring analysis of distributions of excitation onset times and action potential amplitudes, which is processed in the first embodiment.

The computer system 14 takes analysis and calculation required to infer intracardiac propagated excitation processes, and it has a calculating processor 14a whose main part is a CPU incorporated, memory 14b, input device 14c, and display 14d. Program data for the analysis and calculation are preset in the memory 14b. The calculating processor 14a performs the program, and its one example is shown in FIG. 7.

The processing illustrated in FIG. 7 will be described. First, the calculating processor 14a receives flux waveform data supplied by the SQUID flux meter 11 (Step S1), and perform signal processing with the waveform data (Step S2).

The signal processing includes digital filtering for noise reduction and averaging for each heart beat. And times corresponding to QRS complexes in a magnetocardiogram are detected, and magnetic field waveforms corresponding to the QRS complexes are detected channel by channel. A reference time instant can be set arbitrarily; for example, a time instant indicative of the start position or the maximum amplitude of a QRS complex is set to zero, as the reference.

Then the calculating processor 14a receives a plurality of frames of tomographic image data (three-dimensional image data) from the image transferring apparatus 13 (Step S3), and measure and sets the shape of a heart base on the received image data (Step S4). As a result, the region of a cardiac muscle is detected from the three-dimensional image data acquired from, for example, an MRI apparatus, and a ventricular shape model is produced.

Figure 8A:
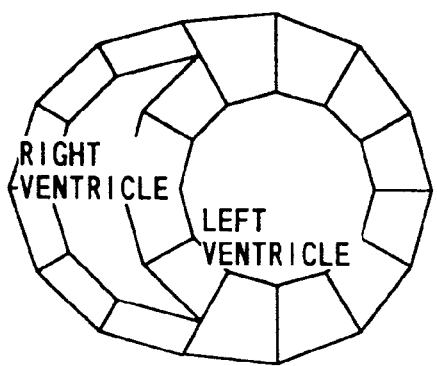
FIGS. 8A and 8B exemplify a ventricular model (i.e., ventricular shape)
Figure 8B:
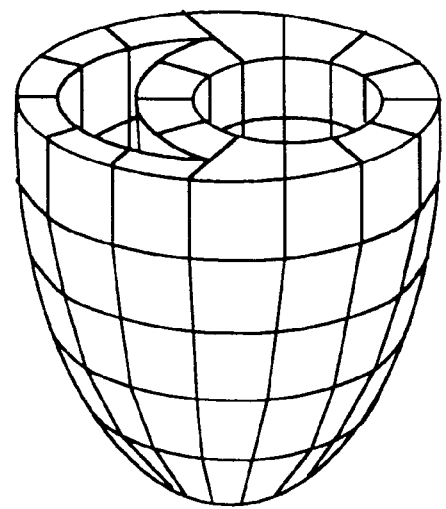
Figures 9A, 9B, 9C, 9D:
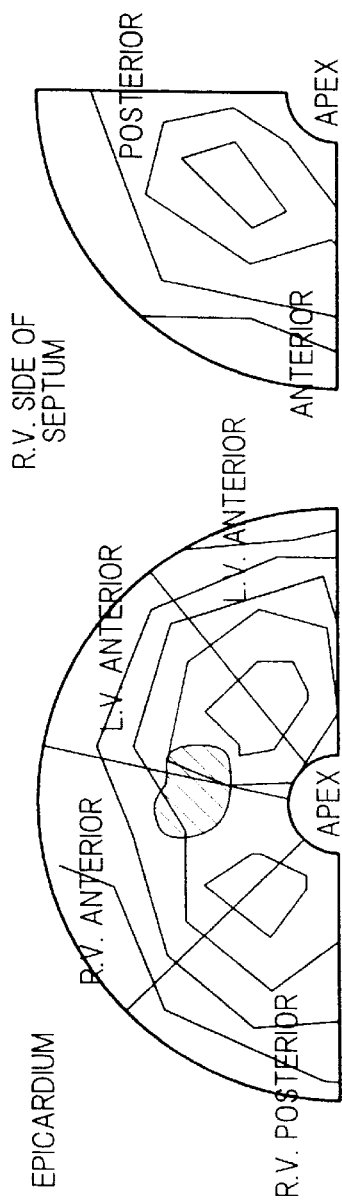
FIGS. 9A to 9D are displayed images of the distributions excitation onset times and action potential amplitudes.

FIGS. 8A and 8B show a basic ventricular model thus-produced, where a number of hexahedral elements (units) are combined to form the model shape. For the ventricular model handled herein, parameters assigned to such dimensions as the length in its major axis direction, the outer radii of the left ventricle in minor axis directions, the wall thickness of the left ventricle, the wall thickness of the right ventricle, the length between the septum and the right ventricle wall can be modified through the input device 14 by operation performed depending on individual patients. As in the major-axis direction, parameters other than the length therein can be specified associated with the apex portion, cardiac base potion, and any levels therebetween.

Processing to fit the ventricular model to a ventricular shape of each patient is performed with either one of an interactive manner by hand or a non-liner optimization manner carried out automatically. In either manner, parameters for altering the ventricular model and parameters for expressing a position and a direction of the ventricular model within a patient are changed such that the ventricle surface exists in a three-dimensional image acquired by clinical imaging modalities and the surface of a ventricular model to be produced agree with each other as possible as it could be.

In the case that the interactive specification by hand is used in the above fitting, one preferable embodiment is that a projection image to which the three-dimensional image is projected along any direction or a cross sectional image of the three-dimensional image sectioned at an arbitrary position and the shape of the ventricular model are displayed on the display 14d at a time, and the parameters are modified by an operator, as viewing a displayed screen of the display. Additionally, the position, direction and shape of a ventricular model are changed according to the modified parameters, during which time the changed images thereof are displayed on the display 14d in an almost simultaneous response manner.

For the automatic fitting using the non-linear optimization method, one preferred example is to make the display 14d into a configuration which is capable of display thereon the position, direction, and shape of a ventricle under fitting an/or its final position, direction, and shape which have been fitted, together with the ventricle shape according to the three-dimensional image. Another preferred configuration is that the shape of a ventricle is changed by hand if necessary, and the resultant shape is set to an initial one which is followed by automatic fitting restarted.

Based on the set cardiac shape model data and the inputted magnetocardiogram data for a QRS interval of a patient, the calculating processor 14a analyzes distributions of both excitation onset times and action potential amplitudes, which are inferred values of a propagated excitation process in the ventricles of the heart (Steps S5 to S7).

An algorithms to be used for analyzing the distributions of both excitation onset times and action potential amplitudes, various non-linear optimization algorithms can be used. Such includes a quasi-Newton method, conjugate gradient method, conjugate direction method, simulated annealing method, genetic algorithm method, and other. Of these typical algorithms includes initial setting of distributions of both excitation onset times and action potential amplitudes (FIG. 7, Step S5), calculating a distribution of intracardiac current sources (FIG. 7, Step S6), calculating magnetic fields (FIG. 7, Step S7), calculating errors (FIG. 7, Step S10), and modifying distributions of both excitation onset times and action potential amplitudes (FIG. 7 Step S9). How these steps are processed on which sequence depends on an employed non-liner algorithm, and is well known. FIG. 7 exemplifies a sequence of processing among the above steps, which are applied to lots of typical algorithms.

The processing of the steps S5 to S10 will be described.

At the above initial setting of Step S5, excitation onset times for the ventricular endocardium and epicardium are initially set and action potential amplitudes are initially set.

In the initial setting for the excitation onset times of the ventricular endocardium and epicardium, initial times are given all the vertexes on the endocardium or epicardium of a ventricle model shown in FIGS. 8A and 8B. The initial times can be selected at random form a predetermined range of, for example, 0 to 80 ms set with a QRS start time employed as a reference. Alternatively, typical excitation start times of a clinically normal heart can be specified as the initial times.

Likewise, in the initial setting for action potential amplitudes, initial amplitudes are given all the vertexes on the endocardium or epicardium of a ventricle model. The initial amplitudes may be at random. Alternatively, where the action potential amplitude is adopted as a representative of myocardial electroaction amounts, appr. −90 mV, known as a clinically normal action potential amplitude, may be given all the vortexes. Moreover, in the ventricle model in FIGS. 8A and 8B, representative points may be allocated on surfaces other than the ventricular endocardium or epicardium, initial values concerning the excitation onset time and the action potential amplitude may be given all the representative points made up of both the vortexes and the additional representative points.

In the calculation of the distribution of intracardiac current sources carried out at Step S6, excitation onset times and action potential amplitudes within the inside of each hexahedron making up the heart model are interpolated. In addition, using the interpolated times and amplitudes, shapes of excitation fronts at some time instants in the QRS interval, and current source distributions on the excitation fronts are calculated. As the interpolation method, a finite element method is frequently used. For example, an interpolation polynomial expressed by the following equation may be used. This interpolation method is also applied to the action potential amplitudes, not limited to the excitation onset times.

$$t = a_1 + a_2 x + a_3 y + a_4 z + a_5 xy + a_6 yz + a_7 zx + a_8 xyz \tag{1}$$

In this equation, t is an excitation onset time at a point in the hexahedron, c is a constant, $a_1$ to $a_8$ are coefficients, and x, y, z are positional coordinates. Based on the equation (1), $a_1$ to $a_8$ are calculated by simultaneously combing eight equations to which coordinates of the eight vertexes of a hexahedron and excitation onset times are provided. Using the equation (1), an excitation onset time at an arbitrary point is obtained. A dipole moment J within the hexahedron is calculated by the following equation:

$$J = \int_{Q_e} \sigma \Phi \frac{\nabla t}{|\nabla t|} \delta(t - t_1) d\Omega_e, \quad (2)$$

where $\sigma$ is a conductance tensor, $\Phi$ is an action potential amplitude, $\delta(X)$ is a function producing 0 and $\delta(0)=\infty$ if $x \neq 0$ and accomplishing $\int \delta(X)dx=1$. $\Omega_o$ is the region of a hexahedron to be objected. A current dipole within a hexahedron is assumed to be positioned at the center-of-gravity thereof.

In the magnetic field calculation at Step S7, based on the positions, directions and magnitudes of a large number of current dipoles calculated, magnetic fluxes which should be measured by the SQUID sensors placed on the chest surface are calculated at each time instant during the QRS interval. This calculation may be carried out with the Biot-Savart law on the assumption that a distribution of conductance values of the body is an infinite, uniform medium or semi-infinite flat plate, or with the sarvas's equation on the assumption that a distribution of conductance values of the body is mapped in the state of a concentric-spherically conductance sphere. Alternatively, using the boundary element method or finite element method, this calculation can be performed with taking account of actual shapes of the cardiac muscle, blood, lungs, fat layer, skin and others.

The foregoing steps S6 and S7 are repeated by required times (Step S8).

Furthermore, in the modification processing of the distributions of both excitation onset times and action potential amplitudes at Step S9, the distributions of both excitation onset times and the distribution of action potential amplitudes set on the heart model is finally modified, based on the values repeatedly calculated at Step S8, such that differences between the magnetocardiogram measured at Steps S1 and S2 and that calculated at Step S7 becomes a smallest value. A practical way of the modification depends a non-linear optimization algorithm adopted.

In the error calculation at Step S10, an error e is calculated that shows how much difference exists between the magnetocardiogram for the QRS interval calculated at Step S7 and the magnetocardiogram for the QRS interval obtained via processing at Steps S1 and S2. For example, when assuming that a magnetocardiogram measured for channel i at j-th time instant of $B_{ij}$ and a magnetocardiogram calculated is $C_{ij}$, an error $\bar{e}$ is obtained by the following equation:

$$e = \sum_{i,j} (B_{ij}/b - C_{ij}/c)^2, \quad (3)$$

where b is a root-mean-square $B_{ij}$ and c is a root-mean-square of $C_{ij}$.

In analyzing the distributions of both excitation onset times and action potential amplitudes, the foregoing steps S6 to S10 are repeatedly executed by desired times required by an adopted non-linear optimization algorithm (Step S11). Thus the distributions of both excitation onset times and action potential amplitudes within the ventricles are obtained.

Data of the distributions thus-obtained are then displayed on the display 14d (Step S12).

FIGS. 9A to 9D show such displayed examples, where isochrone charts of excitation onset times are visualized on developed views of the endocardium and the epicardium. The isochrone chart is formed by mutually connecting with lines points at which the excitation begins at the same time instant. As shown, the distribution of action potential amplitudes are superposedly displayed thereon, utilizing densities in a hue or differences in hues.

Although the displayed examples are formed by developed views made by cutting the ventricles along the major axis, it is also possible that an isochrone chart and/or an action potential amplitude distribution are placed on a circular developed view made by developing each of the epicardium, left ventricular endocardium, and right ventricular endocardium in a circular from. An excitation onset time distribution and/or an action potential amplitude distribution may be superposed on a ventricular sectional view or a perspective projected view of a heart model, or may be visualized separately. Figures indicating those times and/or amplitudes can be added to the views.

Figure 10:
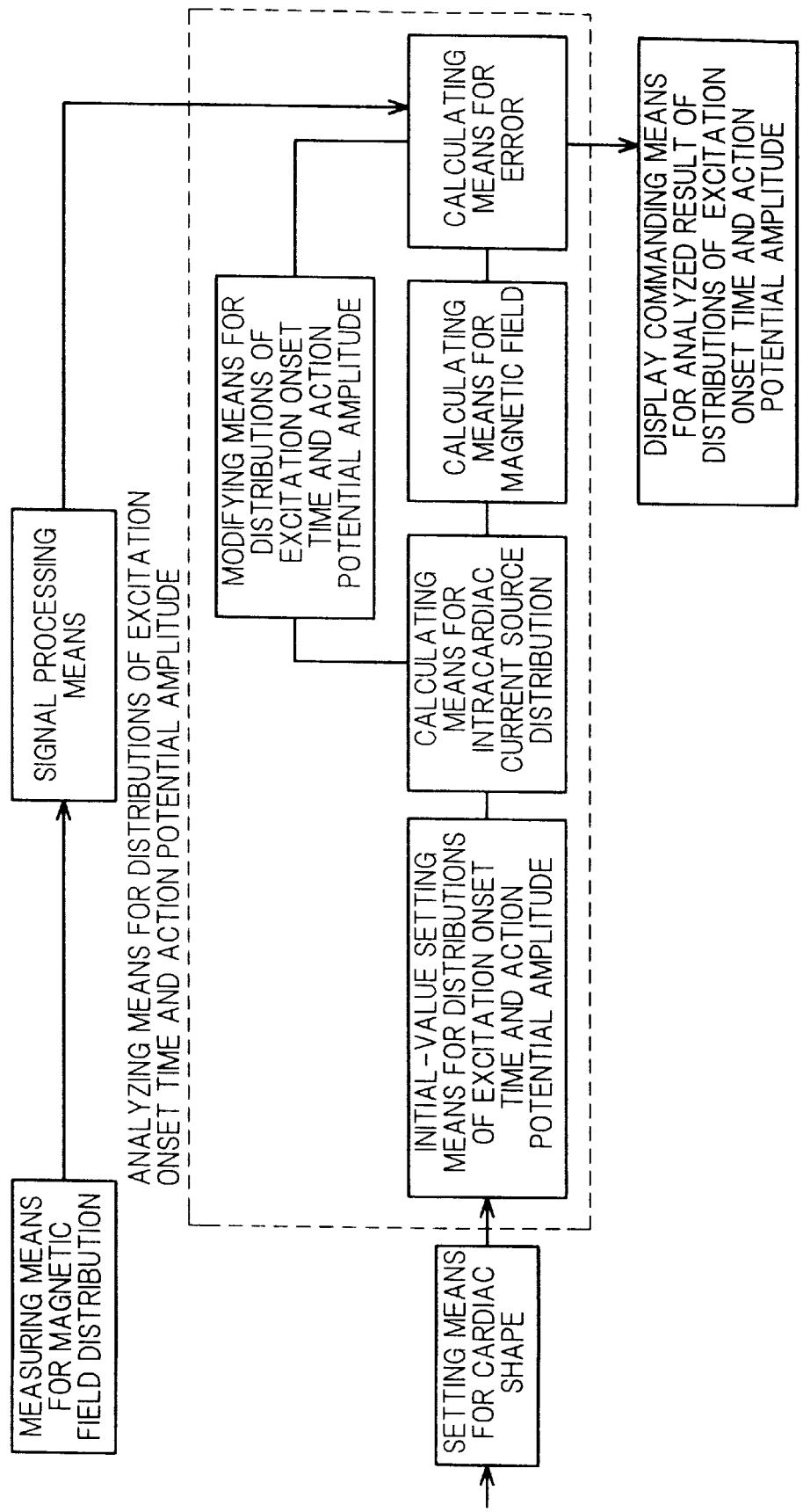
FIG. 10 shows a functional inferring analysis shown in processing in FIG. 6.

In the first embodiment, Steps S1 and S2 constitute signal processing means, Steps S3 and S4 constitute heart shape setting means, Step S5 constitutes an initial value setting means, Steps S6, S8 and S11 constitute current source distribution calculating means, Steps S7, S8 and S11 constitute magnetic field calculating means, Steps S9 and S11 constitute modification means, Steps S10 and S11 constitute error calculating means, and Step 12 constitutes display commanding means (refer to FIG. 10).

According to the first embodiment, both the excitation onset time distribution and the action potential amplitude distribution can be inferred at a time. Ventricular electroactions can be approximately expressed by the both the excitation onset time distribution and the action potential amplitude distribution, even for any normal or abnormal ventricle whose heart beat rate is less than a certain rate. For instance, it can be expressed that portions where myocardial infraction or myocardial ischemia are slower in excitation propagation and smaller in action potential amplitude than a normal portion. Also cardiac dysrthythmia such as tachycardia can be expressed by an excitation onset time distribution that differs from its normal one, provided the number of heart beats is not extremely less, like ventricular fibrillation. In consequence, the diagnostic system for intracardiac electrophysiological phenomena according to the present embodiment can favorably be applied to patients suffering from such various diseases as myocardial infraction and cardiac dysrhythmia, providing a higher versatility in actual clinical fields.

Another advantage is that a process involving a great deal of calculation time is not included in the repeated processing, unlike the conventional analysis. Among the steps included in the repeated processing, a step that requires the most greatest amount of calculation is the magnetic field calculation. But it consists of linear calculation including frequent repetitions of arithmetical operation. Hence employing vector calculation, parallel calculation, pipeline processing, and/or cache memory techniques enable existing computers to perform such calculation at faster speeds. Therefore, compared with the conventional analysis methods, time required for analysis can be reduced greatly.

Still another advantage is to have stability in inferred results. Differently from the conventional ones, the above embodiment configuration does not previously need detailed information about propagated excitation velocities within the ventricles during inferring calculation. Thus instability in inferred results caused by using inaccurate distributions of propagated excitation velocities.

Second Embodiment

Figure 11A:
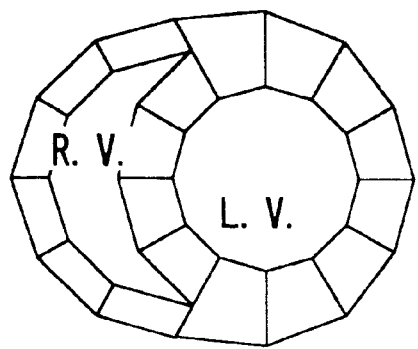
FIGS. 11A and 11B exemplify a ventricular model (i.e., ventricular shape) in the second embodiment of the present invention.
Figure 11B:
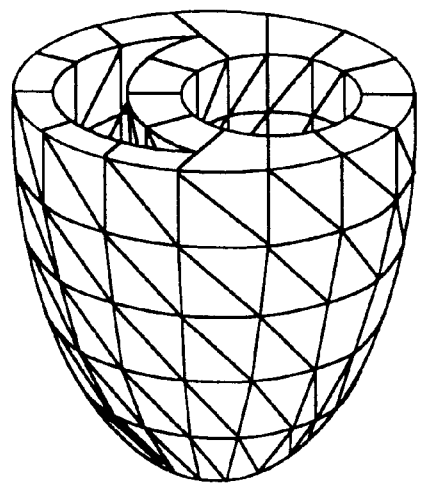

Referring to FIGS. 11A and 11B, a second embodiment will be described. A diagnostic system for intracardiac electrophysiological phenomena of the embodiment are the same in hardware configuration as that described in the above first embodiment.

The second embodiment relates to anther display method of the cardiac shape.

A ventricular model used in this embodiment is shown in FIGS. 11A and 11B. Compared with the first embodiment shown in FIGS. 8A and 8B, a difference lies in that while the model in FIGS. 8A and 8B uses hexahedrons to form a ventricular shape, that in FIGS. 11A and 11B uses pentahedrons (the shapes of triangular prisms) to form that.

The comparison between them will be described below. In the first embodiment, the cardiac model is formed by dividing with hexahedrons, thus the sizes of hexahedrons in the cardiac base portion become less than those in the apex. If calculation amounts for magnetic fields are the same, using different-size hexahedrons is inferior in calculation accuracy to using uniform-size hexahedrons. In the second embodiment, this point is also improved. Using pentahedrons allows the entire cardiac model to be divided equally. As a result, even when the same amount of calculation is done for obtaining magnetic fields, a higher calculation accuracy is maintained.

In detail, at Steps S3 and S4 in FIG. 7, a ventricular model with pentahedrons is employed, and its model is set in agreement with the hart shape of each patient. Using the set ventricular model, a distribution of current sources is calculated at Step S6 in FIG. 7, like the first embodiment.

Therefore, thanks to using pentahedrons, accuracy in the calculation of magnetic fields in this embodiment is increased, provided amounts of calculation are the same in both the embodiments. After all, this advantage leads to a higher accuracy in inferably analyzing current sources.

Although the foregoing first and second embodiments have used hexahedrons and pentahedrons to express the ventricular model, other polyhedrons such as tetrahedrons may be used. Software is configured to set a ventricular shape with such polyhedrons at Step S4 in FIG. 7. Alternatively, a plurality of types of polyhedrons may properly be combined to set a ventricular shape.

Third Embodiment

Figure 12:
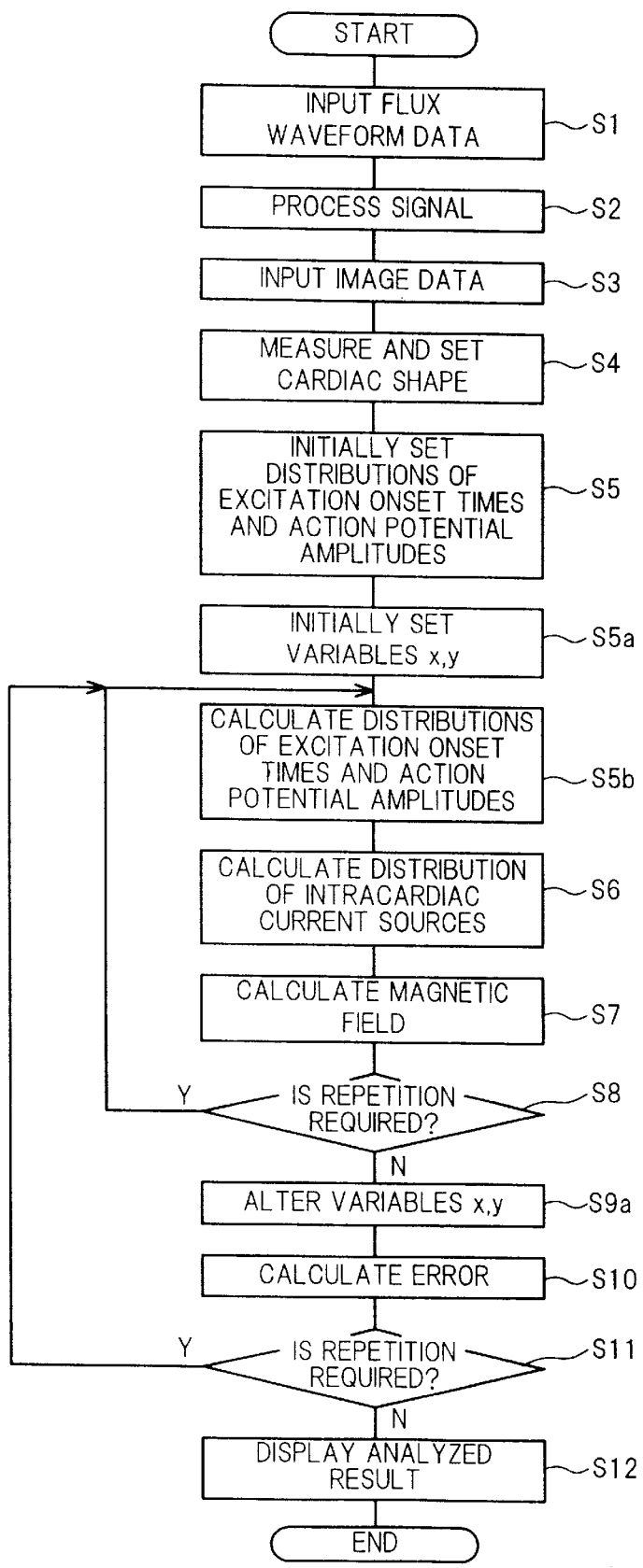
FIG. 12 is a flowchart showing inferring analysis of distributions of excitation onset times and action potential amplitudes, which is processed in the third embodiment.

Referring to FIG. 12, a third embodiment of the present invention will now be described.

A feature of the third embodiment is to express distributions of excitation onset times and/or action potential amplitudes with less parameters in the number than the foregoing embodiments in which values at all the vertexes on the endocardium and the epicardium are used. In the following explanation, a distribution of excitation onset times is exemplified, but that of action potential amplitudes can be processed in the same way, although it will not be explained.

When a vector where excitation onset times at N-piece vertexes on the endocardium and epicardium are arranged longitudinally is noted as t and a covariance matrix for the vector t is noted as S, $$S = \langle tt_T \rangle \quad (4)$$

is established.

When a matrix constructing a column of characteristic vectors is P, and its characteristic values are $\gamma_1 \ldots \gamma_N$, the matrix S is expressed by $$S = P\,diag(\lambda_1 \ldots \lambda_N)P^T \quad (5)$$
$$= (P_1 \ P_2)\,diag(\lambda_1 \ldots \lambda_M, \lambda_{M+1} \ldots \lambda_N)(P_1 \ P_2)^T$$

where $P_1$ and $P_2$ are partial matrices of the matrix P, and $P_1$ is N×M and $P_2$ is N×(N−M). M is smaller than N. Using the matrix $P_1$, a new variable x shown by $$t = P_1 x \quad (6)$$

is introduced. In the case that excitation onset times t on the endocardium and epicardium are actually calculated using this equation, t is an n-th order vector and x is an n-th order vector. Thus, using M-piece variable x that is less in the number than N-piece vertexes set thereon, it is possible to express distributions of excitation onset times on the endocardium and epicardium. Oppositely to the above equation, it is impossible to obtain x from t. Using an equation expressed by $$x = P_1^T t \quad (7)$$

enables the calculation of its approximate values.

A diagnostic system for intracardiac electrophysiological phenomena of the present embodiment is based on the above principle, and it's hardware configuration is almost the same or equivalent as or to that in the first embodiment. In the configuration, the calculating processor 14a of the computer system 14 executes a series of processes shown in FIG. 12.

Compared with the FIG. 7 described before, the processing in FIG. 12 has new processes of Steps S5a and S5b inserted into Steps S5 and S6, Step S9a takes over Step S9, and a return position from the repetition determination at Step S11 is modified to Step S5b.

Variables x and y used herein means that one variable x expresses a distribution of excitation onset times with less parameters according to equation (6) and the other variable y expresses a distribution of action potential amplitudes with less parameters in the same way. The term "less" is used to express that the number of the parameters used are less than in the foregoing first and second embodiments.

At Step S5a, by the calculating processors 14a, initial values of the variables x and y are set. Specifically, based on the initial values for the excitation onset times and action potential amplitudes both set at Step S5 described, those initial values are set from equation (7).

Then at Step S5b, the excitation onset times and action potential amplitudes are calculated. To be specific, using equation (6), excitation onset times and action potential amplitudes at each representative point within the ventricles are calculated from the variable x and y.

Then, after processing at Steps S6 and S7 (including the repetition of Steps S5b, S6 and S7), the processing goes onto Step S9a, where the variables x and y are altered, like the modifying processing for the distributions of excitation onset times and action potential amplitudes in the first embodiment.

Steps S10 and S11 are then processed likewise.

According to this analysis, inferring variables less than in the first and second embodiments is enough, providing stable inferred results and shorter inferring times.

However, in this third embodiment, when extremely small amounts are assigned to M, degrees of freedom for distributions of excitation onset times on the endocardium and epicardium are decreased, sometimes lowering spatial resolutions in the inferred distributions. Furthermore, since a magnetocardiogram calculated based on the inferred endocardiac and epicardial excitation onset times and a magnetocardiogram actually measured may become inconsistent, errors in the inferring may become larger.

To avoid this difficulty, it is preferred that in the beginning period of repetition of the non-linear optimization algorithm, a smaller value is assigned to M, and the value is increased to a value near to N as the convergence advances. At this time, newly produced variables in increasing M are given an initial value "0". This can avoid a problem that, due to a smaller M, errors in inferring the distribution of excitation onset times are increased, or the spatial resolution is lowered.

The parameters M for a distribution of excitation onset times may be different in the number from the parameters for a distribution of action potential amplitudes. In such manner, when it is accepted that a distribution of excitation onset times is lowered in the spatial resolution than a distribution of action potential amplitudes, the number of parameters for a distribution of excitation onset times can be reduced, further improving stability in inferring calculation.

Moreover, the variables x and y undergo restricted processes from the beginning in the foregoing processing of FIG. 11, the initial value setting of Step S5 can be omitted.

Fourth Embodiment

Figure 13:
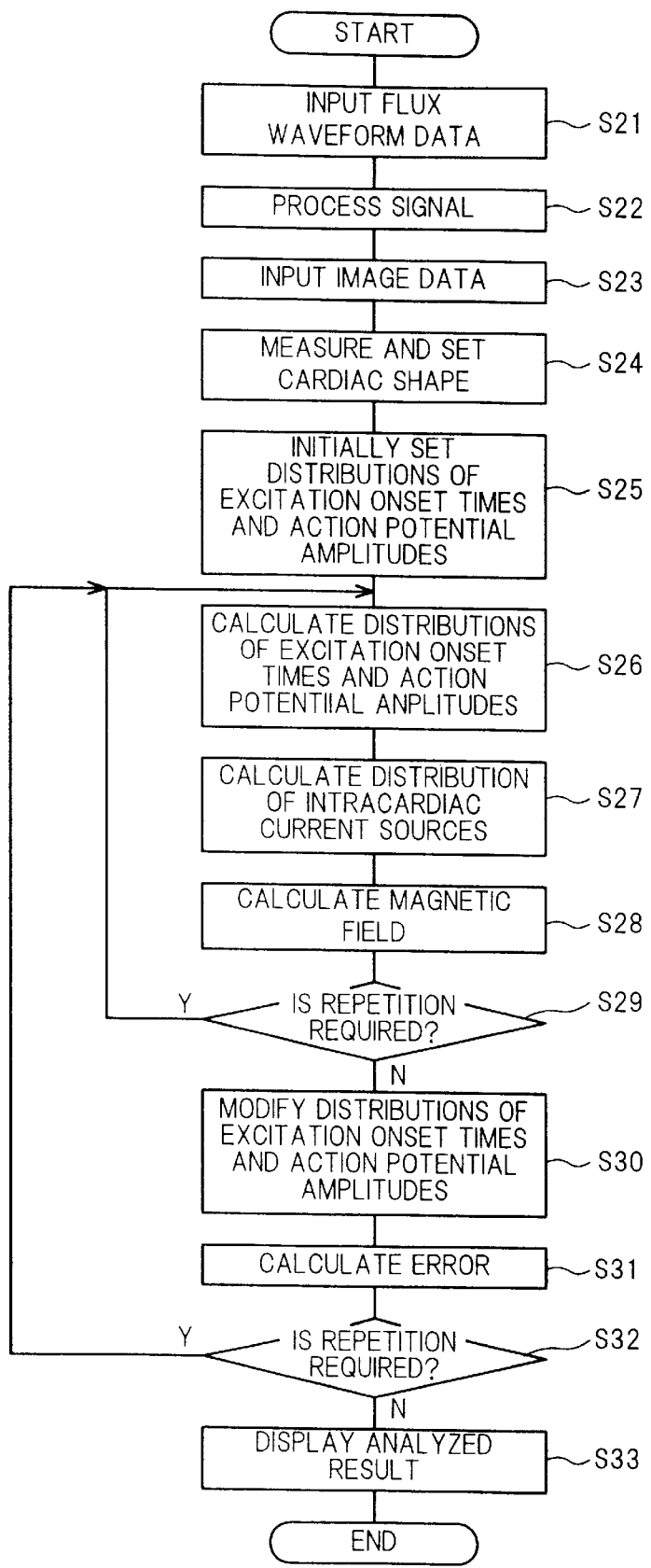
FIG. 13 is a flowchart showing inferring analysis of distributions of excitation onset times and action potential amplitudes, which is processed in the fourth embodiment.
Figure 14:
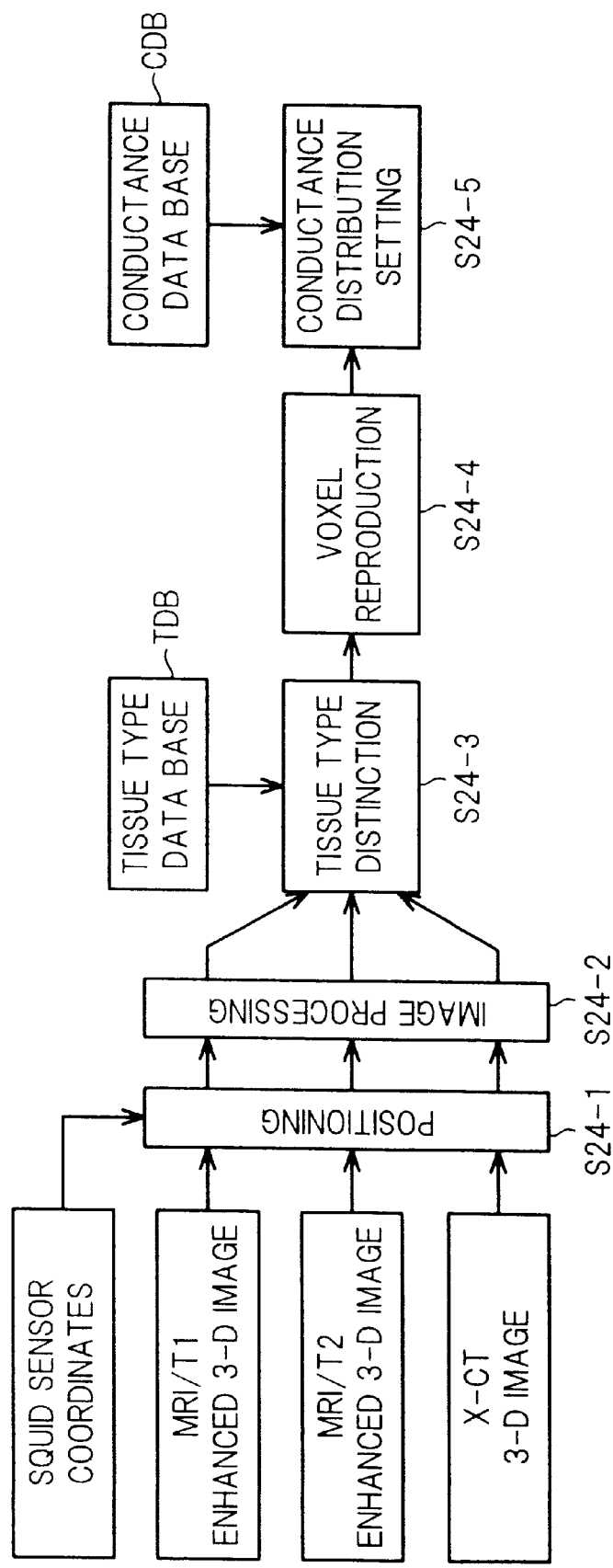
FIG. 14 outlines setting of a cardiac model in the fourth embodiment.

Referring to FIGS. 13 and 14, a fourth embodiment of the present invention will be described. A diagnostic system for intracardiac electrophysiological phenomena according to this embodiment has a feature that a ventricular model composed of a large number of voxels is used. The hardware construction of the system is almost the same or equivalent as or to that in the first embodiment.

A distribution of ventricular excitation onset times in this embodiment is expressed below. The similar expression is applied to a distribution of action potential amplitudes, its explanation being omitted herein.

First, each voxel is expressed by the array orders i, j, k in each of the x, y, z directions set for the entire voxels. The voxel numbers in the i, j, k directions are to be $N_i$, $N_j$, $N_k$. An excitation onset time at a voxel (i, j, k) is written by t(i, j, k). A discrete three-dimensional Fourier transform of t(i, j, k) is written by T(l, m, n) which is a complex number. Since t(i, j, k) are real values, the number of l, m, n are half the $N_i$, $N_j$, $N_k$, respectively.

It is assumed that T(l, m, n)=0 except components of l, m, n. This assumption corresponds to a state RF components are not included in t(i, j, k). Although excitation onset times of voxels which do not correspond to the ventricles may be expressed, such situation is to be disregarded. Using this approach, excitation onset times t(i, j, k) within the ventricles can be expressed with small components of l, m, n, that is, parameters less in the number.

FIG. 13 outlines the analysis for distributions of excitation onset times and action potential amplitudes in accordance with notation inherent to the present embodiment, and FIG. 14 outlines setting of a voxel-like ventricular model, both of which are executed by the calculating processor 14a.

The calculating processor 14a executes Steps S21 and S33 in FIG. 13 in sequence. Of these the processing from Steps S21 to S23 are the same as Steps S1 to S3 in FIG. 7 described. After that, the processing goes on to Step S24, where a voxel-like ventricular model is constructed. This construction processing is detailed in FIG. 14.

In FIG. 14, the calculating processor 14a is responsible for positioning processing (Step 24-1), image processing (Step S24-2), tissue type distinction processing (Step s24-3), voxel reproducing processing (Step S24-4), and conductance distribution setting processing (Step S24-4).

At positioning processing (Step S24-1), a positional relation between various three-dimensional images of the chest measured by MRI systems and an X-CT scanner and the coordinate systems of channels of a SQUID sensor are obtained. For positioning between amount the three-dimensional images, one preferable example is to use markers imaged together in each set of the three-dimensional images and obtain the positional relation on the assumption that the markers physically show the same positions. For positioning between the SQUID sensor and each three-dimensional image, fluxes are generated from the same spatial positions as the markers, and marker positions are obtained from the measured values. And on the assumption that the marker positions are spatially the same as those in each three-dimensional image, the positional relation is obtained.

Alternatively, the positioning may be replaced another method by which the surfaces of the chest of a patient imaged in the individual three-dimensional images are made to coincide with each other. In this case, positioning of the SQUID sensor may be performed such that the positions of flux generators attached on the chest surface are measured with the SQUID flux meter, and both their positions and a surface position of the chest in a three-dimensional image are made to agree to each other.

At image processing (Step S24-2), preprocessing is executed to make the following tissue type distinction processing easier. For example, the preprocessing includes lowing of gradations of images, noise reduction, smoothing, conversion of image sizes, differential processing, and edge detection.

A tissue type data base TDB is arranged, as shown in FIG. 13. In the data base, relational information between signal intensities and tissue types for each voxel associated with MRI T1-enhanced images, MRI T2-enhanced images, and X-CT images are stored. In the relational information, tissues, such as ventricular muscle, atrial muscle, vessels, valves, and other muscular tissue which show almost the same signal intensities, are classified as the same category.

Further, through the tissue type distinction processing (Step S24-3), signal intensities of various images which have undergone the signal processing are subjected to reference to the tissue type data base, so that tissue types are distinguished into categories voxel by voxel. Based on images for categories thus-obtained, each voxel is classified into ventricular muscle, atrial muscle, cardiac valves, muscular tissue other than the heart, blood, lungs, fat, skins, inner air, and outer air, using known information, such as the shape and position of each tissue (heart etc.). Particularly, for the ventricular muscle, atrial muscle, heart valves, and muscular tissues other than the heart which are classified into the same category, thickness values of muscular tissues and distances from the outer air are considered in the classification.

At voxel reproduction processing (Step S24-4), an image size is converted such that a useless outer air region, neck region, and/or hypogastrium region are removed and only a chest region remains in the image, and a voxel size is converted such that a conductance distribution and/or ventricular shape of the body are expressed with less voxels as possible as it could be. In this processing, instead of all the voxels processed into the same size, adopted is processing that produces voxels integer-times larger in size than the voxel of a predetermined minimum unit.

Finally, at conductance distribution setting processing (Step S24-5), a conductance of each voxel is set by referring a conductance data base CDB where representative conductance values for classified tissue types are stored.

Then initial value setting is performed for distributions of excitation onset times and action potential amplitudes (step S25). Practically, T(l,m,n) is set as initial values for the variable T, where T(l,m,n) is produced such that l, m, n other than values whose discrete three-dimensional Fourier transform of a typical distribution of excitation onset times for a normal heart are small is are set to zero. Alternatively, if T (l,m,n) is such that its components for small l, m, n are set at random and its remaining components are set to zero, T (l,m,n) can be set as initial values for the variable T. For a distribution of action potential amplitudes, the initial setting is also performed, like the same way.

Then, distributions of excitation onset times and action potential amplitudes are calculated (Step S26). In detail, T(l,m,n) undergoes a discrete three-dimensional inverse Fourier transform to obtain a distribution of excitation onset times. The similar calculation is applied to a distribution of action potential amplitudes.

Then, inferring a distribution of intracardiac current sources is executed as follows (Step S27). A current dipole moment J(i,j,k) for a specified voxel (i,j,k) at a certain time instant $T_1$ is obtained by $$J(i, j, k) = \begin{pmatrix} J_x(i, j, k) \\ J_y(i, j, k) \\ J_z(i, j, k) \end{pmatrix}. \quad (8)$$

From this equation, $$J_x(i, j, k) = \begin{cases} \sigma(i, j, k)A_x(i, j, k)\Phi(i, j, k)(\text{if}, t(i-1, j, k) < 2t_1 - t(i, j, k) \le t(i+1, j, k)) \\ -\sigma(i, j, k)A_x(i, j, k)\Phi(i, j, k)(\text{if}, t(i-1, j, k) > 2t_1 - t(i, j, k) \ge t(i+1, j, k),) \\ 0 \quad \text{(other than the above)} \end{cases} \quad (9)$$

$$J_y(i, j, k) = \begin{cases} \sigma(i, j, k)A_y(i, j, k)\Phi(i, j, k)(\text{if}, t(i, j-1, k) < 2t_1 - t(i, j, k) \le t(i, j+1, k)) \\ -\sigma(i, j, k)A_y(i, j, k)\Phi(i, j, k)(\text{if}, t(i, j-1, k) > 2t_1 - t(i, j, k) \ge t(i, j+1, k),) \\ 0 \quad \text{(other than the above)} \end{cases}$$

$$J_z(i, j, k) = \begin{cases} \sigma(i, j, k)A_z(i, j, k)\Phi(i, j, k)(\text{if}, t(i, j, k-1) < 2t_1 - t(i, j, k) \le t(i, j, k+1)) \\ -\sigma(i, j, k)A_z(i, j, k)\Phi(i, j, k)(\text{if}, t(i, j, k-1) > 2t_1 - t(i, j, k) \ge t(i, j, k+1),) \\ 0 \quad \text{(other than the above)} \end{cases}$$

are obtained, where σ(i,j,k) is an intracellular conductance at voxel (i,j,k), $A_x(i,j,k)$, $A_y(i,j,k)$, and $A_z$ (i,j,k) are cross sections of voxels along planes perpendicular to the i, j, and k directions of voxels (i,j,k), respectively, and Φ(i,j,k) is an action potential amplitude at voxel (i,j,k).

Further, magnetic fields are calculated (Step S28). Like the first embodiment, this processing is performed using the Biot-Savart law or sarvas's equation to obtain amplitudes of magnetic fields measured by the SQUID sensor. Instead of this manner, the conductance distribution of tissues set at Step S24 (cardiac shape measuring and setting processing) can be used to calculate magnetic fields according to a differential method. The differential method is a technique to solve a partial differential equation using grid-like representative points, and is simple in algorithm compared to a boundary element method or finite element method.

The processing composed of Steps S26 to S28 is repeated according to necessity (Step S29).

And modification processing of distributions of excitation onset times and action potential amplitudes and calculation processing of errors are repeated by necessary times, essentially in the same way as that in the first embodiment (Steps S30 to S32). After this, both the resultant distributions are displayed, for example, in the same fashion as in the first embodiment (Step S33).

In the conventional inferring processing, increasing inferring accuracy requires the shapes of the heart, lungs, body, and others to be expressed actually. Thus a boundary element method or finite element method was used. For example, in the case of the boundary element method, triangles are combined to form the surfaces of the heart, lungs, and body. To produce such models, boundaries of tissues should be extracted in three-dimensional images from MRI or X-CT modalities, and triangular meshes to approximately trace the boundary surfaces should be formed. However, automatically performing this entire formation was difficult. Additionally it was actually impossible to produce triangular meshes of tissue boundaries that was made to be fitted to each patient, because of troublesome work. In case that the finite element method is used, although a three-dimensional region is divided with tetrahedral or hexahedral meshes, but it needs the boundaries of the tetrahedrons or hexahedrons to agree with the boundaries of tissues, thus similar difficulties to the foregoing boundary element method being caused.

In contrast, the present invention uses expressions of the shape of the heart or chest, or a distribution of conductance values. This eliminates the need for making triangular meshes or, tetrahedral or hexahedral meshes coincide with tissue boundaries to form a model. Only classifying the tissue of each hexahedron regularly disposed in a grid pattern, according to its type, is enough. Thus, since a ventricular or body model can be formed easily from MRI or X-CT three-dimensional images, a ventricular model can be produced easily in agreement with individual differences in all patients under examination, and the ventricular model can be used to concurrently analyze both distributions of excitation onset times and action potential amplitudes. Additionally, a conductance distribution model of each patient is easily produced to be utilized in calculation of potentials and magnetic fields, which leads to higher accuracy in analyzing the distributions of excitation onset times and action potential amplitudes than the conventional methods. In particular, the analysis in this embodiment needs less amounts of analysis procedures, the analysis can be easily performed for a large number of patients with a higher patient throughput, providing a higher effectiveness for practical use of the diagnostic system.

Other alternative embodiments for the foregoing first to fourth embodiments will be described below.

Although the foregoing embodiments have focused on inferring an excitation onset time distribution from measured magnetic fields of the heart, this inferring approach can be applied to inferring an excitation onset time distribution from an electrocardiogram data acquired by a not shown electrocardiograph.

Furthermore, objectives to be analyzed exemplified in the foregoing embodiments have been distributions of excitation onset times and action potential amplitudes. With this respect, various alternative embodiments are also possible. For example, a distribution of action potential amplitudes can be replaced by any of a ventricular distribution of conductance values, a ventricular distribution of absolute current dipole densities which are multiplication between action potential amplitudes and conductance values, or a distribution formed by a relevant or deformed quantity to or from those quantities. Even in such alternative examples, the substantially equivalent advantages to the foregoing embodiments can be obtained.

Fifth Embodiment

Referring to FIGS. 15 to 30, a fifth embodiment of the present invention will be described. From this embodiment to the last embodiment, how analyzed or estimated results are visualized will be described.

Figure 15:
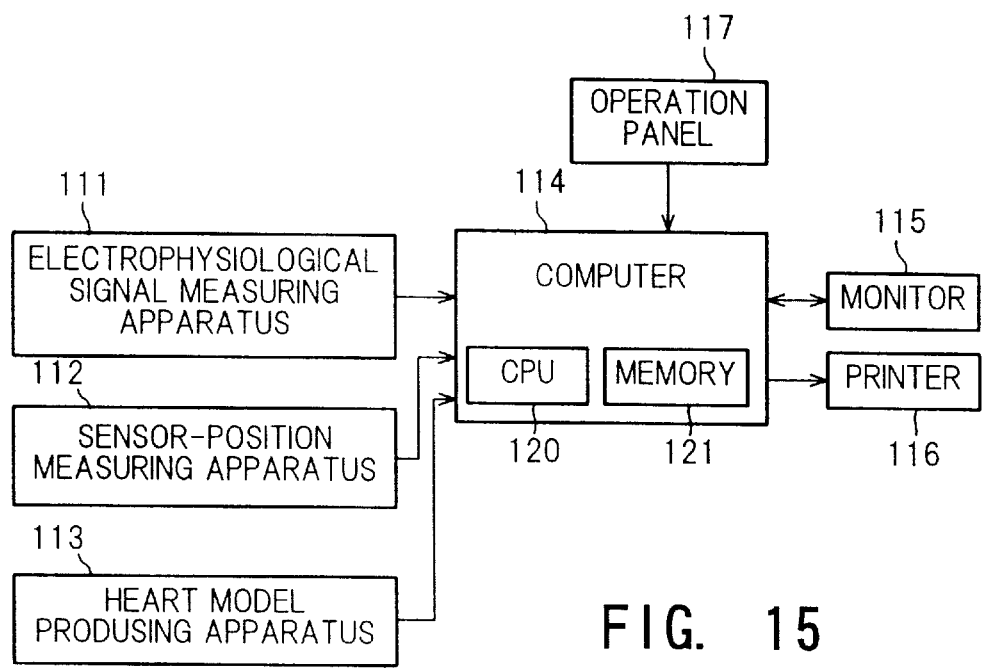
FIG. 15 shows a schematic block diagram of another diagnostic system for intracardiac electrophysiological phenomena according to the present invention.

A diagnostic system for intracardiac electrophysiological phenomena shown in FIG. 15 is provided with an electrophysiological signal measuring apparatus 111 for data input, a sensor-position measuring apparatus 112, a heart model producing apparatus 113, a computer 114 for data calculating and processing, a monitor 115 and printer 116 for data output, and an operation panel 117. The computer 114 includes a CPU 120 for calculation and various memories 121.

The electrophysiological measuring apparatus 111 acts as means for measuring distributions of potentials and magnetic fields. The measuring apparatus 111 measures potentials or magnetic fields (fluxes) emanated from the heart of a patient as an object to be examined. For potential measurement, the measuring apparatus 111 comprises electrodes for an electrocardiogram, amplifiers, and A/D converters. On one hand, for magnetic field measurement, the measuring apparatus 111 is composed of a flux sensor using SQUIDs, as a typical fashion. Multi-channel measuring points are used for the measurement. For example, the points consists of 40 to 100 points on the chest. Measured waveform signals are converted channel by channel by the A/D converters in the apparatus 111, and then sent to the computer 114.

Using three-dimensional tomographic data acquired by clinical imaging modalities, such as MRI systems or X-CT scanners, the heart model producing apparatus 113 measure the shape, spatial position, and direction of the heart of each patient to produce data indicative of a model shape of the ventricles. The model shape data produced are sent to the computer 14.

Figure 17:
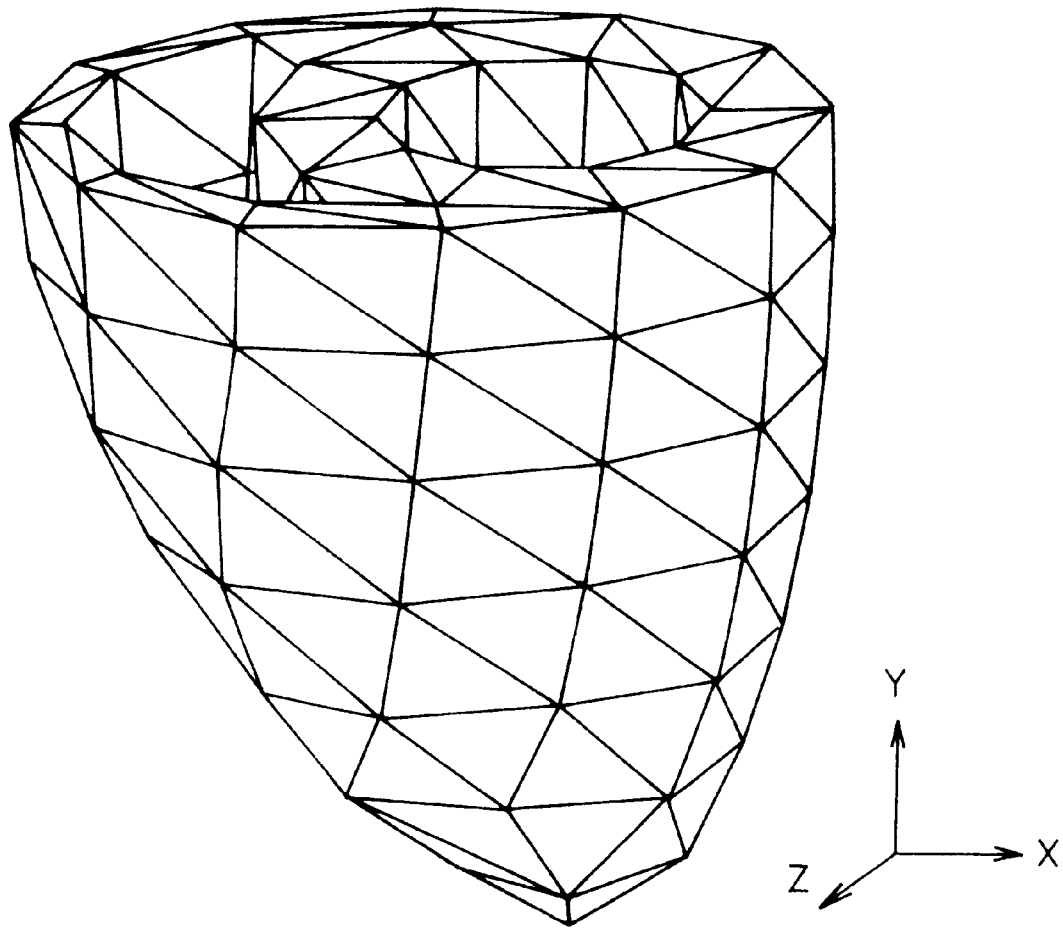
FIG. 17 is an oblique view showing a ventricular model.

FIG. 17 exemplifies a ventricular model (i.e., heart model). The model is formed by combining a number of tetrahedrons. The heart model producing apparatus 113 is capable of automatically producing such ventricular model in response to specification of parameters including a length in the major-axis direction of the ventricles, an outer diameter in the minor-axis direction of the left ventricle (L.V.), a well thickness of the L.V., a wall thickness of the right ventricle (R.V.), a width between the septum and the R.V. According to the specification of the parameters, the model can be formed with tetrahedrons divided into an arbitrary size. While the model shown in FIG. 17 are expressed with tetrahedrons, other polyhedrons such as pentahedrons or hexahedrons can also be used to form ventricular models.

By translating and rotating the ventricular model thus-formed to a position and a direction of the heard defined by clinical imaging modalities such as an MRI system, the model can be set with the same relationship as an actual position within the body of a patient.

The sensor-position measuring apparatus 112 is used to measure electrodes for potential measurement or flux sensors for magnetic field measurement and obtain the positional relationship between the model and the electrodes or sensors.

For example, markers are attached to positions for electrodes in MRI imaging, and the positions for an MRI image. Alternatively, for measuring a magnetocardiogram (MCG), a few flux generating coils are attached on the chest surface. The fluxes (magnetic fields) generated therefrom are measured and analyzed to determine the positional relationship between each flux generating coil position and each sensor. Then markers are attached on the coil positions, the positions of the markers are specified on an MRI image, and the coordinates of each sensor are converted based on the specified positions, thereby the sensor positions to the patient body being provided. The positions of the electrodes or sensors thus-measured are sent to the computer 114, providing data necessary for analysis of distributions of excitation onset times and a myocardial electroaction amount.

Figure 16:
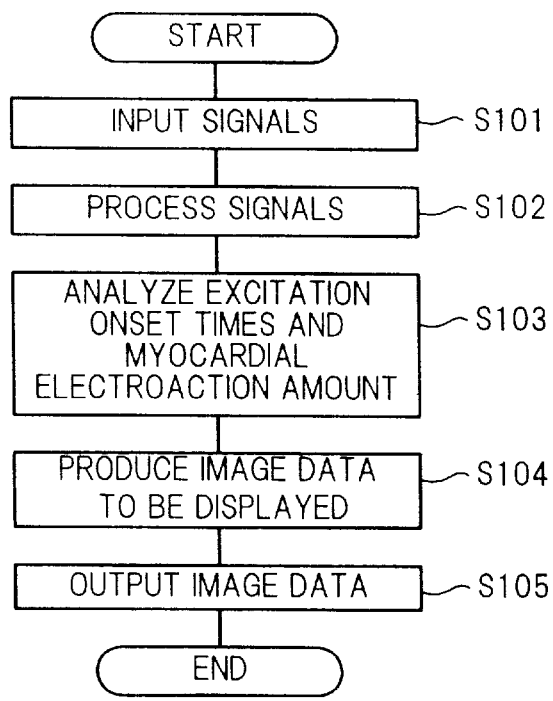
FIG. 16 outline a flowchart showing processing executed in a CPU in a fifth embodiment of the present invention.

The CPU 120 is designed to execute predetermined processing according to a program pre-stored in the memories 120. FIG. 16 outlines the processing. That is, the CPU 120 executes Step S101 for inputting output signals from the measuring apparatus 111 and 112 as well as the producing apparatus 113, Step S102 for processing a measuring signal by the electrophysiological phenomena measuring apparatus 111, Step S103 for analyzing a myocardial electroaction amount and excitation onset times based on the processed signal, Step 104 for producing image data to be displayed based on the analyzed results, and Step S105 for outputting the produced image data. Of these the producing Step S104 for display of image data constitutes another feature of the present invention.

At Step S102 for signal processing, the CPU 120 performs filtering for noise reduction and others with the measured signal sent from the measuring apparatus 111, and extracts a waveform signal corresponding to a QRS interval in an electrocardiogram (ECG) or magnetocardiogram (MCG). At Step 103 for analysis, the CPU 120 calculates distributions of excitation onset times and a myocardial electroaction amount caused in the heart through well-known approaches, on the basis of ECG or MCG data during the QRS interval signal-processed at Step S102, ventricular model data produced by the apparatus 113, and sensor-position data measured by the apparatus 112. The myocardial electroaction amount is, for example, any one of an action potential amplitude (refer to FIG. 5), conductance, and current dipole density which is multiplication between the conductance and the action potential amplitude, but not limited such list.

Step S104 functionally constitutes means for producing data to be displayed. That is, at this processing, the CPU 120 adds a variety of kinds of processing to the analyzed results concerning distributions of excitation onset times and a myocardial electroaction amount. As a result of it, formed are image data that provides analysis images easier for doctors, examining staffs, or patients to observe or understand.

Then, at Step S105, the CPU 120 outputs the analyzed results, that is, image data produced at Step S104, to the monitor 115 and/or printer 116. The monitor 115 is, for example, a CRT display or liquid crystal display. The printer 116 can print images on paper or films. Thus the monitor 115 and/or printer 116 can have the ability that displays such user-friendly images.

The followings are examples, where various types of images are produced and displayed by the processing of the CPU 120 at Steps S104 and S105. The CPU 120 is also designed such that in response to a command sent from the operation panel 117, it selects any one of the display modes which will be described in the followings.

First Display Example

A first example of display relates a display mode in which a distribution of excitation onset times are displayed as an isochrone chart on a sectional view of the ventricular model. The isochrone chart is made by connecting points at which excitation occurs at the same times instants.

Figure 18:
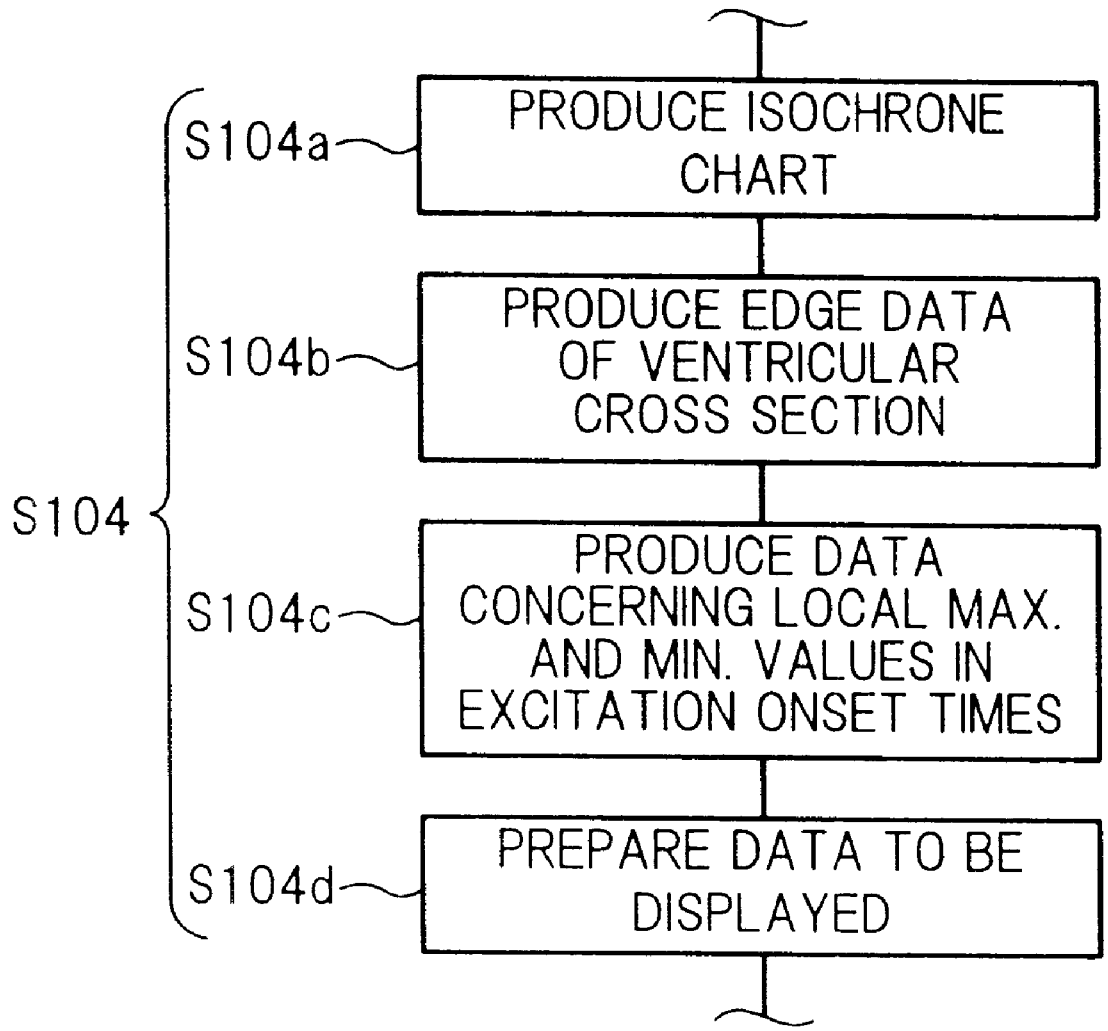
FIG. 18 is a flowchart for producing image data to be displayed in a first display example of the fifth embodiment.

To perform this display, the CPU 120 executes a series of processes partially shown in FIG. 18, which corresponds to Step S104 in FIG. 16 and is its detailed form. Data of an isochrone chart are produced as a distribution of excitation onset times (S104*b*), data of the edge of a ventricular cross section are produced (Step S104*b*), data of local minimum and maximum values in the excitation onset times are produced (Step S104*c*), and data to be displayed are formed (Step S104*d*).

A precondition is that a ventricular model is composed of M-piece tetrahedrons having N-piece apexes in all and excitation onset times are given the N-piece apexes. The edge of a ventricular model is made up of L-piece triangles.

Figure 19:
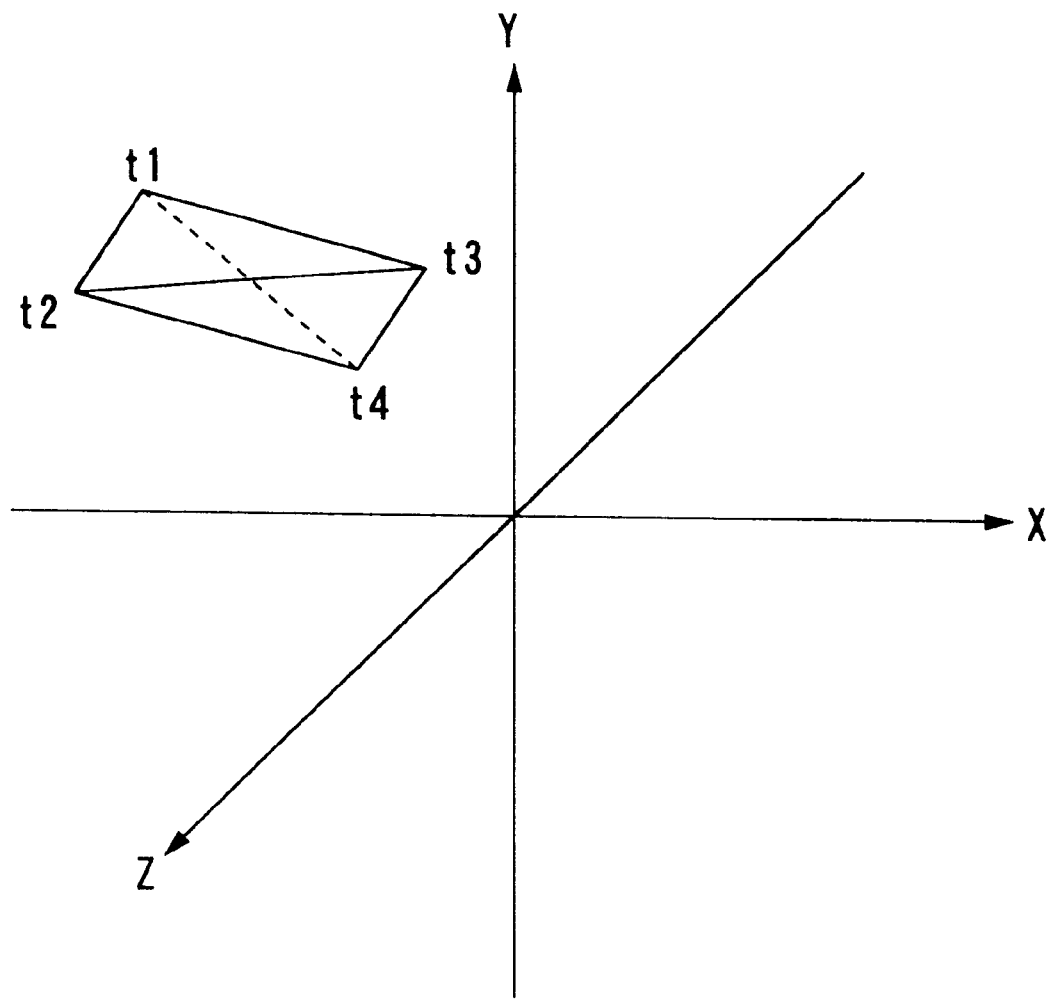
FIG. 19 explains the relationship between a tetrahedron constituting a ventricular model and its coordinate system.

In the orthogonal coordinate system having X-, Y-, and Z-axes shown in FIG. 17, one possible choice is that a desired ventricular cross section to be displayed (display cross section) is an XY cross section at z=0 in the Z-direction. Thus image data to display an isochrone chart on the cross section in a superposition manner are to be produced. It is also assumed a tetrahedron has four apexes (N=4) and excitation onset times are given the four apexes at t1, t2, t3, t4 as shown in FIG. 19.

Figure 20:
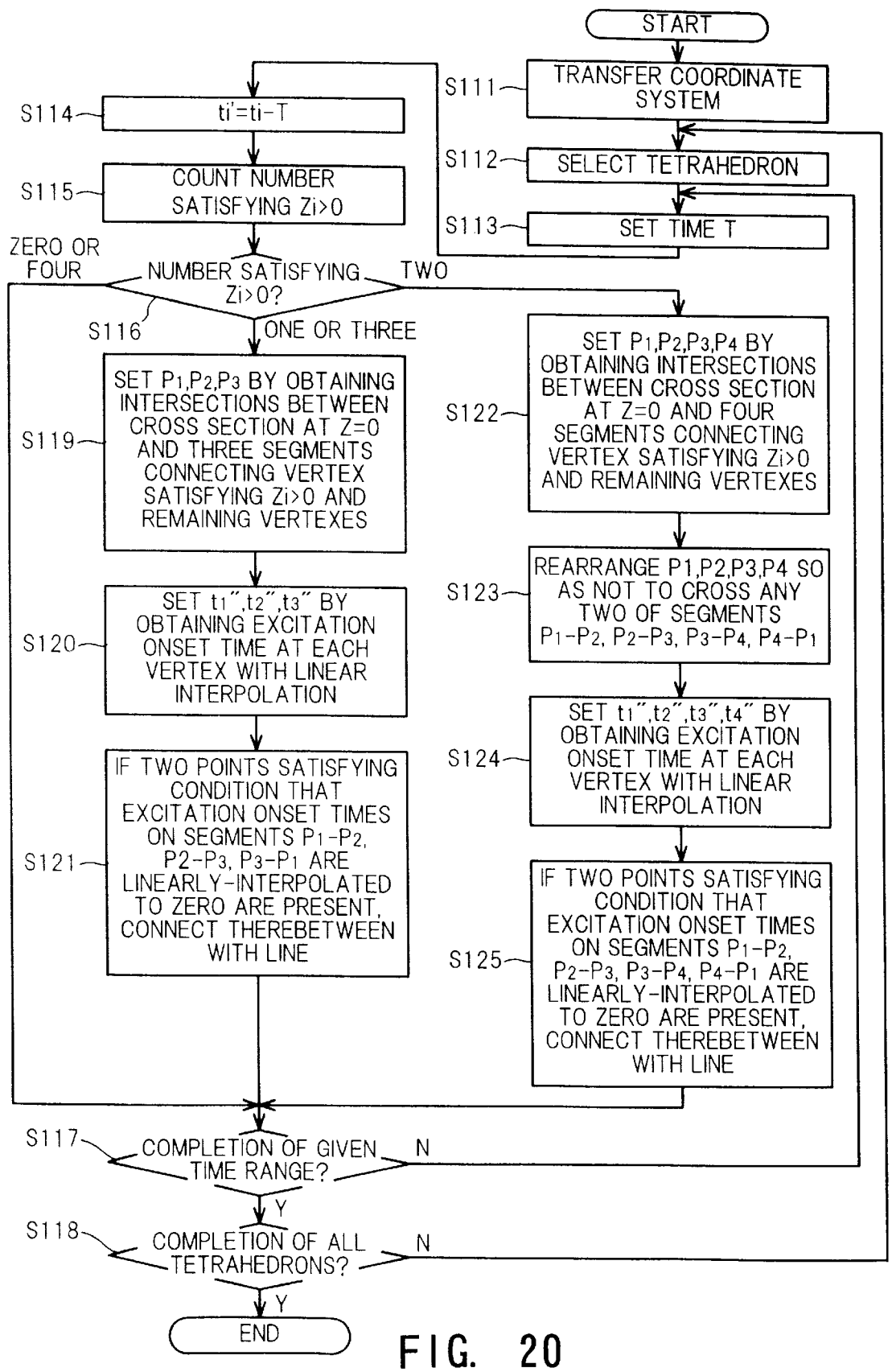
FIG. 20 is a detailed flowchart showing the production of isochrone chart data in the first display example.

One example of algorithms for producing isochrone chart data executed at Step S104*a* is shown in FIG. 20. This algorithm shows a procedure of producing isochrone chart data of a certain tetrahedron at a time instant T, wherein the same processing is repeated a plurality of times as the time instant T is changed, then the same processing is repeated over all the tetrahedrons.

Detailed description is as follows. The CPU 120 transfers the coordinate systems for the apexes of each tetrahedron such that those coordinates are positioned on the foregoing display cross section, which is an XY plane at z=0 (Step S111). The CPU 120 selects one tetrahedron from a plurality of tetrahedrons forming a ventricular shape (Step S112), and sets a given value (for example, 10 ms) to the time T (Step S113).

The CPU 120 executes a conversion of ti'=ti−T (i=1,2,3,4) with regard to the time T (Step S114). This conversion makes it allowed in the following to consider display of an isochrone chart at ti'=0 alone.

Then, for a specified tetrahedron, the number of apexes whose z-coordinate zi(i=1 to 4) is positive is counted (Step S115). The number should be from 0 to an integer 4. As the next step, the number of apexes being Zi>0 is determined (Step S116).

In this determination, if the number of apexes being Zi>0 is zero or four, the tetrahedron under processing residues in either one of the plus-side are or minus-side of the Z-axis. This is, this tetrahedron does not intersect the display cross section at z=0, thus no relation is given an objective isochrone chart. Hence the CPU 120 skips the producing processing, and goes directly to Steps S117 and S118. It is determined whether or not the image data producing processing has been completed for all times falling in an objective given time range (Step S117). If YES is accomplished at this determination, it is further determined whether or not the producing processing has been completed for all the tetrahedrons (Step S118). If unprocessed times T remain (NO at Step S117), the processing returns to the foregoing Step S113. Further, if unprocessed tetrahedrons remain (NO at Step S118), the processing returns to the forgoing Step S112.

Figure 21:
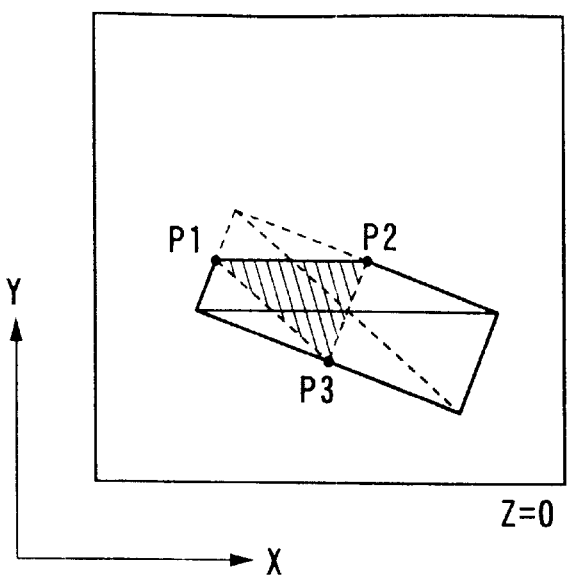
FIG. 21 is an explanation explaining the production of isochrone chart data.

On one hand, if the number of apexes being Zi>0 is one or three at Step S116, the tetrahedron under processing provides a triangular cross section intersecting the display cross section residing at z=0, as shown in FIG. 21. Therefore, the CPU 120 computes three apexes p1, p2, p3 defining the triangular cross section within the tetrahedron (Step S119), and obtains excitation onset times t1", t2", t3" at the three apexes p1, p2, p3 by linear interpolation (Step S120). Then segment data are produced as follows (Step S121). First, linear interpolation is performed to obtain points which provide the excitation onset time=0 on the three sides p1–p2, p2–p3, p3–p1 of this triangle. If the number of the points is zero, it is not needed to depict this triangle, ending the processing. If the number is two, segment data to depict an isochrone chart are produced by connecting the two points to each other (Step S121). Then the foregoing Steps S117 and S118 are repeated.

Figure 22:
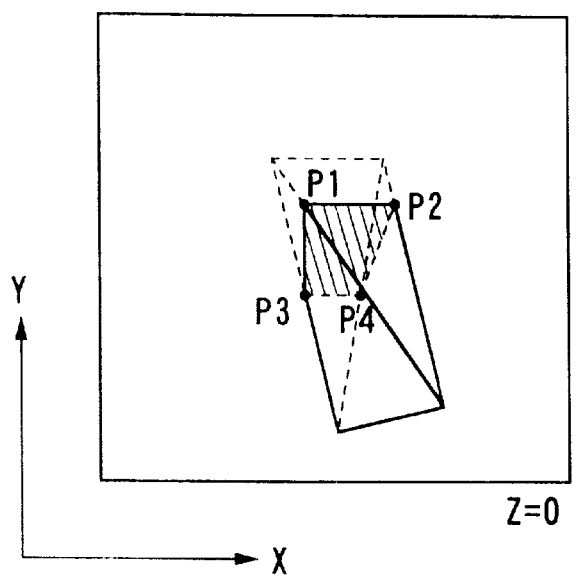
FIG. 22 is another explanation explaining the production of isochrone chart data.

Furthermore, in the case that the number of the apexes being zi>0 is two in the determination at Step S116, a cross section of the tetrahedron, which intersects the display cross section residing at z=0 becomes a rectangular, as shown in FIG. 22. The CPU 120 computes four apexes p1, p2, p3 and p4 defining the rectangular cross section within the tetrahedron (Step S122). By the CPU 120, whether or not any two of four segments p1–p2, p2–p3, p3–p4 and p4–p1 intersect the display cross section residing at z=0 is determined, and if the intersection is determined, the apexes p1, p2, p3 and p4 are realigned in the order to form a rectangular by p1, p2, p3 and p4 (Step S123). Then, excitation onset times t1", t2", t3" and t4" at the four apexes p1, p2, p3 and p4 are calculated with linear interpolation (Step S124). Then, segment data are produced as follows (Step S125). First, linear interpolation is performed to obtain points which provide the excitation onset time=0 on the four sides p1–p2, p2–p3, p3–p1 and p4–p1 of this rectangle. If the number of the points is zero, it is not needed to depict this rectangle, ending the processing. If the number is two, segment data to depict an isochrone chart are produced by connecting the two points to each other (Step S125). Then the foregoing Steps S117 and S118 are repeated.

Further, at Step 104*b* in FIG. 18, the CPU 120 produces data of an edge of a ventricular model. Practically, it computes a cross line between each of the L-piece triangles given as the edge of the model and the display cross section, and regards data of the cross section as segment data.

At Step S104*c* in FIG. 18, the CPU 120 calculates local minimum and maximum values and their positions in the excitation onset times as follows. The local minimum value is a time instant which is the fastest in excitation onset on their two-dimensional map, while the local maximum value a time instant which is the slowest thereon.

The calculation is carried out on condition that the excitation onset times change linearly within a tetrahedron. This condition makes the local minimum and maximum values exist only at the apexes of the tetrahedrons. If an excitation onset time at a certain apex is larger than those times at all the other apexes of the tetrahedrons co-possessing the certain apex, the excitation onset time at the certain apex becomes a local minimum value. In contrast, an excitation onset time at a certain apex is smaller than those times at all the other apexes of the tetrahedrons co-possessing the certain apex, the excitation onset time at the certain apex becomes a local maximum value. Using this algorithm, the CPU 120 repeats the determination of local minimum or maximum values for all the tetrahedrons, and compares those with each other, obtaining the values as well as positions presenting their values.

After this series of processes, the CPU 120 synthesizes data calculated at Steps S104a to S104c a two-dimensionally mapped frame data for display, and store them in the memories (Step S104d). In this synthesis, superposed together are time value data indicative of isochrones for excitation onset times, in addition to graphic data of arrows indicative of the local minimum and maximum data and their time value data.

The mapped frame data thus-prepared are sent from the computer 114 to the monitor 115 and/or printer 116 (Step S105).

Figure 23:
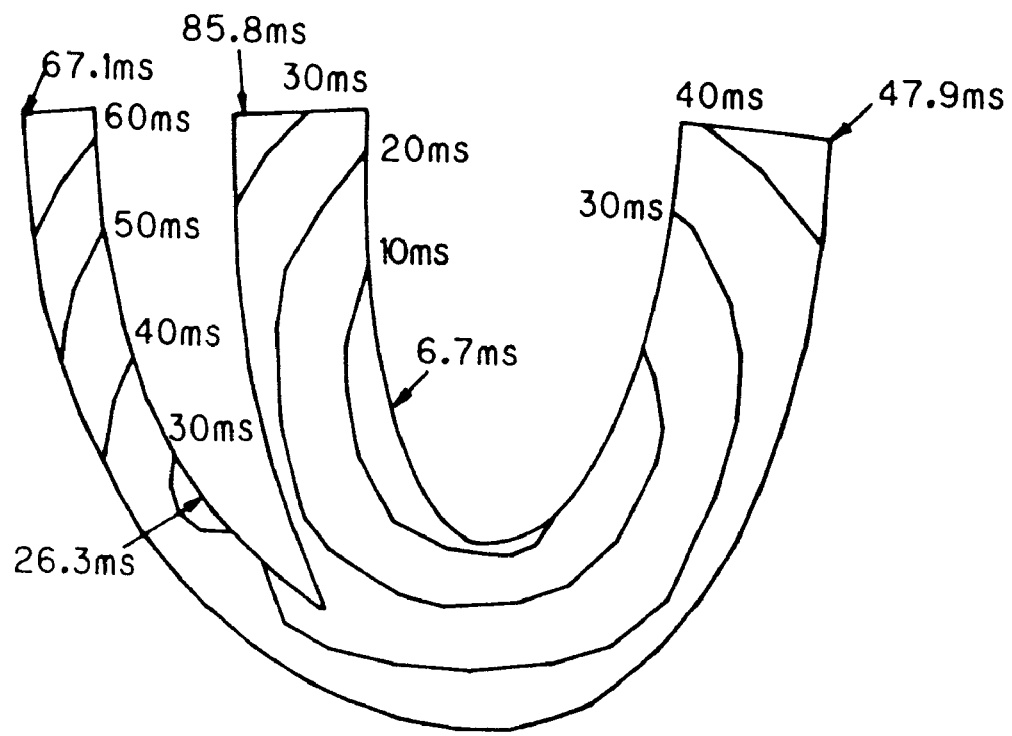
FIG. 23 is an image represented by a monitor or printer in the first display example.

Consequently, as shown in FIG. 23, the monitor 115 and/or printer 116 provides an image wherein an isochrone chart indicative of an excitation onset time distribution is superposed on the cross section of the ventricles. This isochrone chart shows the spatial excitation positions on the ventricular section, which are connected by lines at regular-interval time instants (in the figure, 10 ms, 20 ms, . . . , 60 ms, etc.). Additionally a time instant values 10 ms, 20 ms, etc. For the lines are added to proper positions in the displayed image. Arrows indicating positions at which the local minimum and maximum values are present are also shown thereon and their propagated time instants to the values are additionally put. Adding those additional figures facilitates quantitative interpretation and relieve an operational or diagnostic burden to operators or interpreters.

Second Display Example

A second example of display relates a display mode in which a distribution of excitation onset times are displayed as colored gradation image or gray-scale density image on a sectional view of the ventricular model and an isochrone chart is concurrently superposed thereon.

Figure 24:
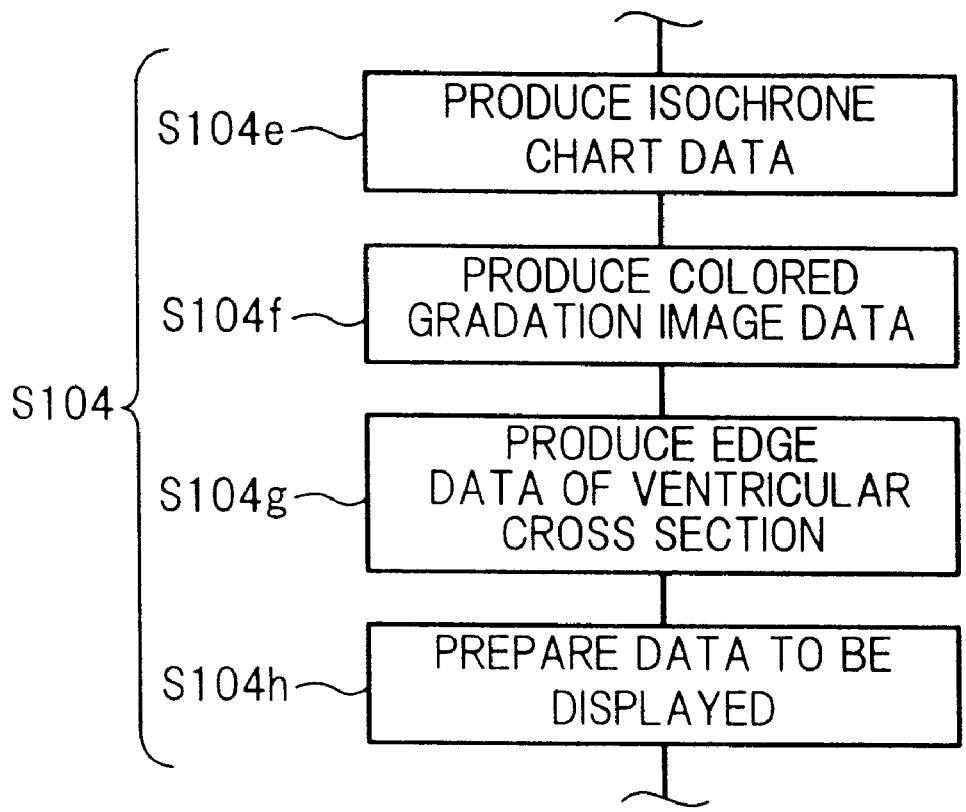
FIG. 24 is a flowchart for producing image data to be displayed in a second display example of the fifth embodiment.

As shown in FIG. 24, the CPU 120 executes processing corresponding to Step S104 in FIG. 16. The processing is composed of producing isochrone chart data of excitation onset times (Step S104e), producing colored gradation image data indicating a distribution of excitation onset times (Step S104f), producing edge data of a ventricular cross section (Step S104g), and preparing data to be displayed (Step S104h). Of these, processing at Steps S104e and S104 g is the same as Steps 104a and 104b described before.

Figure 25:
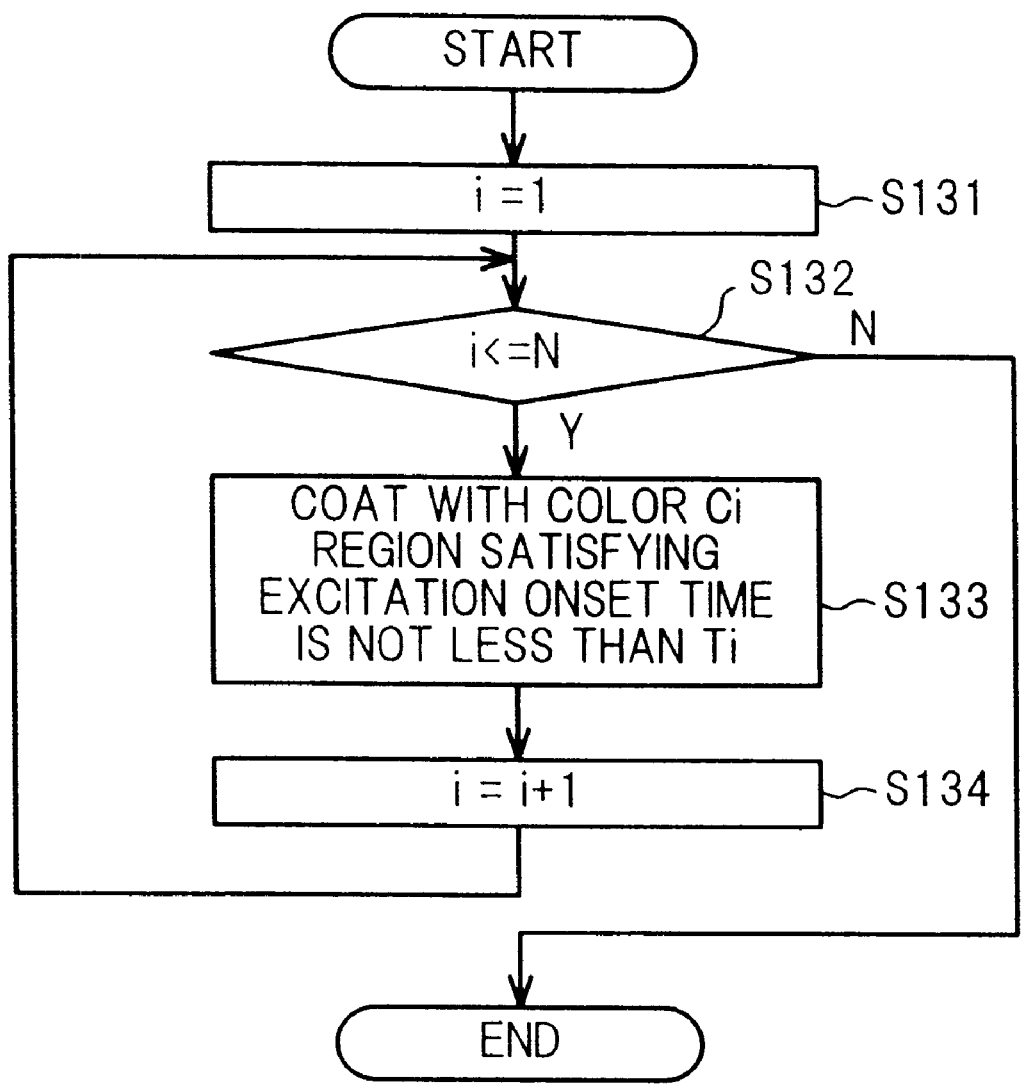
FIG. 25 is a detailed flowchart explaining a production example of color-gradated image data in the second display example.

Processing carried out by the CPU 120 at Step 104f is outlined in FIG. 25, in which procedures to classify distribution data of excitation onset times into N-types of colors (hues) Ci (i=1. . . N). First, a parameter i is set to i=1 (Step S131), then if i≦N or not is determined (Step S132). If the determination is YES (i.e., i≦N), data of colors Ci are assigned to positions (pixels) whose excitation onset time is larger than Ti. This assignment of colors Ci is repeated for every position (pixel) composing a two-dimensional map (Step S133). After this, the parameter i is updated to i=i+1 (Step S134), returning to the determination of Step S132.

As long as the determination keeps YES, data of color Ci+1 are assigned to positions (pixels) whose excitation onset times are more than Ti+1. This is repeated for each position (Step S133). This repetition causes color Ci to be assigned to a displaying region (a group of pixels) defined by excitation onset times T falling into its threshold band from Ti to Ti+1. When the processing at Step S133 is repeated once more, color Ci+1 is assigned to another displaying region defined by excitation onset times T falling into its threshold band from Ti+1 to Ti+2.

This sequential processing is repeated until i>N is established. In consequence, each position (pixel) in a distribution composed of two-dimensionally mapped excitation onset times is classified respectively with thresholds of time instants Ti, . . . , $T_N$. In general, classified positions (pixels) becomes regions having irregular widths. N-types of color data are assigned to classified regions, respectively.

Further, at Step S104h in FIG. 24, edge data of a ventricular cross section, distributed color data of the excitation onset times, and data of the isochrone chart data (together with figure data indicative time instants) are synthesized into frame data.

Figure 26:
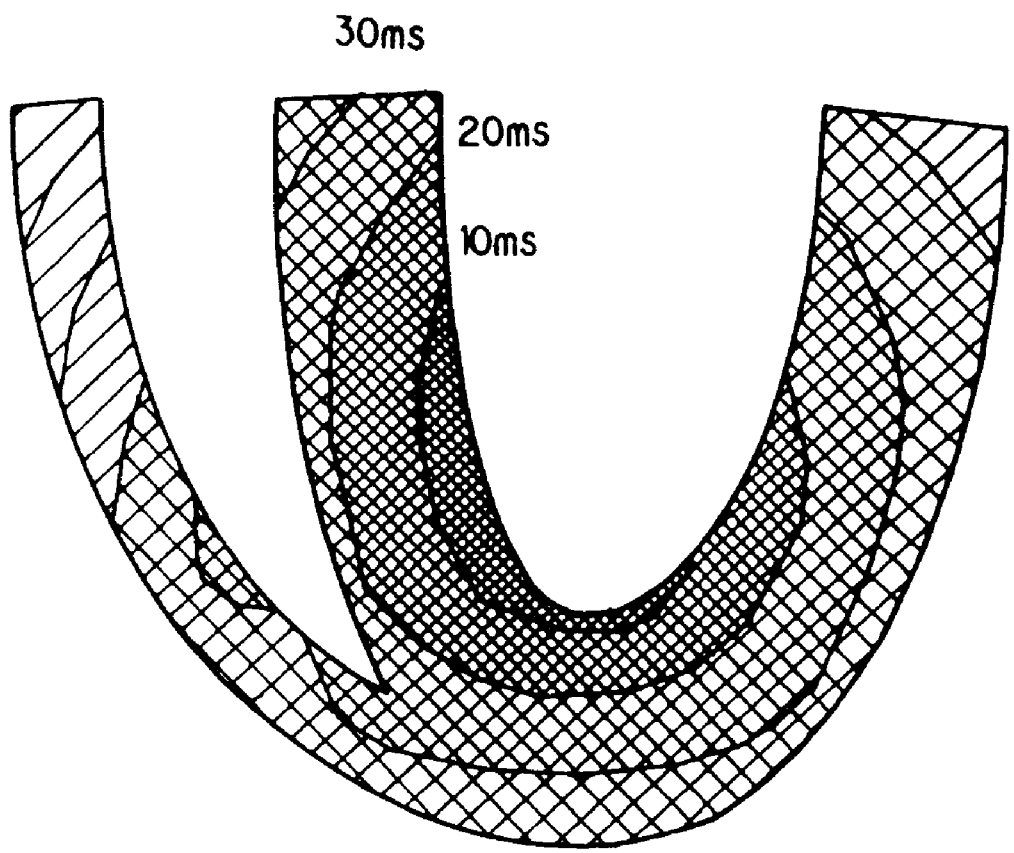
FIG. 26 is an image represented by a monitor or printer in the second display example.
Figure 27:
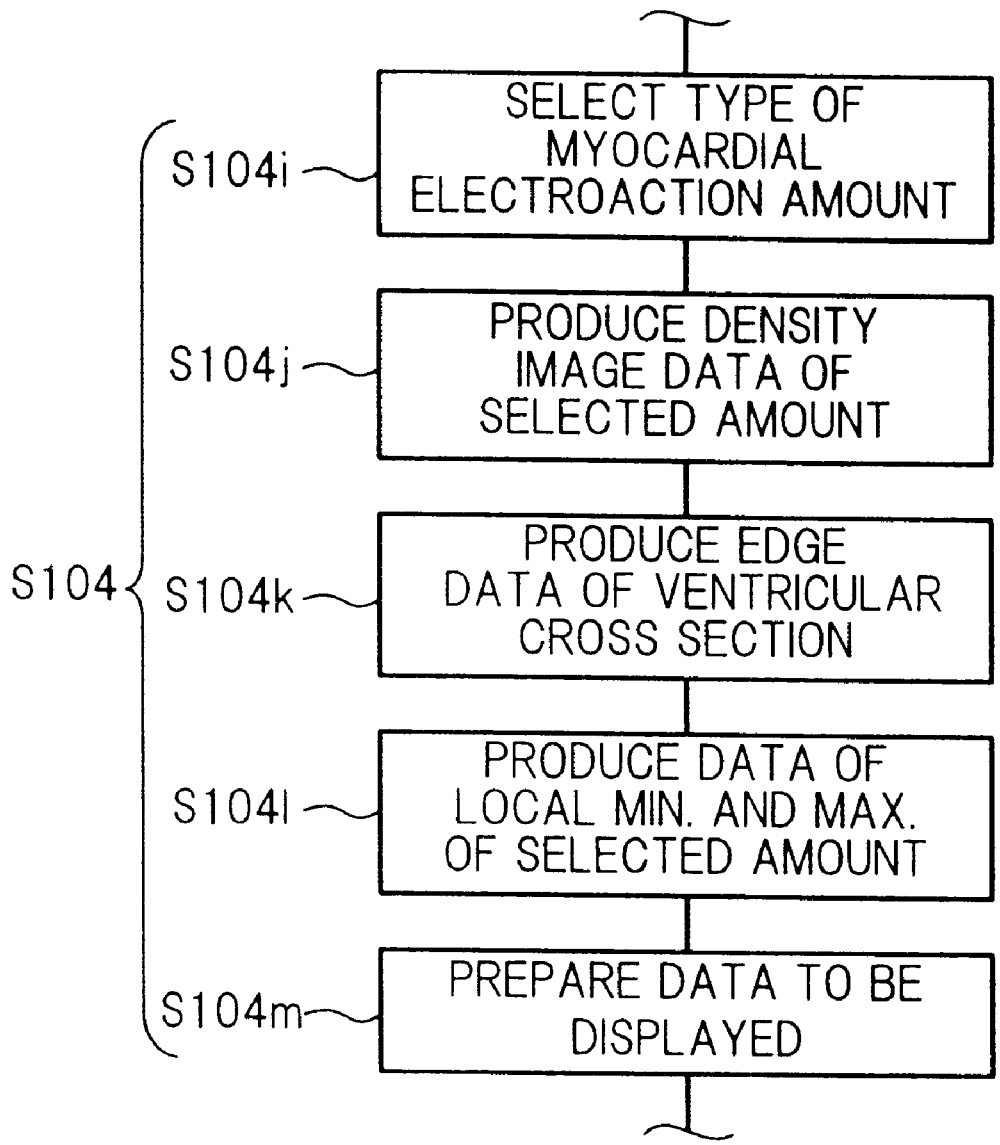
FIG. 27 is a flow chart for producing image data to be displayed in a third display example of the fifth embodiment.

The monitor 115 and/or printer 116 provides an image, as shown in FIG. 26, where an excitation onset time distribution including strip-like colored regions is superposed on a ventricular cross section and its isochrone chart is also superposed. Since the excitation onset times are distinguished with colors (hues) to show the progress of the times, a superior visibility is provided. Since the isochrone chart is also used, the same or equivalent advantages as or to those in the first display example are obtained.

Instead of distinguishing with colors (hues) as above, either one method of distinguishing with brightness degrees of a certain hue changed or distinguishing with gray-scale densities changed may be adopted. Such distinction is realized by replacing the colors Ci to brightness degrees or densities at Step S133.

Third Display Example

A third example of display is to visualize a myocardial electroaction amount distribution as a density image superposed on a cross section image of a ventricular model.

Figure 28:
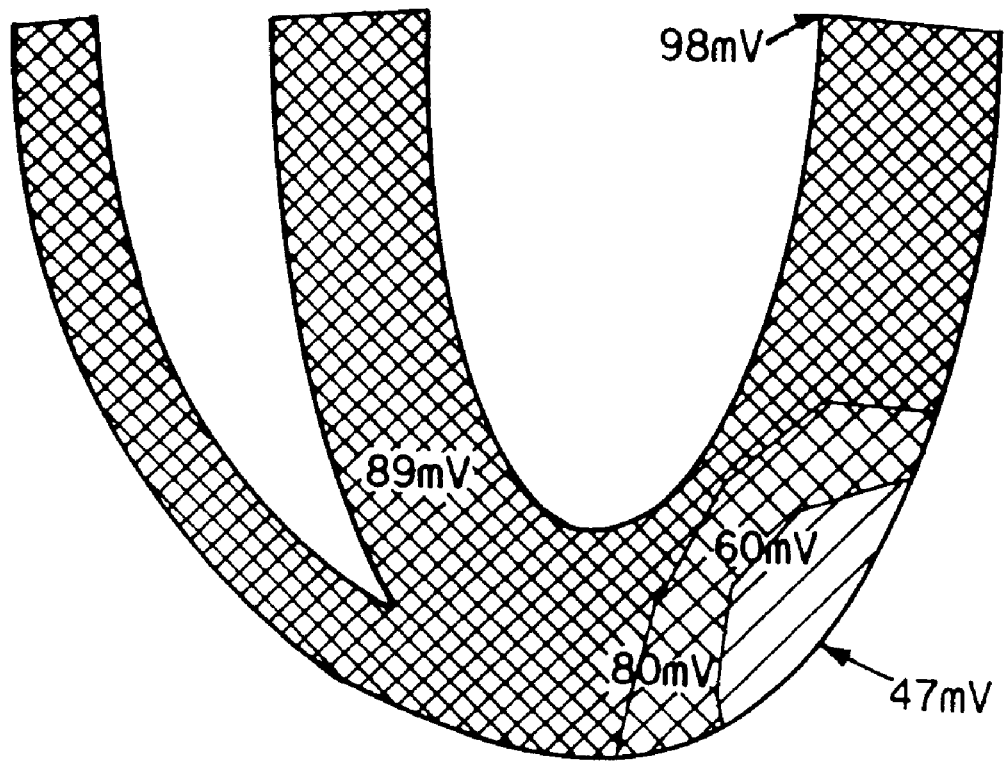
FIG. 28 is an image represented by a monitor or printer in the third display example.

The CPU 120 executes processing shown in FIG. 28, as that corresponding to Step S104 in FIG. 16. This processing includes selecting desired type of a myocardial electroaction amount (Step S104i), producing density image data indicative of a selected type of myocardial electroaction amount (Step S104j), producing edge data of a ventricular cross section (Step S104k), producing data of local minimum and maximum values of a selected type of myocardial electroaction amount (Step S104l), and preparing data to be displayed (Step S104m).

At Step S104i, one type of myocardial electroaction amount is selected via the operation panel 117 to which an operator gives. Such amount is one of an action potential amplitude, conductance, current dipole density which is multiplication of the conductance and the action potential amplitude, or another amount reflected by myocardial electrophysiological actions.

Assume that an action potential amplitude is selected as such myocardial electroaction amount, for example. In response to this selection, two-dimensionally distributed data of action potential amplitudes which have been analyzed by processing at Step S103 in FIG. 16 are taken into a working area of the memories. At the next Step S104j, density image data of the amplitudes are produced. This production is performed by the same processing as in a colored gradation image of excitation onset times (Step S104f) described in the foregoing second display example. Replacing the colors Ci by densities and distinguishing action potential amplitudes based on its quantities Vi are enough. (Potential amplitudes Vi . . . $V_g$ are substituted for the above-mentioned time instants Ti . . . $T_g$.)

After this, local minimum and maximum values and their positions in the action potential amplitude distribution are calculated (Step S104*l*), like the forgoing processing at Step S104*c* in FIG. 18. Data to be displayed are then prepared at Step S104*m* such that the data obtained at Steps S104*i* to S104*l* are synthesized, graphic data of arrows showing the local minimum and maximum values are added, and data of figures representing action potential amplitudes are as indices added to several positions on the ventricular cross section.

An image displayed by the monitor 115 and/or a printed figure provided by the printer 116 through the foregoing processing are exemplified in FI. 28. On an edge image of a ventricular cross section, action potential amplitudes are superposed as its density image and the positions of its local minimum and maximum value points are shown by arrows with figures expressing the values. Additionally, figures expressing as indices some of the action potential amplitudes are added at proper locations. Because of visualizing action potential amplitudes employed as the myocardial electroaction amount, diagnosis can be performed with a superior visibility performance and quantitative understanding of the analyzed results becomes more easier than the congenital approaches.

Although the action potential amplitude has been described as one of the myocardial electroaction amounts in the above, other amounts, such as conductance values or current dipole densities, can be displayed in the same manner. Moreover, instead of the density image, the myocardial electroaction amount can be expressed using a gradation image of colors (hues), a brightness-changed image of a specific hue, or an edge line chart mutually connecting distribution points where values of a myocardial electroaction amount are the same.

Fourth Display Example

A fourth example of display will be described. While the foregoing first to third display examples are concerned with displaying solely either one of the propagated excitation process or myocardial electroaction amount, the fourth display example provides a configuration by which data of a propagated excitation process and myocardial electroaction amount are concurrently displayed by a single display means.

Figure 29:
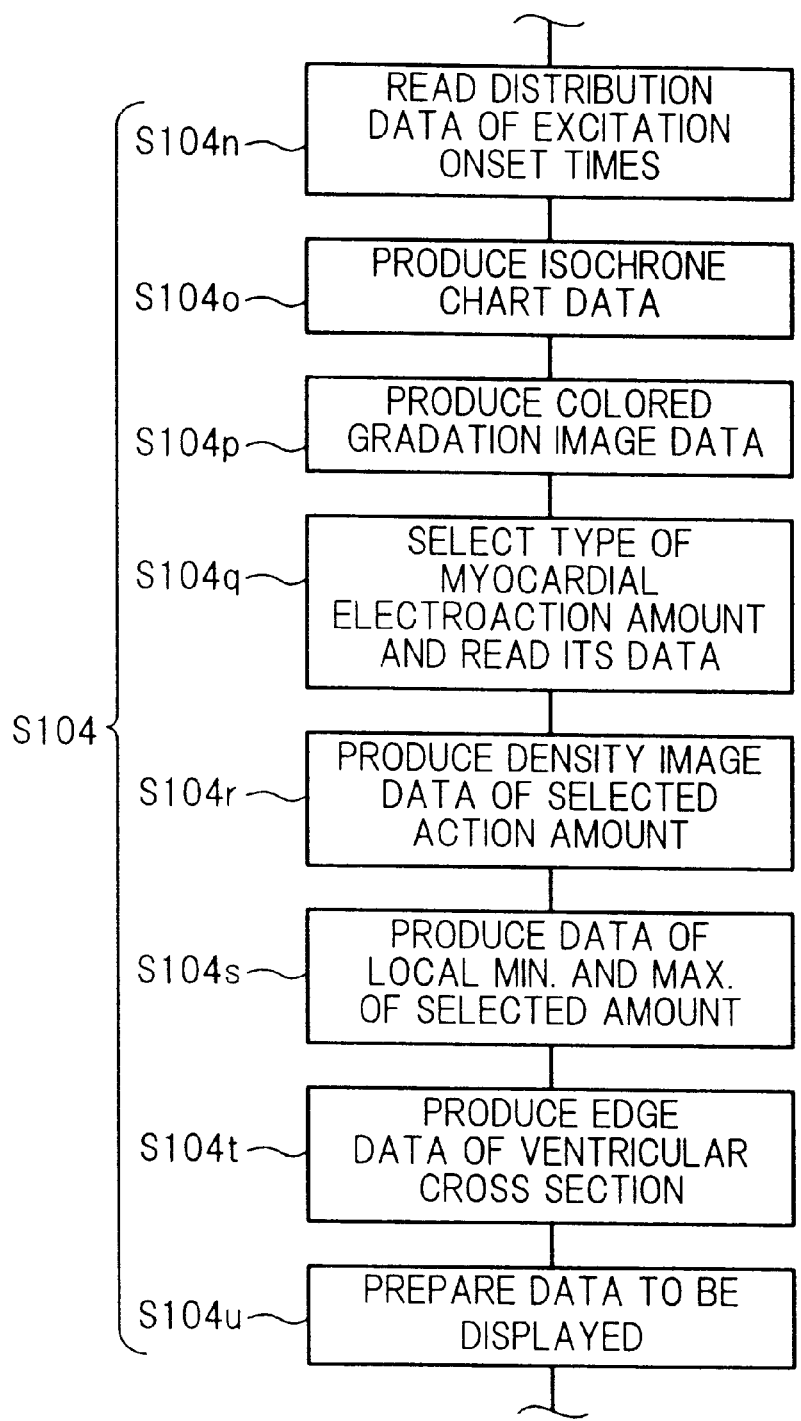
FIG. 29 is a flowchart for producing image data to be displayed in a fourth display example of the fifth embodiment.

The CPU 120 executes processing shown in FIG. 29 correspondingly to the process of Step S104 in FIG. 16. Steps S104*n* to S104 *p* are for handling distribution data of excitation onset times, in which the distribution data are read from the memories, formed into isochrone chart data, and converted into gradation image data of colors (hues). This processing is th e same in contents as the foregoing steps S104*e* and S104*f* in FIG. 24. On the other hand, Steps S104*q* and S104*s* are responsible for distribution data of the myocardial electroaction amount. Distribution data of action potential amplitudes are selected as the amount, and read from the memories. Data to be displayed are prepared which represent the read distribution data as a density image, and data showing local minimum and maximum values of the amplitudes are produced with the manner described before (refer to FIG. 27). Edge data of a ventricular cross section are produced at Step S104*t*, before the data thus-produced so far are synthesized into frame data to be displayed. In this synthesis, the CPU 120 superposes on the ventricular cross section data not only the produced data of the excitation onset time distribution but also the produced data of the action potential amplitude distribution, and processes both the two sets of superposed data such that they are in a parallel, right/left-divided arrangement in an image to be displayed.

Figure 30:
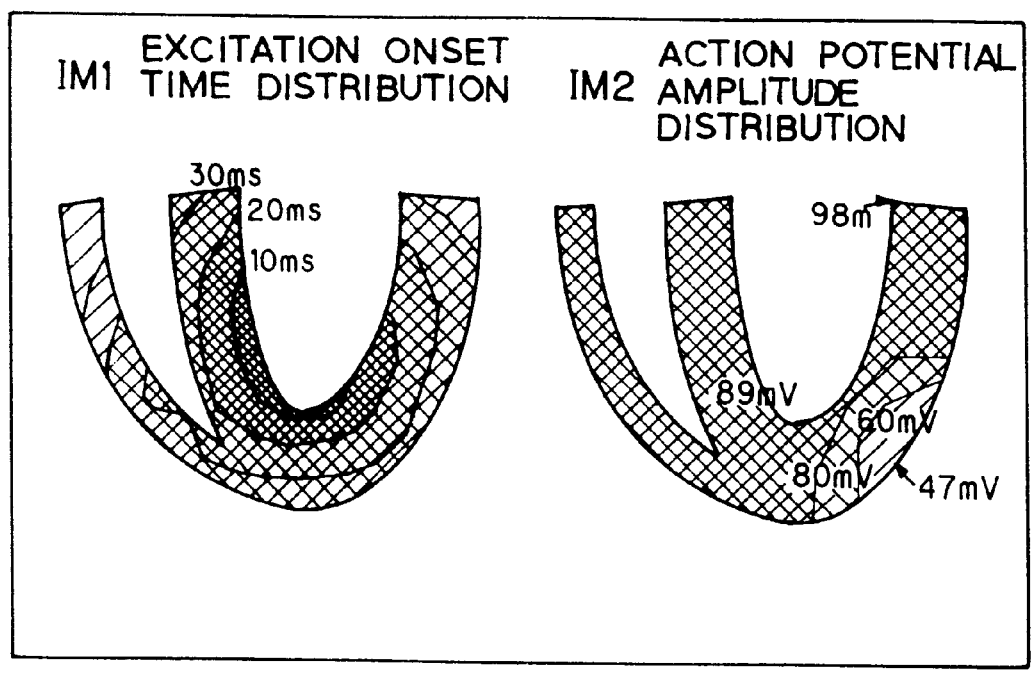
FIG. 30 is an image represented by a monitor or printer in the fourth display example.

The data to be displayed are sent to the monitor 115 and/or printer 116 (FIG. 16, Step S105), providing an image as shown in FIG. 30. The image is thus shown on the same screen of the same displaying means. The image is composed of a first image IM1 and a second image IM2 in a divided mode; in the first image IM1, distribution data of excitation onset times are superposed as a colored graduation image and an isochrone chart on a ventricular cross section image, and in the second image IM2, distribution data of action potential amplitudes (one of the myocardial electroaction amounts) are superposed as a density image on the same ventricular section image as the first image IM1.

As can be seen from this divided displayed image example, the left ventricular apex has a region whose action potential amplitude is lowered. It is possible to readily recognize that there is something wrong in the region.

In addition to various advantages that have been described in the first to third display examples, the fourth display example has the following advantages. First, the diagnostic system can be applied to a wide range of cardiac diseases, such as various kinds of dysrhythmia accompanying abnormalities in conducting excitation, and myocardial ischemia and myocardial infraction both accompanying abnormalities in action potential, because both the excitation onset time distribution and the action potential amplitude distribution are displayed concurrently by a single displaying means. Further, differently from the conventional current source density distribution display technique that a plurality of images or charts are used to represent temporal changes in current course distributions, the fourth display example enables reading of information about temporal changes from a single image of the excitation onset time distribution. Hence, it is possible to greatly reduce the number of images necessary for diagnosing a variety of cardiac diseases. There is an advantage that remarkably reduces handling and labor for interpretation.

In the above fourth display example, as the myocardial electroaction amount, the action potential amplitude can be replaced by conductance or current dipole density. Additionally, the first image IM1 concerning the excitation onset time distribution positioned left in FIG. 30 can be displayed as a density image or a brightness-modulated image, while the second image IM2 of the myocardial electroaction amount distribution positioned right can be presented by a color-gradated image or a brightness-modulated image, thus enriching display modes.

Sixth Embodiment

Figure 31:
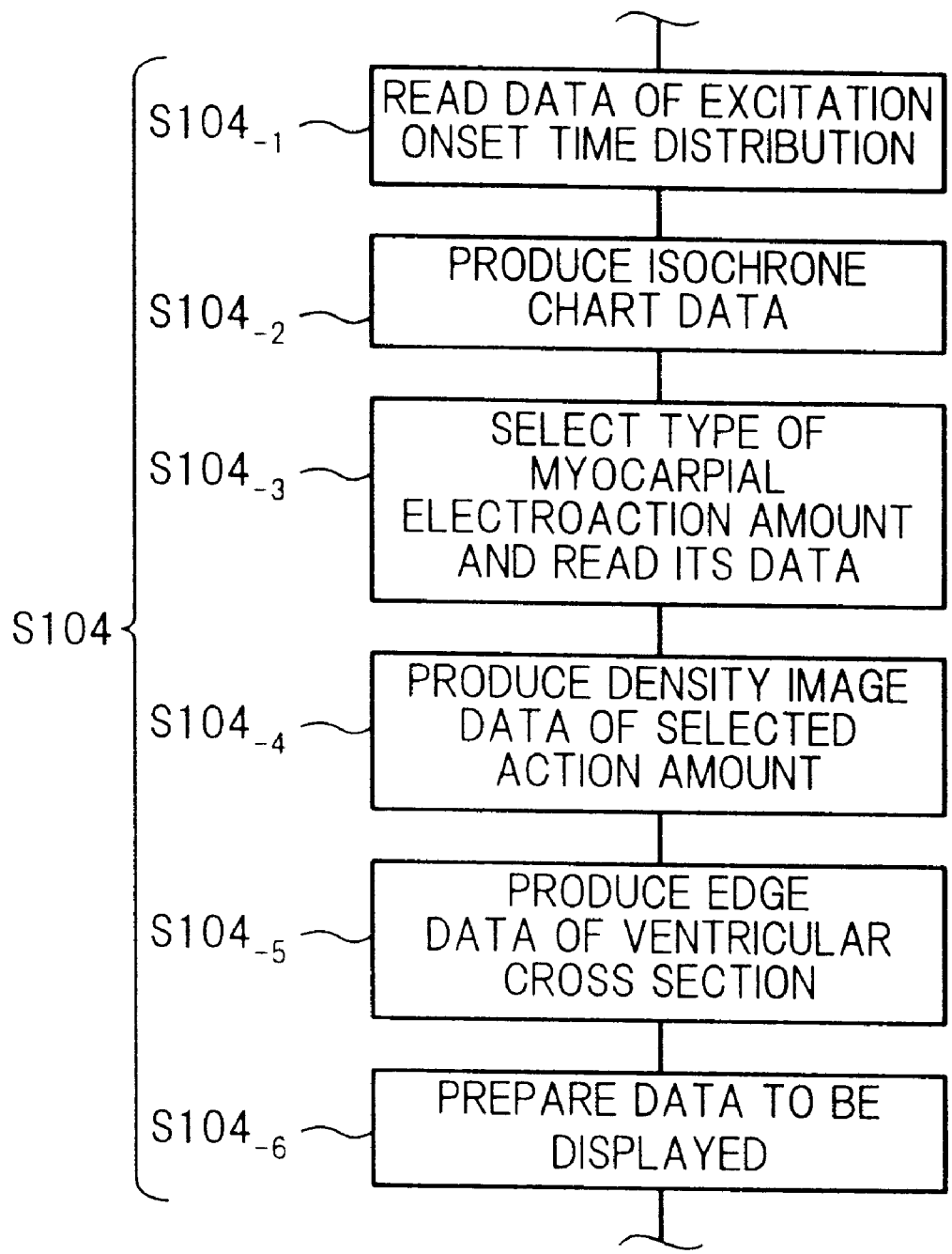
FIG. 31 is a flowchart for producing image data to be displayed in a sixth embodiment according to the present invention.
Figure 32:
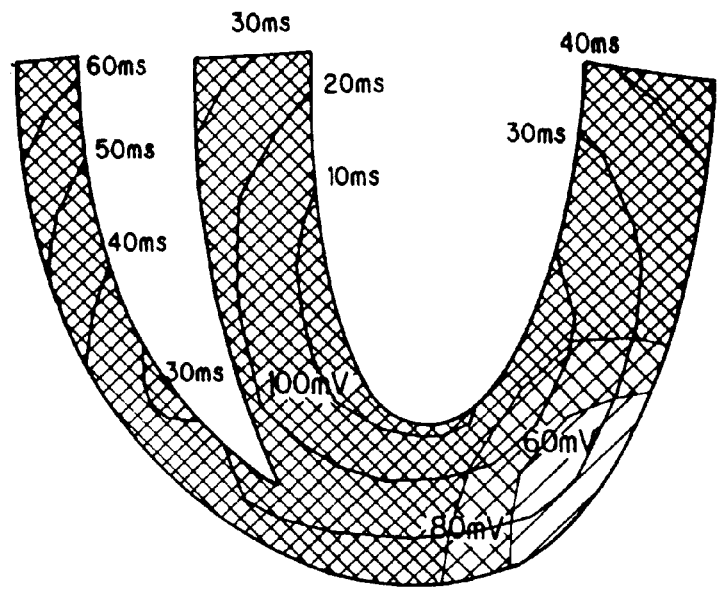
FIG. 32 is an image represented by a monitor or printer in the sixth embodiment.

Referring to FIGS. 31 and 32, a sixth embodiment of the present invention will be described. The display performed in this embodiment has a feature that distributions of both excitation onset times and a myocardial electroaction amount are presented with a single display screen.

The hardware of the entity diagnostic system is configured in the same as the first embodiment.

The CPU 120 performs processing, like the one in FIG. 16, where excitation onset times and a myocardial electroaction amount are analyzed, their distribution data are calculated, and processing shown in FIG. 31 is performed at Step corresponding to production of data to be displayed. As shown in the figure, the CPU 120 produces isochrone chart data of an excitation onset time distribution (Steps S104-1, 2), select an action potential amplitude as one amount of the myocardial electroaction amounts (Step S104-3), and produces density data of its selected amount (Step S104-4). Then the CPU produces edge data of a cross section of the ventricles along its major axis (Step S104-5). These successive procedures are the same or similar as or to those in FIG. 29.

The CPU 120 then executes preparation of data to be displayed (Step S104-6). In this preparation, the edge data of the ventricular shape, the isochrone chart data of the excitation onset time distribution, and the density image data of the action potential amplitude distribution are superposed one on another with their positions matched, providing synthesized frame image data. Figures expressing propagated times are also graphically written at places for each isochrone in the chart, and figures expressing action potential are also graphically written at places for each area in the density image.

The data to be displayed are thus-prepared and sent to the monitor 115 and/or printer 116 (FIG. 16, Step S105), providing an image shown in FIG. 32. On a single image depicting the ventricular major-axis cross section, the isochrone chart of the excitation onset time distribution and the density image of the action potential amplitude are displayed in a superposition fashion.

According to the embodiment, besides the advantages acquired by the forgoing fourth display, several other advantages are provided. Because both the excitation onset time distribution and the action potential amplitude distribution are visualized as one image, a screen space for display can be saved. Therefore, as one manner to present analyzed results, it is possible to provide a single display screen on which a plurality of different ventricular cross sections are placed, each of which are formed by mutually superposing an excitation onset time distribution and an action potential amplitude distribution, like FIG. 32. This can avoid the display screen from being scrolled, reducing operational handing and labor when a plurality of ventricular cross sections should be displayed. Also work for interpreting them can be relieved. Efficiencies in operation and interpretation can be improved. Furthermore, thanks to providing doctors enough time to deeply observe one screen, interpretation accuracy can be improved.

Furthermore, since both the excitation onset time distribution and the action potential amplitude distribution are mutually superposed-displayed, correspondence between them can readily be read from the displayed image. For example, it is an excitation onset time corresponding to an abnormal region in the action potential amplitude distribution, an excitation wavefront shape in the abnormal region, or others. This contributes to higher accuracy in interpretation and diagnosis, also contributing to higher reliability.

Figure 33:
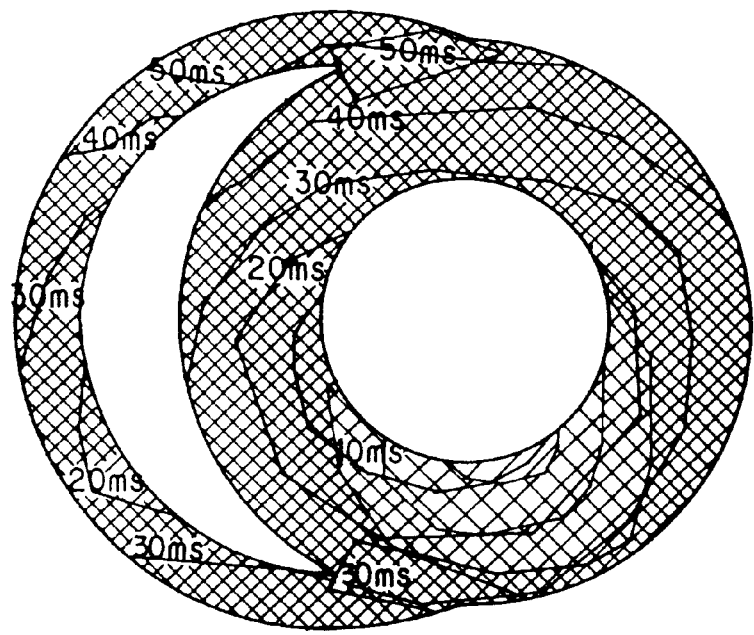
FIG. 33 is another image represented by a monitor or printer according to an alternative example of the sixth embodiment.

Shapes of the ventricular cross section on which the foregoing two types of electrophysiological phenomena are superposedly displayed is not limited to the major-axis cross section shown in FIG. 32. For instance, producing data of a cross section at a desired position in the Y-axis of the ventricles at Steps S104-2, -4, and -5 in FIG. 31 can display an image of the two types of phenomena superposed on a minor-axis cross section cut at the desired ventricular position. One such example is shown in FIG. 33, which provides the equivalent operation and advantages to those described and accomplishes enrichment of setting of vernacular sections.

Seventh Embodiment

Figure 34:
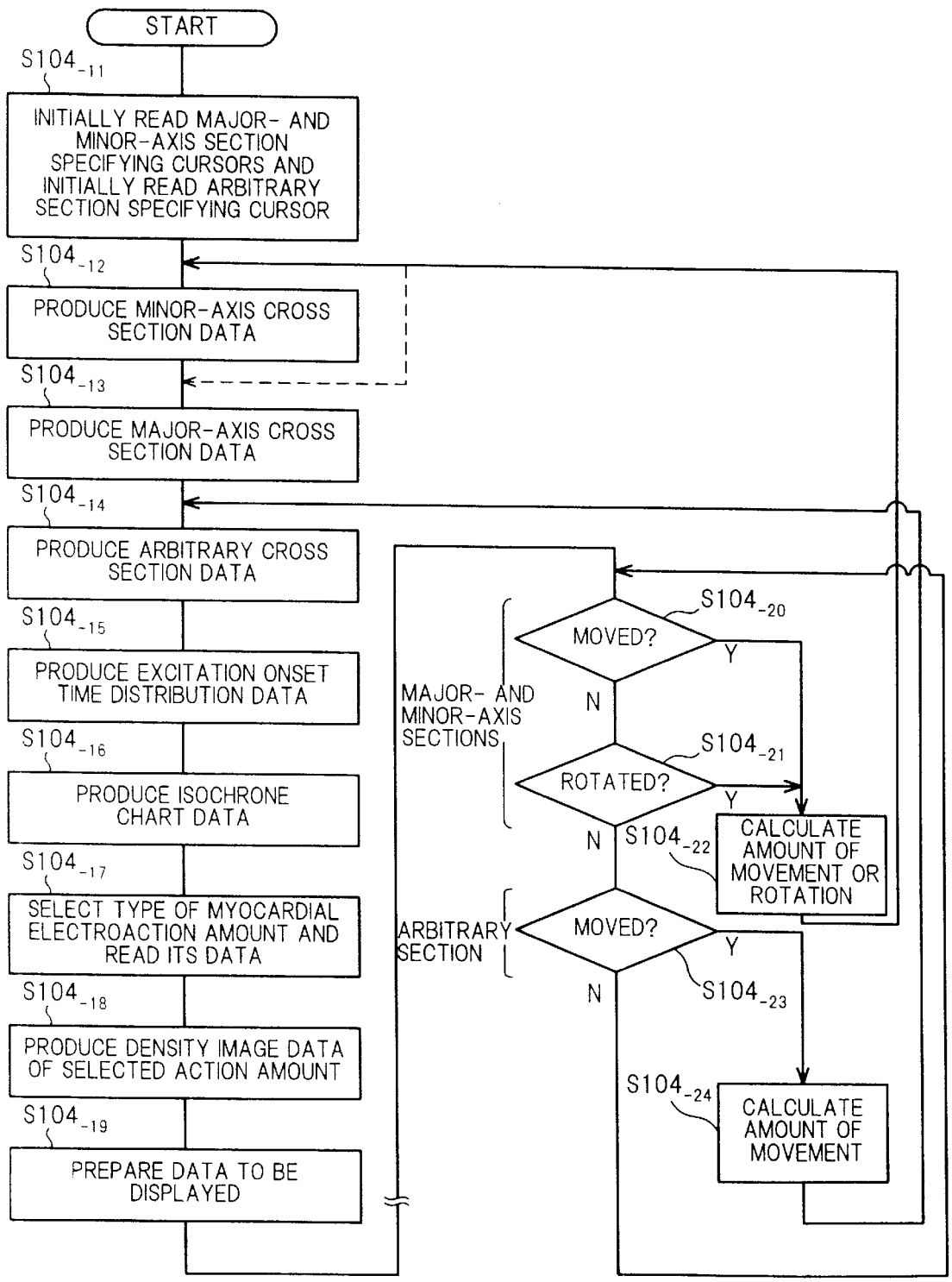
FIG. 34 is a flowchart for producing image data to be displayed in a seventh embodiment according to the present invention.
Figure 35:
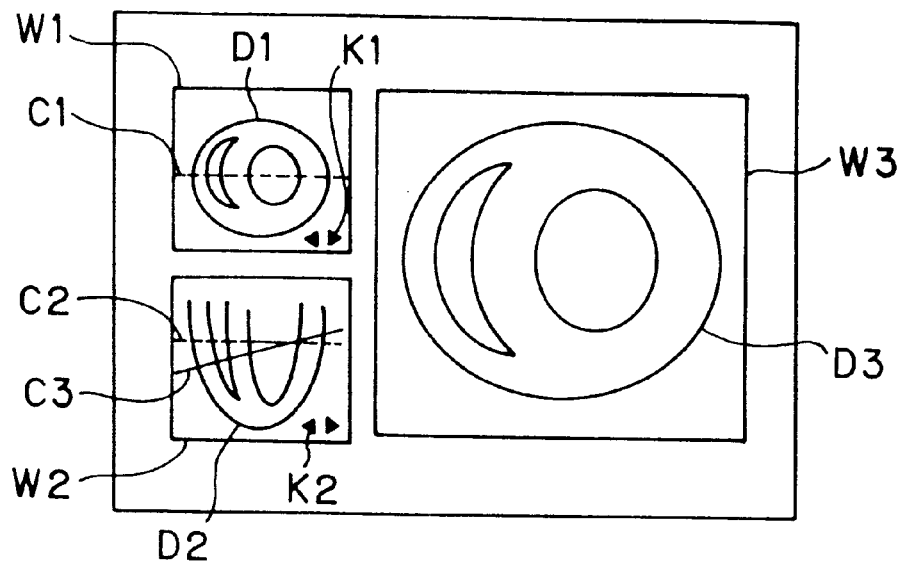
FIG. 35 is a displayed illustration of a monitor screen in the seventh embodiment.
Figure 36:
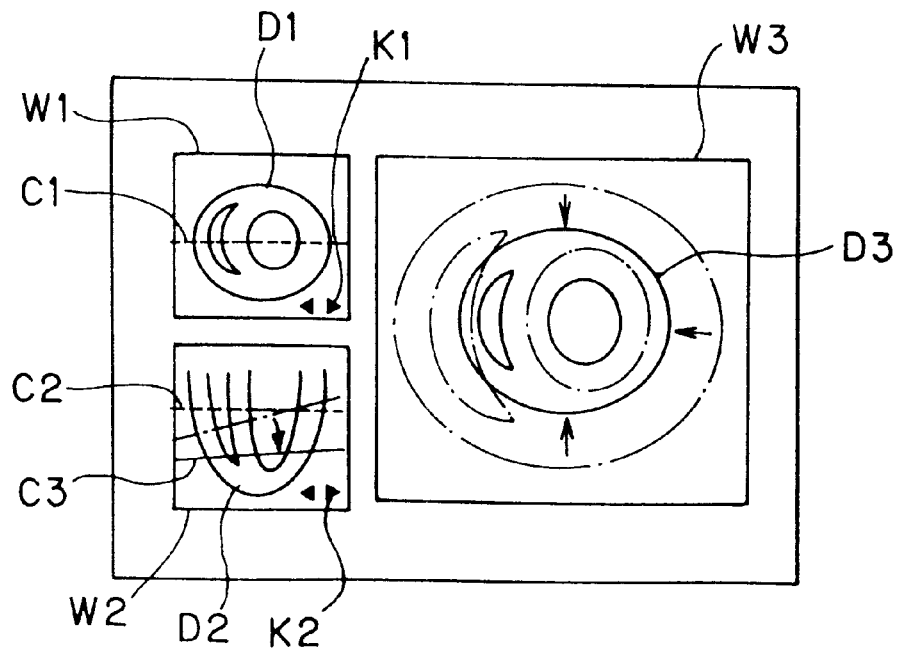
FIG. 36 is another displayed illustration of a monitor screen in the seventh embodiment.
Figure 37:
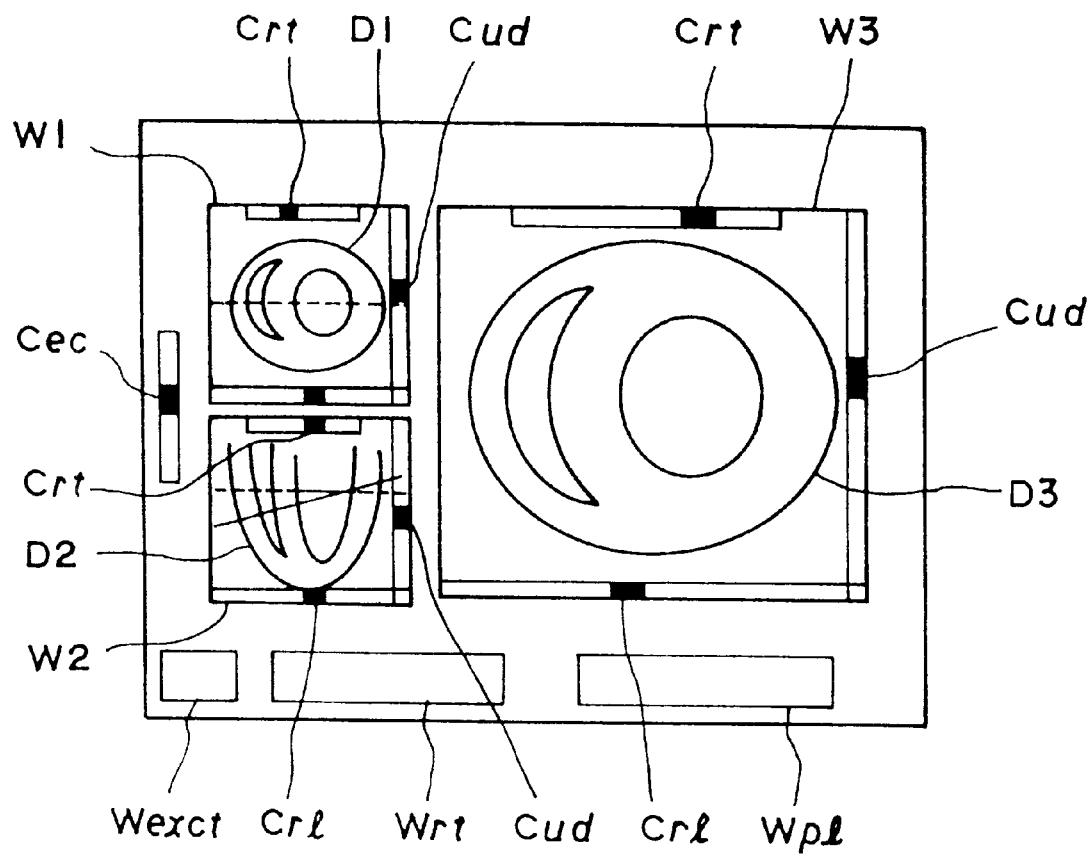
FIG. 37 is a display screen showing an alternative example according to the seventh embodiment.

Referring to FIGS. 34 to 36, a seventh embodiment of the present invention will now be described. The hardware construction of the diagnostic system is the same or similar as or to that described so far, thus its explanation will be omitted or simplified. This manner will also be adopted in the embodiments following the seventh embodiment.

A feature of this embodiment is to not only display both an excitation onset time distribution and an myocardial electroaction amount, which are inherent to a ventricular cross section, on its cross section with a single screen but also desiredly select the ventricular cross section.

In this embodiment, three windows W1, W2 and W3 are set as displaying regions on the screen of the monitor 115, as shown in FIG. 35, and ventricular cross sections cut at different sectional positions are individually displayed in the windows. An arbitrary cross section is finally decided through interactive operation with an operator, and an excitation onset time distribution and a myocardial electroaction amount, which are inherent to the decided ventricular cross section, are displayed on the section in a superposition manner.

Practical processing executed by the CPU 120 is shown, which is done at Step S105 of FIG. 16 described before. First, initial values for cursors are read from the memories; the cursors consist of cursors specifying the cut positions of ventricular major- and minor-axis cross sections (hereinafter referred to as "major-axis and minor-axis section specifying cursor" and a cursor specifying a cut position of a finally-desired cross section at arbitrary positions (hereinafter referred to as "arbitrary section specifying cursor") (Step S104-11 in FIG. 34).

The major-axis and minor-axis section specifying cursors C1 and C2 are displayed dotted lines, as shown in FIG. 35. The initial positions to be displayed of the cursors C1 and C2 are predetermined at given positions that cause typical major-axis and minor-axis cross sections to be shown in the individual windows. As shown in FIG. 35, the arbitrary section specifying cursor C3 is displayed as a solid line. The initially displayed position of the cursor C3 is predetermined so that it is displayed on the major-axis cross section upward-obliquely as it goes right.

The CPU 120 produces edge data of a minor-axis cross section and a major-axis cross section based on the initial potions of the cursors C1 an C2 (Step S104-12 and -13). Then it produces edge data of an arbitrary cross section defined by the initial position of the cursor C3 (Step S104-14). These edge data are produced with the same manner as that described before.

After this, distribution data of excitation onset times are read, and isochrone chart data are produced from the distribution data (Steps S104-15 and -16). A type of the myocardial electroaction amount is selected, and its distribution data are read (Step S104-17). For example, distribution data of an action potential amplitude are read. Further data of a density image for the read distribution data are produced (Step S104-18). The processing for these data to be superposed are the same or similar as or to that described before.

The processing is now passed to preparation of data to be displayed (Step S104-19). The preparation is as follows. First, as shown in FIGS. 35 and 36, the first and second windows W1 and W2 of which displaying areas are relatively small are located at the left-side upper and lower positions in the monitor screen, respectively, while the third window W3 of which displaying is larger than the first and second ones is located at the right side. Further, located in the first window W1 are data of the minor-axis cross section D1 on which the major-axis section specifying cursor C1 and a rotation specifying button K1. In contrast, located in the second window W2 are data of the major-axis cross section D2 on which the minor-axis section specifying cursor C2 and an alternative rotation specifying button K2. In the third window W3, located are image data in which the isochrone chart data of the excitation onset times and density image data of the action potential amplitude are superposed on the arbitrary cross section.

The data thus-prepared are initially displayed on the monitor 115 (FIG. 15, Step S105). One such displayed example is in FIG. 35.

As viewing the monitor screen, an operator adjusts the positions of the cursors C1 to C3 by operating a mouse etc. in an interactive manner. To responsible for this operation, the CPU 120 further executes processing after Steps S104-20 in FIG. 34.

The CPU 120 reads the positions of the major- and minor-axis section specifying cursors C1 and C2, and determines whether or not at least one of the cursors is in motion (Step S104-20). The cursors C1 and C2 are operated to modify the cut positions of the major- and minor-axis cross sections.

If NO at this determination, that is, where both the cursors C1 and C2 are not in motion, whether or not the rotation specifying buttons k1 and K2 are under operation is then determined (Step S104-21). The buttons K1 and K2 are operated to set the displayed ventricular cross sections at desired angles by individually rotating them in the window W1 and W2 directions in an interactive manner. If NO at this determination, the arbitrary section specifying cursor C3 will be investigated.

However, where the determination is YES at either of Steps S104-20 or -21, an amount associated with the cursor movement or rotation is calculated (Step S104-22). The processing is then returned to Step S104-12 or S104-13, being subjected to reproduction of edge data of minor- or major-axis cross section at a new cut position where the newly calculated moved or rotated position is considered. Responsively to the reproduction, a spatial relationship is brought about between the position of the cursor S3 which has been set so far and a newly produced cross section. Thus, under the new positional relationship, edge data of an arbitrary cross section based on the position specified by the cursor C3 are reproduced (Step S104-14). Likewise, the isochrone chart data of the excitation onset time distribution and the density image data of the action potential amplitude distribution are calculated, and superposedly displayed on the updated arbitrary cross section. Namely the images in the window W3 are updated.

On one hand, if NO at Step S104-21, it is determined if the arbitrary section specifying cursor C3 has been moved (Step S104-23). If NO at the step, the cut position of the arbitrary cross section has not been changed, returning to Step S104-20 to repeat the forgoing processing. However, in the case of YES at Step S104-23, an amount associated with the cursor movement is calculated (Step S104-24). The processing is then returned to Step S104-14 in order to reproduce edge data of a new arbitrary cross section at a new cut position considering the amount of movement or rotation newly calculated. Likewise, the isochrone chart data of the excitation onset time distribution and the density image data of the action potential amplitude distribution are calculated, and superposedly displayed on the updated arbitrary cross section. Namely the images in the window W3 are further updated.

In consequence, a minor-axis cross section at a position of the cursor C2 specified by an operator into the window W2 at the lower left of the monitor screen is displayed in the upper-left window W1. On the contrary, a major-axis cross section at a position of the cursor C1 specified by an operator into the window W21 at the upper left of the monitor screen is displayed in the lower-left window W2. Because the cursors C1 and C2 can be moved freely on the screen in an interactive mode, the major- and minor-axis cross sections for specifying the position of an arbitrary cross section can be fist adjusted in position. Further, ventricles to be displayed can be rotated in each window W1 (W2) in the displayed plane direction using an interactive fashion, and adjusted in angle. Using this ventricle rotation and cursor movement, an operator is able to display the major- and minor-axis cross sections in desired attitudes.

After this preliminary section display and its adjustment, the operator is to set the position of the arbitrary section specifying cursor C3 at a desired position in the lower-left window W2, for example. In response to this, edge data of the arbitrary cross section are calculated, and its cross section is displayed in the right window W3 (displaying area for arbitrary cross section). Every time when the cursor C3 is moved, the arbitrary cross section is updated and displayed in the window W3. For example, as shown in FIG. 36, changing the cursor C3 from the chain line position to the solid line position allows the arbitrary cross section D3 to responsively change from the chain line position to the solid line position in real time. The cursor C3 may be specified and positionally-changed in the upper-left window W1 of the monitor.

Therefore, operating the cursors etc. C1, C2, K1 and K2 to rotate and move the ventricles and adjusting the cursor C3 permits a cross section at any position to be displayed in the right area of the monitor. Although omitted in FIGS. 35 and 36, an excitation onset time distribution and an action potential amplitude distribution are superposedly displayed on the arbitrary cross section D3.

By way of example, data to superposedly displayed on the arbitrary cross section D3 may be either one of an excitation onset time distribution and an action potential amplitude distribution. Further, an excitation onset time distribution, an action potential amplitude distribution, or both the distributions may be superposedly displayed on at least one of the major- and minor-axis cross sections in response to operator's selection commands.

According to this embodiment, the analyzed results of intracardiac electrophysiological phenomena can be visualized on any cross section, enabling a quick and easy examination for various regions of the ventricles.

An alternative example for specifying the foregoing arbitrary cross section is provided as in FIG. 35. The data processing for this example is executed by the CPU 120.

Practically, as shown in FIG. 35, three windows W1, W2 and W3 are placed on the upper-left, lower-left, and right areas on the screen, like the above. A rotation cursor $C_{rt}$ is placed at a upper end of each window. Sliding the cursor $C_{rt}$ in the right and left direction makes it possible to modify a displayed rotation angle of the ventricles. At a screen left side position, an enlargement/reduction cursor $C_{ec}$ is placed commonly to the three windows W1, W2 and W3. Sliding this cursor $C_{ec}$ in the vertical direction makes it possible to simultaneously alter the size of the ventricles displayed in each window. Parallel-moving cursor $C_{ud}$ and $C_{rl}$ are placed at the right and lower sides in each window. Operating these cursors makes it possible to positions of the ventricles displayed in the windows in the right and left directions and the verticle directions. The parallel movement in the right and left direction in the left-side windows W1 and W2 is commonly specified from the cursor $C_{rl}$ set in one window W2.

At the lower left corner in the screen, placed is a window $W_{exct}$ for displaying and setting an enlargement/reduction amount. This amount is expressed by percent when displaying the ventricles in each window, or expressed by a unit of length, such as millimeters, for displaying sizes corresponding to the heights of the windows. When an operator gives values into the window $W_{exct}$ can specify or change the enlargement/reduction amount. Further, a window $W_{rt}$ is placed next to the window $W_{exct}$ for displaying and setting a rotation angle of the ventricles, which is expressed by degrees. Giving values into this window $W_{rt}$ from an operator enables the specification and/or change of the rotation angle. At the lower right corner in the screen, placed is a window $W_{pl}$ for displaying and setting a parallel moving amount of the ventricles, which is expressed by a unit of millimeters. When an operator provides this window $W_{pl}$ values, the parallel moving amount can be specified and changed.

Properly combining the above setting and changing operation allows an operator to face to the monitor screen in an interactive fashion. Thus arbitrary cross sections can be specified toward the ventricles. Like the foregoing embodiment, a two-dimensional distribution image concerning intracardiac electrophysiological phenomena inherent to a specified cross section can be superposedly displayed on the specified cross section. Particularly, detailed specification, such as the rotation angle, parallel moving amount, and enlargement/reduction amount, can be given, increasing accuracy in specifying the section positions.

Eighth Embodiment

Refereeing to FIGS. 38 to 39, an eighth embodiment of the present invention will be described. The embodiment provides a display technique by which a perspective projected view of a ventricular model is produced along a changeable viewing direction and at least one of an excitation onset time distribution and a myocardial electroaction amount inherent to the surface of the perspective projected view is superposedly displayed on the surface.

Figure 39:
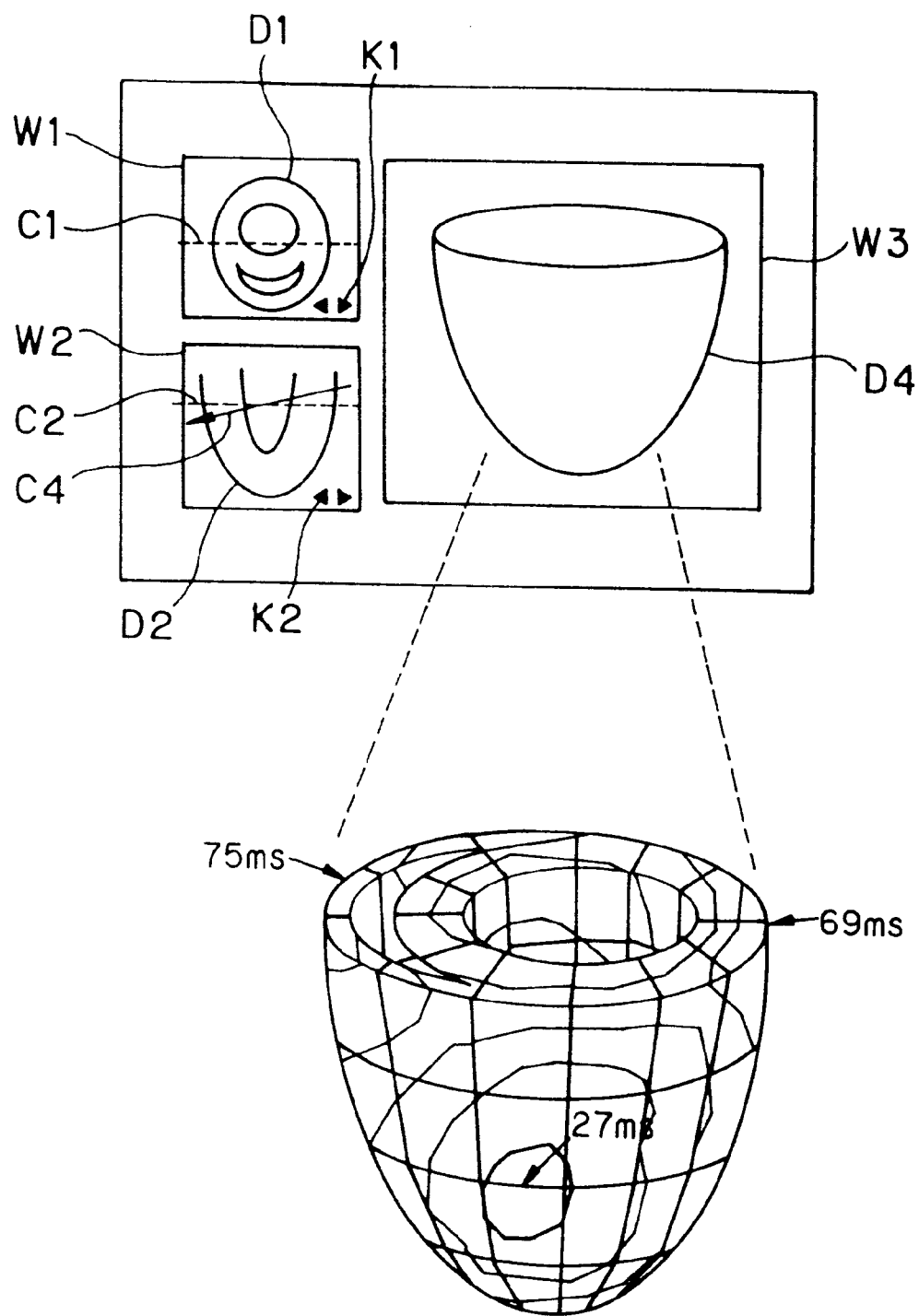
FIG. 39 pictorially shows an image displayed in the eighth embodiment.

According to this embodiment, as shown in FIG. 39, three windows W1, W2 and W3 are placed on the monitor screen, and ventricular minor-axis sectional, major-axis sectional, and perspective projected views are displayed in the windows, respectively. A perspective projected view is then determined through interaction with an operator, and on the frontal surface of the perspective projected view, at least one of an excitation onset time distribution and a myocardial electroaction amount characteristic of the frontal surface are superposed.

Figure 38:
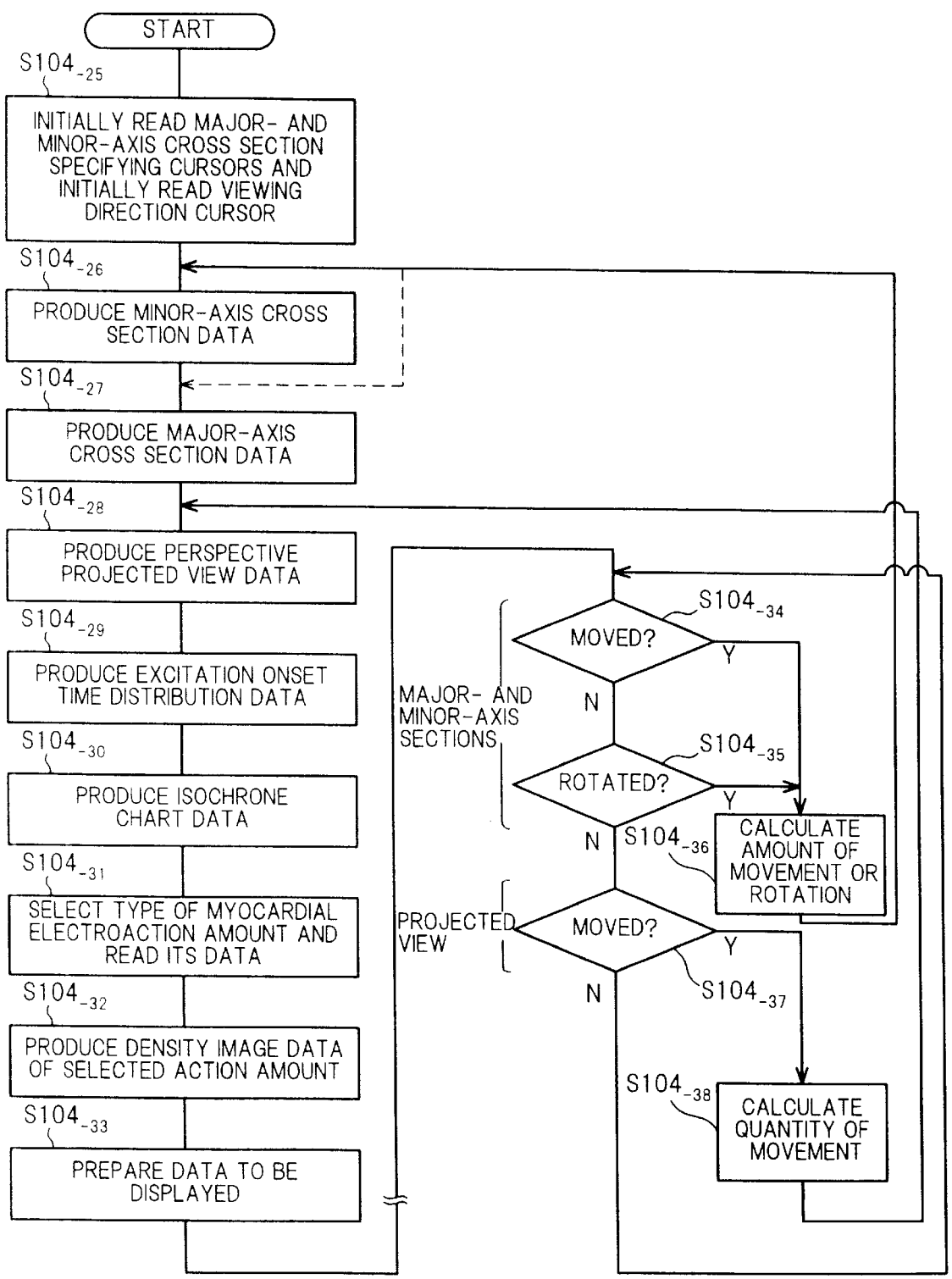
FIG. 38 is a flowchart for producing image data to be displayed in an eight embodiment according to the present invention.

The CPU executes processing shown in FIG. 38, corresponding to Step S105 in FIG. 16. described before. First, read from the memories are initial values of cursors including major- and minor-axis section specifying cursors to specify cut positions of ventricular major-axis and minor-axis cross sections and a cursor to specify a viewing direction of a perspective projected view for a finally desired ventricular shape (hereinafter, referred to as viewing direction cursor) (FIG. 38, Step S104-25).

The major-axis section specifying cursor C1 and the minor-axis section specifying cursor C2 are visualized by chain lines, as in FIG. 39. The initial positions of the cursors C1 and C2 are reset so as to bring major- and minor-axis cross sections in their typical states. The viewing direction cursor C4 is visualized by a solid line arrow, as shown in FIG. 39, where the direction of the arrow expresses a viewing direction. The initial position of the cursor C4 is predetermined to have a given angle increasing as it goes to the right on, for example, the major-axis cross section. Of course the cursor C4 may be put on the minor-axis cross section.

The CPU 120 produces edge data of the minor- and major-axis cross section correspondingly to the initial positions of the cursors C1 and C2 in the same manner described before (Step S104-26 and -27). And, it produces edge data of a ventricular perspective projected view along the viewing direction defined by the initial position of the cursor C4 with known methods (Step S104-28).

After this, the CPU reads distribution data of excitation onset times, and produces isochrone chart data from the read distribution data (Step S104-29 and -30). The CPU determines which type of myocardial electroaction amount should be selected, and reads distribution data of the selected amount (Step S104-31). By this processing, as an example, distribution data of an action potential amplitude are stored into a working area of the memories. Further, the CPU produces density image data of the distribution data of the selected amount (Step S104-32). These steps are carried out by the same way as that in the foregoing embodiments.

Then, data to be displayed is prepared (Step S104-33). The preparation processing is as follows. First of all, a first and second windows W1 and W2 whose displayed areas are rather small are allocated to upper and lower left portions in the monitor screen, while a third window W3 whose displayed area is larger than the first and second ones is allocated to a right potion. In the first window W1, data of a minor-axis cross section D1 on which a major-axis section specifying cursor C1 and a rotation specifying button K1 are superposed are arranged. On one hand, in the second window W2, data of a major-axis cross section D2 on which a minor-axis section specifying cursor C2 and a rotation specifying button K2 are superposed are arranged. In the third window W3, image data in which at least one of isochrone chart data of excitation onset times and density image data of action potential amplitudes are superposed on a surface of the calculated ventricular perspective projected view are arranged.

The data to be displayed thus-prepared are initially displayed by the monitor 115 (FIG. 16, Step S105). One example of the display is shown in FIG. 39.

Viewing the displayed image, an operator is to interactively adjust the positions of the cursors C1, C2 and C4. For this adjustment, the CPU 120 executes processing appearing after Steps S104-34 in FIG. 34.

The CPU 120 reads the positions of the major- and minor-axis section specifying cursors C1 and C2, and determines whether at least one of them is in motion or not (Step S104-34). The cursors C1 and C2 are operated to alter the cut positions of the major- and minor-axis cross sections.

If NO at this determination, that is, where both the cursors C1 and C2 are not in motion, whether or not the rotation specifying buttons k1 and K2 are under operation is then determined (Step S104-35). The buttons K1 and K2 are operated to set the displayed ventricular cross sections at desired angles by interactively individually rotating them in the windows W1 and W2. If NO at this determination, the viewing direction cursor C4 will be investigated.

However, where the determination is YES at either of Steps S104-34 or -35, an amount associated with the cursor movement or rotation is calculated (Step S104-36). The processing is then returned to Step S104-26 or S104-27, being subjected to reproduction of edge data of minor- or major-axis cross section at a new cut position where the newly calculated moved or rotated position is considered. Responsively to the reproduction, a spatial relationship is brought about between the position of the viewing direction cursor S4 which has been set so far and a newly produced cross section (for example, a major-axis cross section). Thus, under the new positional relationship, edge data of a perspective projected view based on the position specified by the cursor C4 are reproduced (Step S104-28). Likewise, the isochrone chart data of the excitation onset time distribution and the density image data of the action potential amplitude distribution are calculated, and superposedly displayed on the updated perspective projected view. Namely the images in the window W3 are updated.

On one hand, if NO at Step S104-35, it is determined if the viewing direction cursor C4 has been moved (Step S104-37). If NO at the step, the viewing direction has not been changed, returning to Step S104-34 to repeat the forgoing processing. However, in the case of YES, an amount of changes in the viewing direction associated with the viewing direction cursor movement is calculated (Step S104-38). The processing is then returned to Step S104-28 in order to reproduce edge data of a new perspective projected view considering the calculated amount of changes in the viewing direction. Likewise, the isochrone chart data of the excitation onset time distribution and the density image data of the action potential amplitude distribution are calculated, and superposedly displayed on the updated perspective projected view. Namely the images in the window W3 are further updated.

In consequence, like the seventh embodiment, an operator is able to interactively display the major- and minor-axis cross sections at desired positions by operating the cursors C1, C2, K1 and K2. After this preliminary section display and its adjustment, the operator is to set the position of the viewing direction cursor C4 at a desired position in the lower-left window W2, for example. In response to this, edge data of a perspective projected view are calculated, and its view is displayed in the right window W3. Every time when the cursor C4 is moved, the viewing direction is updated, and the updated perspective projected view (or parallel projected view) is displayed in the window W3. In consequence, the direction of perspective projected view can be set and changed freely, and an excitation onset time distribution and an action potential amplitude distribution as the myocardial electroaction amount, which are taken from a surface of the ventricular model when viewed along the projected direction, can superposedly be displayed on the perspective projected view.

The viewing direction cursor C4 may be specified and positionally-changed on the minor-axis cross section displayed. Although only the isochrone chart of excitation onset times is superposed on the perspective projected view in FIG. 39, only an action potential amplitude distribution may be superposed, or both the quantities may be superposed. Further, an excitation onset time distribution, an action potential amplitude distribution, or both the distribution may be superposedly displayed on at least one of the major- and minor-axis cross sections in response to operator's selection commands.

According to this embodiment, an excitation onset time distribution and/or a myocardial electroaction amount distribution on the myocardial surface can be observed from a perspective projected view projected along any viewing direction. Thus, in addition to the advantages obtained from the fifth embodiment, myocardial ischemia portion on the epicardium is easier to be found out, contributing to a remarkable improvement for diagnostic performance.

In the forgoing seventh and eighth embodiments, a finally settled image in the third window W3 can be visualized by the printer 116.

Ninth Embodiment

Referring to FIGS. 40 to 41A, 41B, 41C and 41D, a ninth embodiment of the present invention will be described. A diagnostic system of this embodiment has a feature that at least one of an excitation onset time distribution and a myocardial electroaction amount distribution is superposedly displayed on a developed planar view of the ventricular surface.

Figure 40:
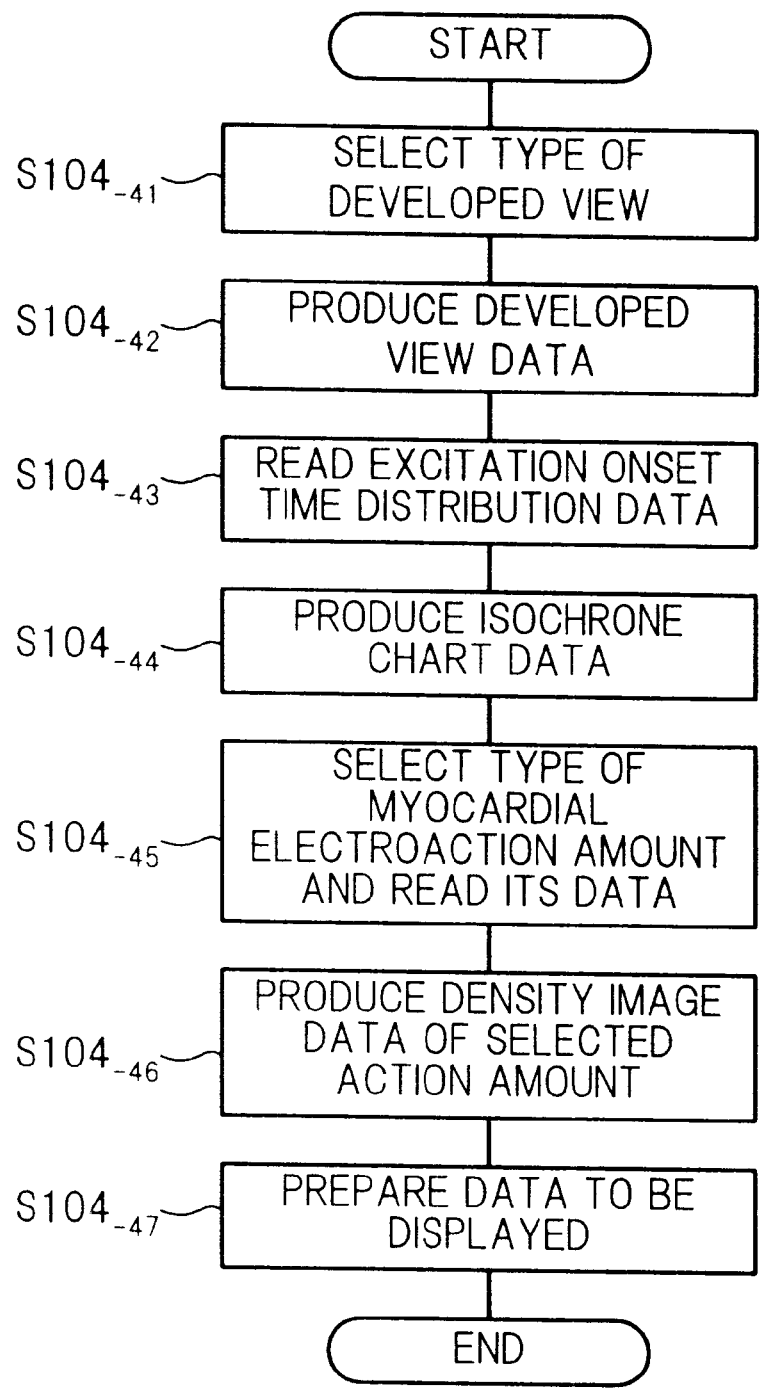
FIG. 40 is a flowchart for producing image data to be displayed in a ninth embodiment according to the present invention.

The CPU 120 executes processing shown in FIG. 40 in place of Step S104 in FIG. 16. Specifically, the CPU selects a type of a developed view of the ventricular surface (or cardiac surface) from a plurality of preset types (FIG. 40, Step S104-41). In this embodiment, by way of example, six types of developed views are preset, as shown in FIGS. 41A to 41F.

A circular developed view shown in FIG. 41A is one for an endocardium, where the center corresponds to the apex and the outer circumference to the cardiac base portion. Its upper side and lower side correspond to the anterior wall side and posterior wall side, respectively, while its right and left sides correspond to the left ventricle (L.V.) and right ventricle (R.V.), respectively. Another circular developed view shown in FIG. 41B is a developed view of the right ventricle endocardium, where the center expresses the topmost apex portion thereof. Its upper and lower sides correspond to the posterior and anterior wall sides, and its right and left sides correspond to the cardiac inner wall in the septum right ventricle side and the right ventricle free wall side, respectively. Another circular developed view shown in FIG. 41C is one for the left ventricle endocardium, where its center corresponds to the topmost apex portion thereof. Its upper and lower sides expresses the posterior and anterior wall sides, respectively, while its right and left sides corresponds to the cardiac inner wall of the left ventricle free wall and the inner wall in the septum left ventricle side, respectively.

A semicircular developed view shown in FIG. 41D is made by cutting the epicardium surface at the posterior wall along its major axis direction and developing the cut epicardium. A quarter-circle developed view shown in FIG. 41E is made by cutting the right ventricle endocardium at the frontal wall side along its major axis direction and developing the cut endocardium. Further, another approximate quarter-circle developed view shown in FIG. 41F is made cutting the left ventricle endocardium at the frontal wall side along the major axis direction and developing the cut endocardium.

After a desired one being selected from these six types of developed views, developed view data of the selected type view are produced with known methods (Step S104-42).

Like the foregoing embodiments, the CPU 120 reads distribution data of excitation onset times (Step S104-43), produces their isochrone chart data (Step S104-44), selects type to be displayed of a myocardial electroaction amount (Step S104-45), and produces density image data of the selected amount(for example, such as action potential amplitudes) (Step S104-46).

Then, data to be displayed are produced by synthesizing the isochrone chart data, the density image data, and character data such as figures displayed as indices onto the produced developed view data with their developed positions matched. The synthesized data are visualized on the monitor 115 or printer 116. Accordingly, by way of example, an excitation onset time distribution and a myocardial electroaction amount distribution are superposedly displayed on a selected circular developed view of the ventricular outer wall (refer to FIG. 41A). The same is applied to the remaining developed views.

Compared with the eighth embodiment, the display method has the following superiority. While the display method of the eighth embodiment can provide distributions of excitation onset times and/or a myocardial electroaction amount on the ventricular surface, those distributions on the endocardium surface are not easy to be observed. When it is required that distributions existing on a vernacular surface positioning on the back of a displayed surface be displayed, an operator should be alter the position of the viewing direction, although those distributions are on the epicardium surface. In contrast, using the developed view method of the ninth embodiment makes it easier to observe distributions on the endocardium. In addition, for the epicardium, distributions on all the positions thereof are also shown by only one view, thus providing no need for changes in the viewing direction. The entire distribution can be observed at a time.

Particularly, the development according to FIGS. 41A to 41C provides an advantage that easily shows disease portions existing on the cardiac surface. On one hand, developing in FIGS. 41D to 41F provides an advantage that a difference in distance between the apex and the cardiac base portion is smaller that in FIGS. 41A to 41C, in terms of ratios between an actual cardiac surface area and its developed area.

Distribution data that are superposed on the developed view may be only one of excitation onset times and a myocardial electroaction amount. Also, instead of the isochrone chart of excitation onset times, a color-gradated image thereof may be used. Instead of the density image of a myocardial electroaction amount, a color-gradated image thereof may be used. Conductance can be adopted as the myocardial electroaction amount.

Tenth Embodiment

Figure 42B:
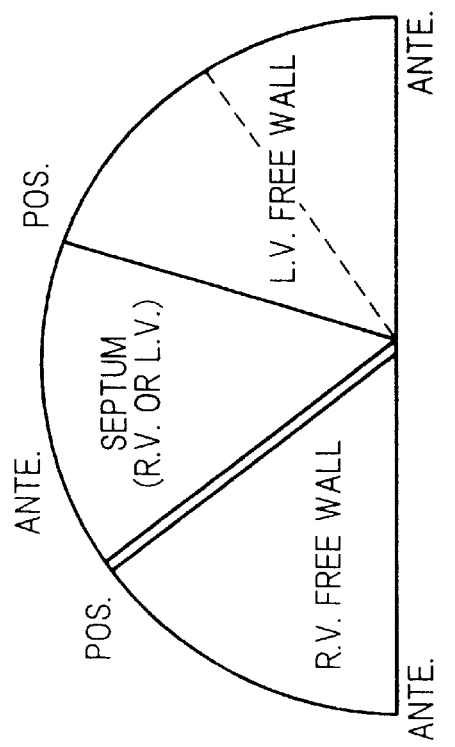
FIGS. 42A and 42B pictorially show images of developed views prepared in a tenth embodiment of the present invention.
Figure 42A:
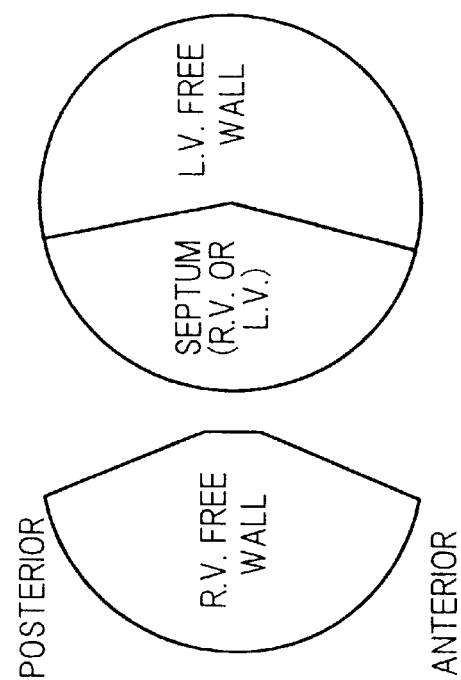

Referring to FIGS. 42A and 42B, a tenth embodiment of the present invention will be described. This embodiment relates to another display based on the developed view of the ventricular surface described above. An excitation onset time distribution and/or a myocardial electroaction amount distribution are analyzed and superposedly displayed on one of developed views for the ventricular inner and outer walls.

The CPU 120 executes processing for a developed view shown in FIGS. 42A or 42B in Steps S104-41 and -42. FIG. 42A shows a bull's-eye-map developed view formed by developing only the epicardium or endocardium, using the method in FIGS. 41A to 41C. FIG. 42B illustrates a semicircular developed view formed by developing only the epicardium or endocardium, using the method in FIGS. 41D to 41F.

Either developed view in FIG. 42A or 42B is selected, and data for a developed view selected are produced. Then Steps S104-43 to -47 in FIG. 40 are executed. Therefore, at least one of an excitation onset time distribution and a myocardial electroaction amount distribution are superposedly displayed on either developed view (i.e., epicardium or endocardium) of FIG. 42A or 42B.

This display method is effective in that only a wanted developed view is displayed. For example, abnormalities in the cardiac muscle are wanted to be observed on only the endocardium, the epicardium which is unnecessary for this diagnosis is not displayed on the monitor, and vice versa. Because image information is limited to desired one in advance, this helps an interpreter to get only necessary information quickly and steadily.

Eleventh Embodiment

Referring to FIGS. 43 to 46, an eleventh embodiment of the present invention will be described. In this embodiment, different two types of images are concurrently displayed. Specifically, each of a pair of a perspective projected view and a sectional view of the ventricles or a pair of a perspective projected view and a projected view of the ventricles are displayed at a time. On the displayed image, an excitation onset time distribution and/or a myocardial electroaction amount distribution are superposed.

Figure 43:
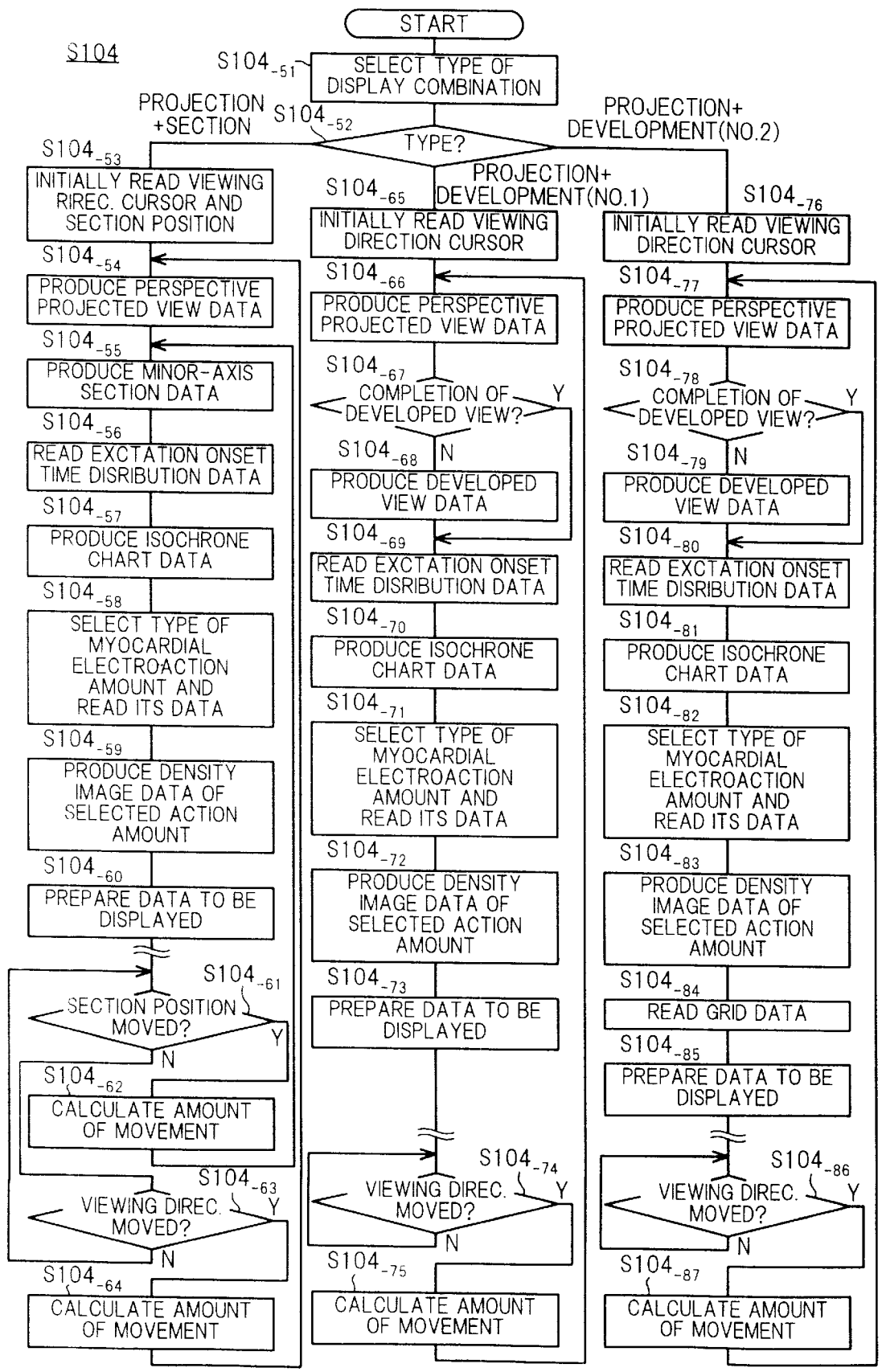
FIG. 43 is a flowchart for producing image data to be displayed in an eleventh embodiment according to the present invention.
Figure 44:
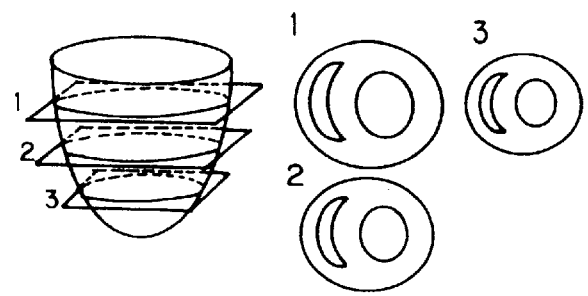
FIG. 44 exemplifies one display where two types of view are present.
Figure 45:
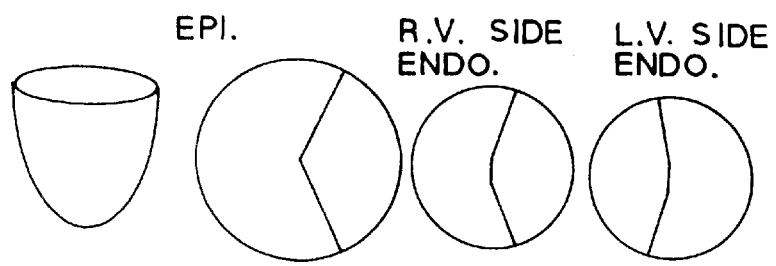
FIG. 45 exemplifies another display where two types of view are present.
Figure 46:
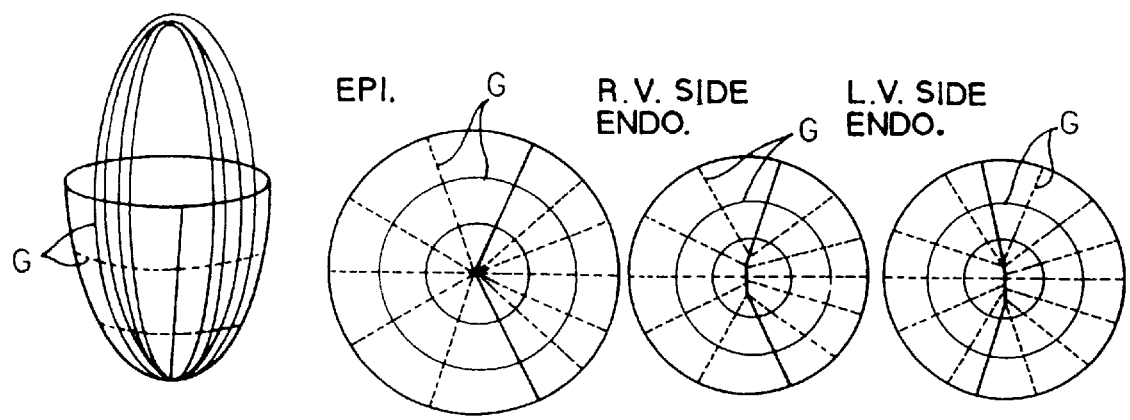
FIG. 46 exemplifies another display where two types of view are present.

Instead of Step S104 in FIG. 16, the CPU 120 executes processing shown in FIG. 43. The CPU 120 selects a combination type of images to be displayed on the basis of operational information provided through the operation panel 117 (Step S104-51). As such combination, provided in advance are a first combination of a perspective projected view and a minor-axis sectional view of the ventricles as shown in FIG. 44, a second combination (NO.1) of a perspective projected view and a developed view of the ventricles as shown in FIG. 45, and a third combination (NO.2) of a perspective projected view and a developed view of the ventricles as shown in FIG. 46.

The CPU 120 determines the type of a combination for display (Step S104-52). If the determination is "perspective projected view and developed view", Steps S104-53 to -64 are subjected to processing.

Practically, a viewing direction cursor for defining a viewing direction toward a perspective projected view and cut positions and initial positions of minor-axis cross sections are read from the memories 121 (Step S104-53). As shown in FIG. 44, as the cut positions, positions 1 to 3 are prepared on a perspective projected view. Thus a plurality of cut positions mutually different in the major-axis direction are read. Data of the ventricular perspective projected view are produced along the initial position of the viewing direction cursor, and data of a plurality of minor-axis cross sections along the sectional cut positions initially set (Step S104-54 and -55).

For superposition display on a plurality of minor-axis cross sections initially set, distribution data of excitation onset times are read from the memories, isochrone chart data are produced at each sectional position, a type of a myocardial electroaction amount to be analyzed is selected, and density image data of the selected amount are produced at each sectional position (Step S104-56 to -59), which are performed in turn in the same manner as described before. Frame data to be displayed are then prepared (Step S104-60). The projected view data and sectional view data are each placed in multi-windows, the isochrone chart data and density image data are superposed on the sectional view data, a plurality of frames of projected data each indicating each minor-axis cross section are superposed on the projected view data, and necessary graphic data are placed at positions in the superposed image data, thus providing a frame data to be displayed. The frame data are then sent to the monitor 115 or printer 116 for visualization (FIG. 16, Step S105). One display example is shown in FIG. 44.

An operator can adjust the cut positions of the minor-axis cross sections and the viewing direction of the projected view with observing the displayed image or chart. If the sectional cut position is moved by an operator, the CPU 120 determines it, and calculates a moved amount (Steps S104-61 and -62). In response to this movement, the processing is passed to Step S104-55 for producing and displaying an updated superposition image.

As long as the minor-axis cross sections are not moved positionally, the processing waits as determining whether or not the position of the viewing direction cursor will be moved (Step S104-63), and if moved, the moved amount is calculated (Step S104-64). After this, the processing returns to Step S104-54 to repeat the foregoing processing with a new viewing direction.

As shown in FIG. 44, displaying on multi-window screens are a perspective projected view observed along a viewing direction set toward the ventricles as well as three minor-axis cross sections, for example. On each of the minor-axis cross sections, an isochrone chart of an excitation onset time distribution and/or a density image of a myocardial electroaction amount, both inherent to each sectional position, are superposed. Such display is updated every time when the viewing direction or sectional cut position is changed. Accordingly the equivalent advantages to the above can be obtained. Moreover, the sectional positions are concurrently indicated on the projected view, making recognition of each sectional position easier as well as providing a clearer positional relationship. In other words, although it is difficult to understand which cross section corresponds to which position, if a plurality of cross sections are displayed without any index, such difficulty has been overcome.

In the display in FIG. 44, the minor-axis cross sections can be replaced with ventricular major-axis cross sections. An excitation onset time distribution and a myocardial electroaction amount can additionally be analyzed on the ventricular surface in order to superposedly displaying the analyzed results on a perspective projected view.

On one hand, if the determination is "perspective projected view and developed view (NO.1)" at Step S104-52, Steps S104-65 to -75 will follow.

A position of the viewing direction cursor is initially read, and data of a ventricular perspective projected view are produced along the cursor direction (Step S104-65 and -66). When a ventricular developed view has not been produced yet, the developed view data are produced (Step S104-67 and -68). As types of developed views, exemplified in FIG. 45 are the ventricular outer wall, right ventricle side inner wall, and left ventricle side inner wall.

For each developed view data, isochrone chart data of an excitation onset time distribution and/or density image data of a myocardial electroaction amount are produced on the ventricular surface (Step S104-69 and -72). These produced data are synthesized into frame data to be displayed (Step S104-73). In this synthesis, both the perspective projected view and the developed view are arranged in parallel, and the isochrone chart data and/or the density image data, which taken from each ventricular surface corresponding to each developed view, are superposed on each developed view. The frame data are sent to the displaying means (FIG. 16, Step S105).

If an operator has moved the viewing direction, data of a new perspective projected view are reproduced according to the moved amount, the foregoing processing being repeated (Step S104-74 and -75).

As shown in FIG. 45, both a perspective projected view and a plurality of types of developed views are simultaneously displayed in a multi-window format, and analyzed results of an excitation onset time distribution and/or a myocardial electroaction amount distribution are superposed on each developed view. Therefore, this contributes to improvement in diagnostic efficiency. In the above display, it is preferred that analyzed results of intracardiac electrophysiological phenomena are superposed on the perspective projected view.

In cases where the determination is "perspective projected view and developed view (NO.2)" at Step S104-52, Steps S104-76 to -87 will follow. Of these Steps S104-76 to -83 are the same in contents as Steps S104-65 to -72 described above.

After the production of data to be displayed, grid data are read from the memories (Step S104-84). The grid data, as shown in FIG. 46, are data composing virtual lines sectioning a ventricular model along both the major- and minor-axis directions in grid patterns. The grid data are then superposed on both a perspective projected view and a developed view (Step S104-85). At this step S104-85, the remaining data preparation is the same in content as Step S104-73. After this, when an operator has moved the viewing direction, data of a new perspective projected chart are reproduced in accordance with the moved amount, and the foregoing processing is repeated (Steps S104-86 and -87).

As shown in FIG. 46, both a perspective projected view and a plurality of types of developed views are simultaneously displayed in a multi-window format, and analyzed results of an excitation onset time distribution and/or a myocardial electroaction amount distribution are superposed on each developed view. At the same time, on each of the perspective projected view and developed views, a grid G virtually dividing the ventricular surface is superposedly displayed. This grid enables a clearer positional correspondence between the perspective projected view and the developed views.

According to FIG. 46 display, the developed views make it possible to not only recognize diseases on all the ventricular surfaces at a glance but also grasp edges and sizes of the diseases accurately. The grid G allows a clearer positional correspondence between both the two types of views. In addition, to superpose analyzed results on the perspective projected view permits doubtful or abnormal portions on the cardiac muscle to be easily found on the developed views. The perspective projected view allows detailed observation for such occasion.

Twelfth Embodiment

Figure 47:
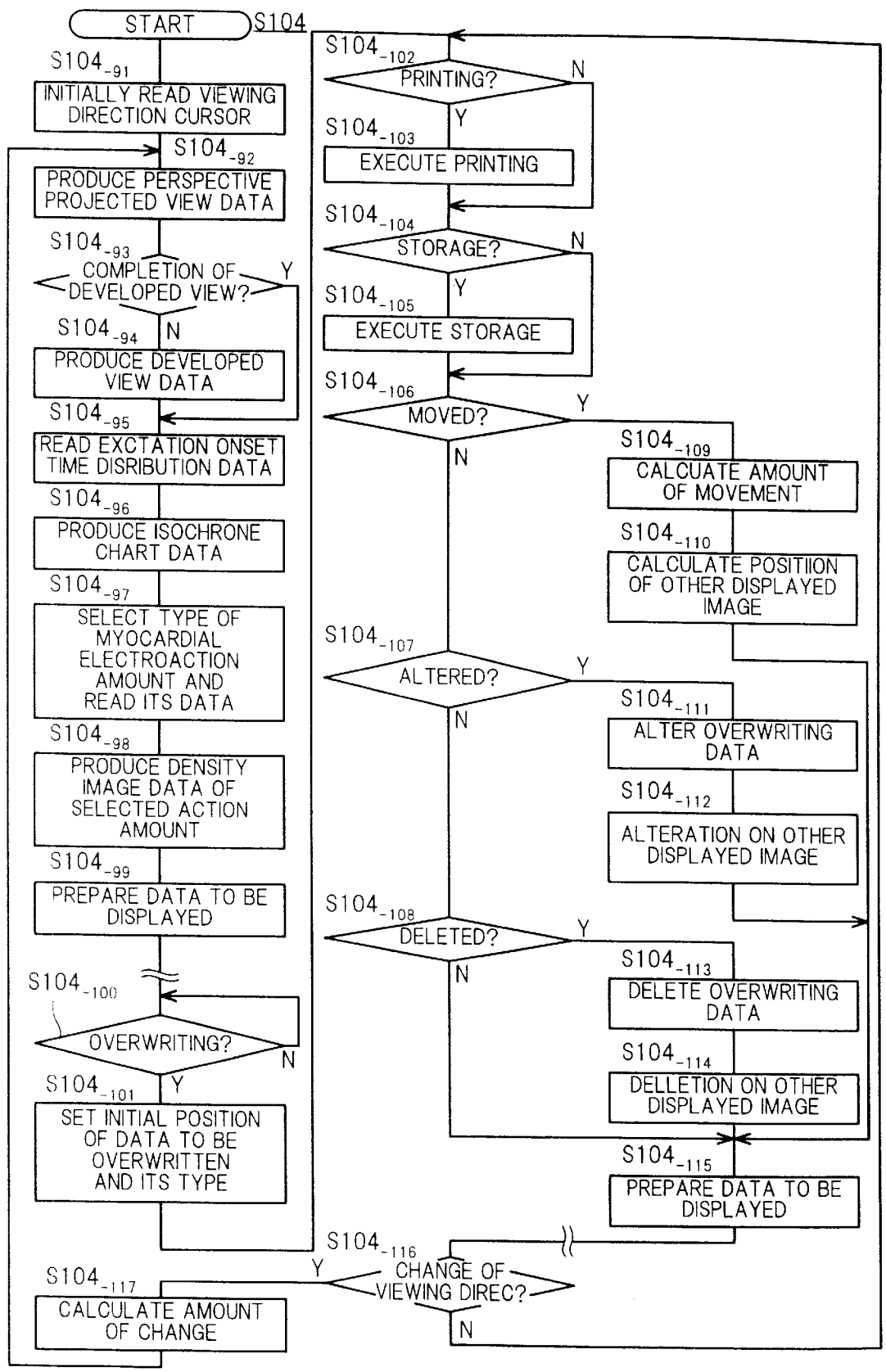
FIG. 47 is a flowchart for producing image data to be displayed in a twelfth embodiment according to the present invention.
Figure 48:
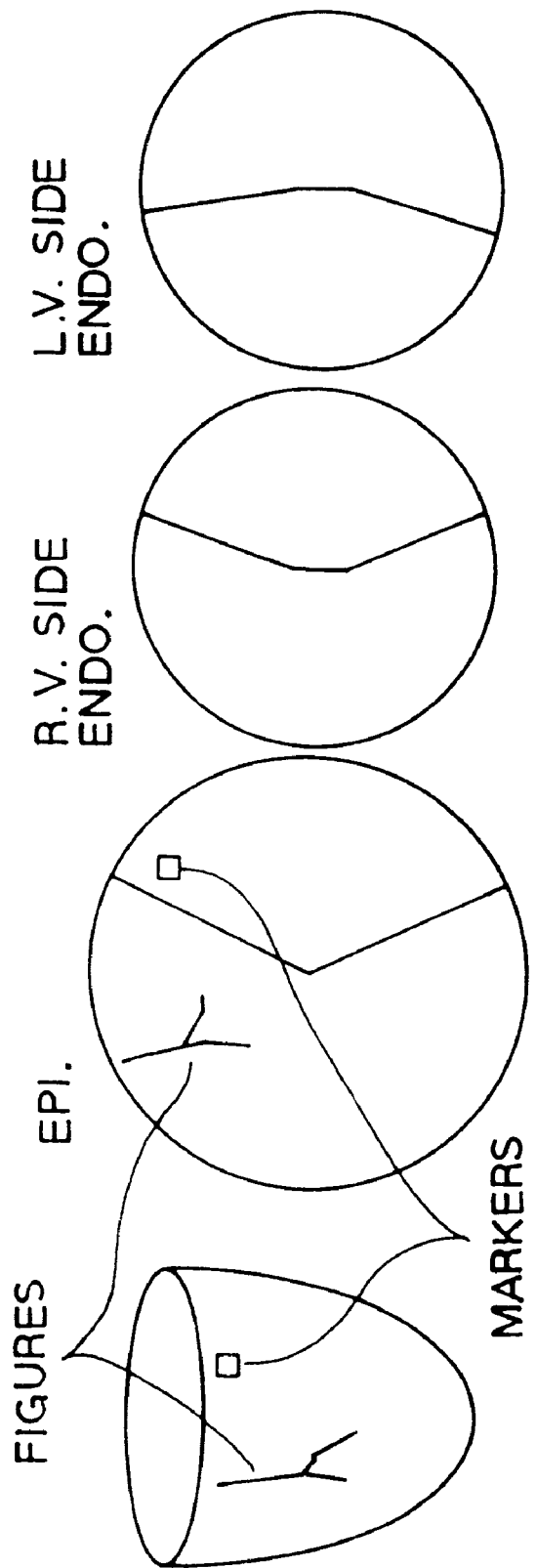
FIG. 48 exemplifies one display where two types of view are present with markers.

Referring to FIGS. 47 and 48, a twelfth embodiment of the present invention will be described. A diagnostic system of the embodiment, like the eleventh embodiment, is concerned with a configuration where both a perspective projected image of the cardiac muscle and developed views thereof are displayed in a complex mode, and data such as markers can be overwritten by an operator at any position on the displayed image. Such writable data include lines, graphics, characters, and markers (circles, crosses, arrows, etc.), which are referred to as overwriting data.

The CPU 120 executes preparation for data to be imaged shown in FIG. 47 in place of FIG. 16, Step S104. A position of a viewing direction cursor is initially read, data of a perspective projected view along the viewing direction are produced, and data of a developed view are produced (Steps S104-91 to -94). Isochrone chart data of an excitation onset time distribution and density image data of a myocardial electroaction amount are then produced, and synthesized one on another to prepare data to be displayed (Steps S104-95 to -99). This data for displaying are based on a multi-window format where a perspective projected view and a plurality of types of developed views are arranged. The prepared data are sent to the monitor 115 through Step S105 in FIG. 16, and displayed thereon (FIG. 48).

The CPU 120 waits for the next processing with determining whether the overwriting data should be written or not by checking operational information from the operation panel 117 (Step S104-100). In the case of overwriting, an initial positions to write overwriting data and a type thereof (for example, one type such as only makers, or, plural types such as markers and graphics) are set (Step S104-101). As the initial position, a position corresponding to both one view (for example, perspective projected view) and the other view (one of the plural developed views) is specified. As the overwriting data, figure data and/or markers are selected.

In the case of printing the overwriting data thus-written on films or papers, a printing command is sent, for example, to the printer 16 (Step S104-102 and -103). In cases where the overwriting data thus-written are stored in a memory so that they are re-read later, a storing command is sent to the memories 121 (Step S104-104 and -105).

The CPU 120 determines if the overwriting data written are moved positionally or not, if its type (or its shape) is altered or not, then if it is deleted or not (Steps S104-106 to -108).

When the overwriting data are moved on either one view (i.e., on the perspective projected view or the developed view), the moved amount is calculated based on operational information given from an operator, and a corresponding moved position on the other view is also calculated (Steps S104–109 and -110). When the overwriting data are altered on either one view, the altered overwriting data are analyzed based on operational information, altered overwriting data on the other view are set (Step S104–111 and -112). Further, when the overwriting data are deleted on either one view, the data deletion is carried out based on operational information, and deletion is also carried out on the other view (Steps S104–113 and -114).

After such movement, alteration, and deletion, Step S104–115 is processed, where data to be displayed are prepared such that the overwriting data for the initial position or for updated positions, types (shape), and others are overwritten (superposed) on the data which will be displayed. The prepared data are sent to the monitor 115 and/or printer 116 and displayed thereon. One such display example is shown in FIG. 48. If the overwriting data have not been moved, altered and deleted, and the viewing direction has been unchanged, the Step S104–115 is substantially omitted from the processing.

Then, in the case that the viewing direction toward the perspective projected view is changed, the changed amount is calculated, again proceeding to the production of projected view data (Steps S104–116 and -117). To the contrary, the viewing direction is not been changed, returning to Step S104-102 to repeat the foregoing processing.

According to this configuration and function, operators are allowed to not only add overwriting data, such as lines, characters, graphics, and/or various types of markers, at any position on the perspective projected view and the developed view displayed together but also freely move, alter, or delete the overwriting data. The overwriting data added to one side view are automatically added to the other side view. When the overwriting data are moved, altered and deleted on one side view, corresponding movement, alteration and deletion are performed on the other side view. The overwriting data once written can be printed on films or papers or stored in a medium to read later.

As a result, in addition to the similar advantages to those in the eleventh embodiment, interpreted results can be recorded with symbols or characters, because operators can write different overwriting data, print them, or store them in a memory medium. This performance makes it easy to refer interpreted results later, to transmit them to other clinical modalities, and to postprocess them.

Thirteenth Embodiment

Figure 49:
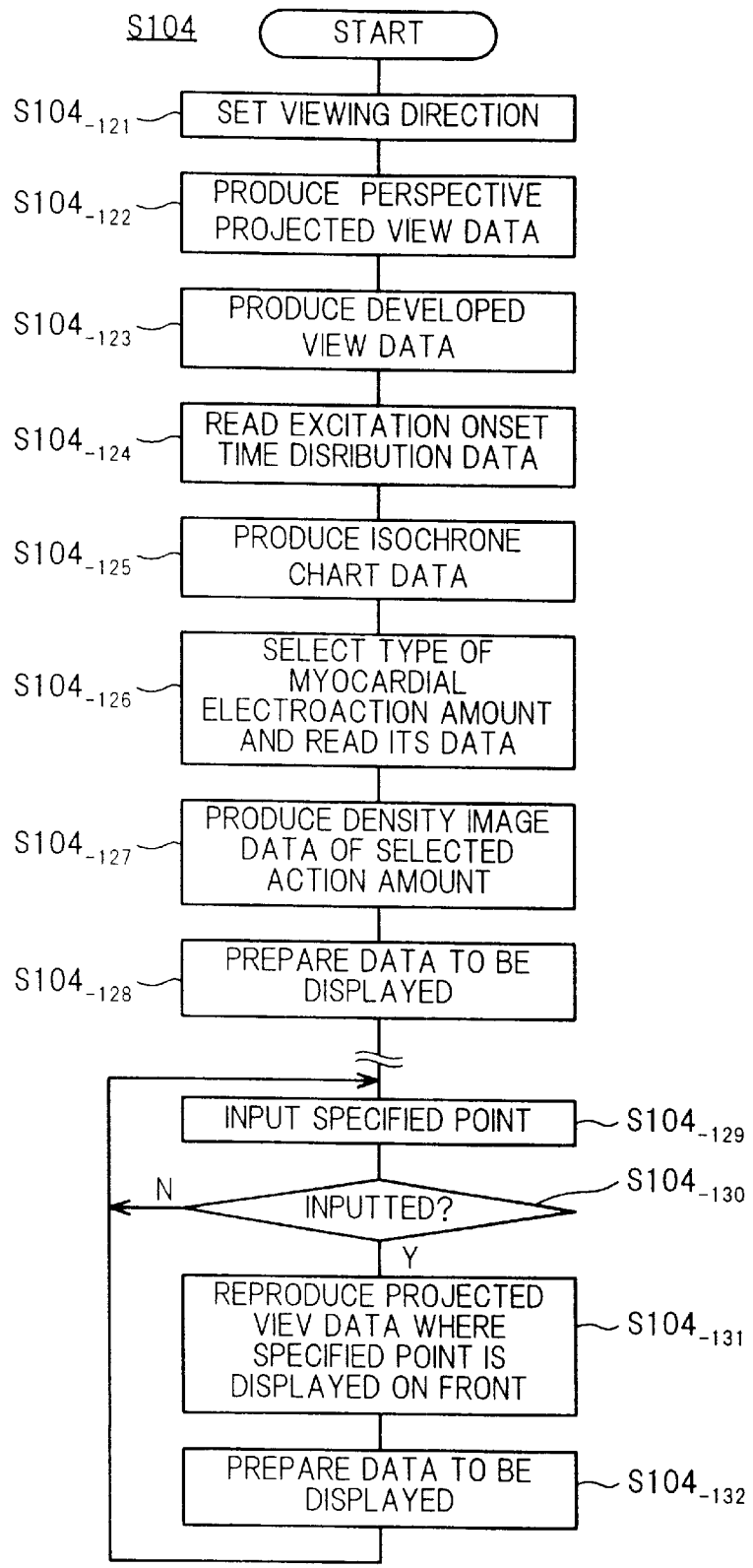
FIG. 49 is a flowchart for producing image data to be displayed in a thirteenth embodiment according to the present invention.
Figure 50:
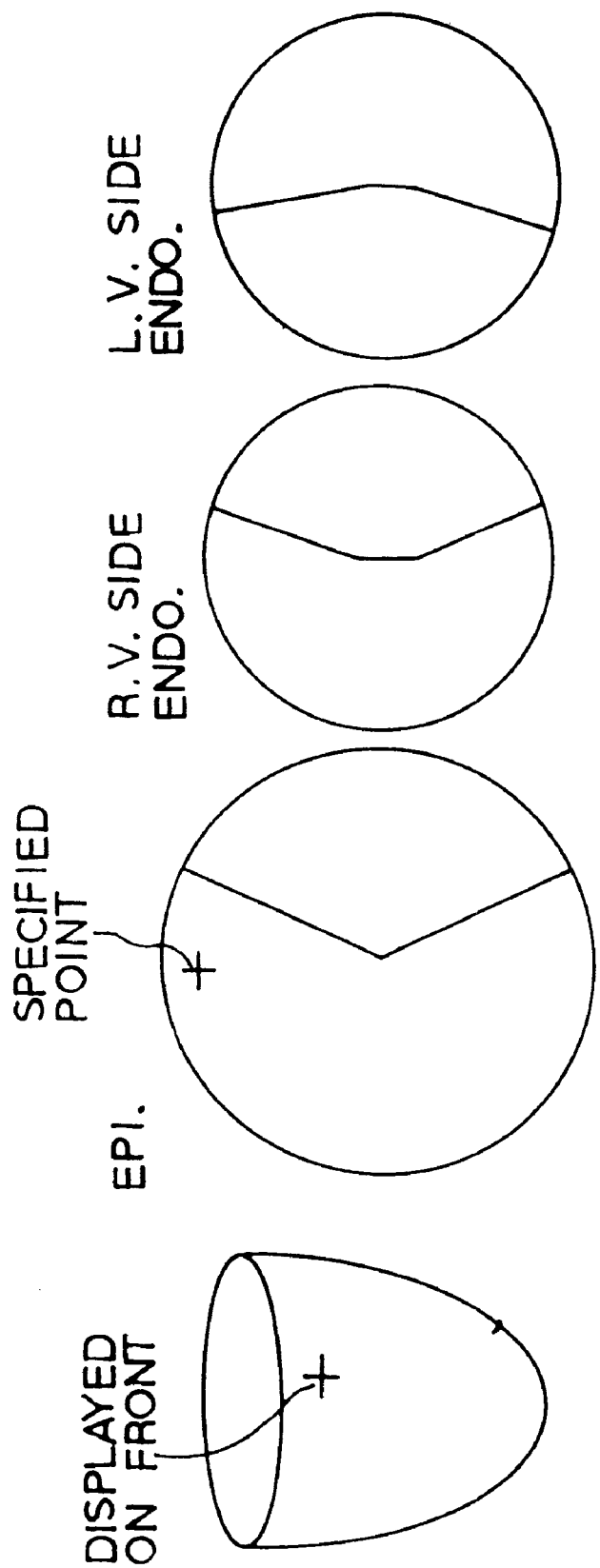
FIG. 50 exemplifies a display where two types of view are present with a specified point.

Referring to FIGS. 49 to 50, a thirteenth embodiment of the present invention will be described. A feature of this embodiment is to concurrently display a perspective projected view and developed views of the ventricles, like the foregoing embodiments, where a point is specified on one of the developed views, so that a surface of the ventricles which corresponds to the specified point becomes the front of the perspective projected view.

The CPU 120 executes processing shown in FIG. 49 as the production of data to be displayed at Step S104 in FIG. 16. Practically, a viewing direction toward a ventricular perspective projected view to be displayed is set, and its projected view data are produced (Steps S104–121 and -122). A plurality of types of developed view data of a ventricular surface are then produced (Step S104–123). The developed views consists of, for example, three projected views; an epicardial, right-ventricular endocardiac, and left-ventricular endocardiac developed views, as shown in FIG. 50.

Like the foregoing processing, isochrone chart data of excitation onset time distributions and density image data for a myocardial electroaction amount both of which are superposed on the developed views are produced (Steps S104–124 to -127). As preparation of data to be displayed, the projected view data and the developed view data are combined into a frame data based on a multi-window format and the analyzed electroaction data are placed on each of the developed views. The data thus-prepared are displayed on the monitor 115, for example. FIG. 50 exemplifies one displayed image.

In this display state, an operator is to put via the operation panel 117 a marker (i.e., specified point) on a desired position on the developed views. The CPU 120 inputs this specified point position (Steps S104–129 and 130). If the point position is inputted, the perspective view data are rotated (i.e., reproduced) so that a normal direction at the specified point position agrees with the viewing direction which is set at present (Step S104–131). Data to be displayed are prepared again using the rotated perspective view data and the developed view data which had been produced (Step S104–132). The re-prepared data are sent to the monitor 115 and/or printer 116. In this processing, it is possible to make the viewing direction changeable.

As a consequence, as shown in FIG. 50, if a cross marker is put on a certain position of the frontier side of a developed view displaying the epicardium, the image is displayed such that a surface of the epicardium which corresponds to the specified point on the developed view is displayed as a front of the perspective projected view. Particularly, when a point is specified on an endocardium developed view, it is preferred that the ventricles are cut with the foregoing fashion so as to show the specified point on a perspective projected view. This display in this embodiment makes it possible to re-display lesions found on the developed views on the perspective projected view so as to be observed in the most proper angle. This re-display is extremely easy to be performed, improving efficiency in interpretation and diagnosis.

Fourteenth Embodiment

Figure 51:
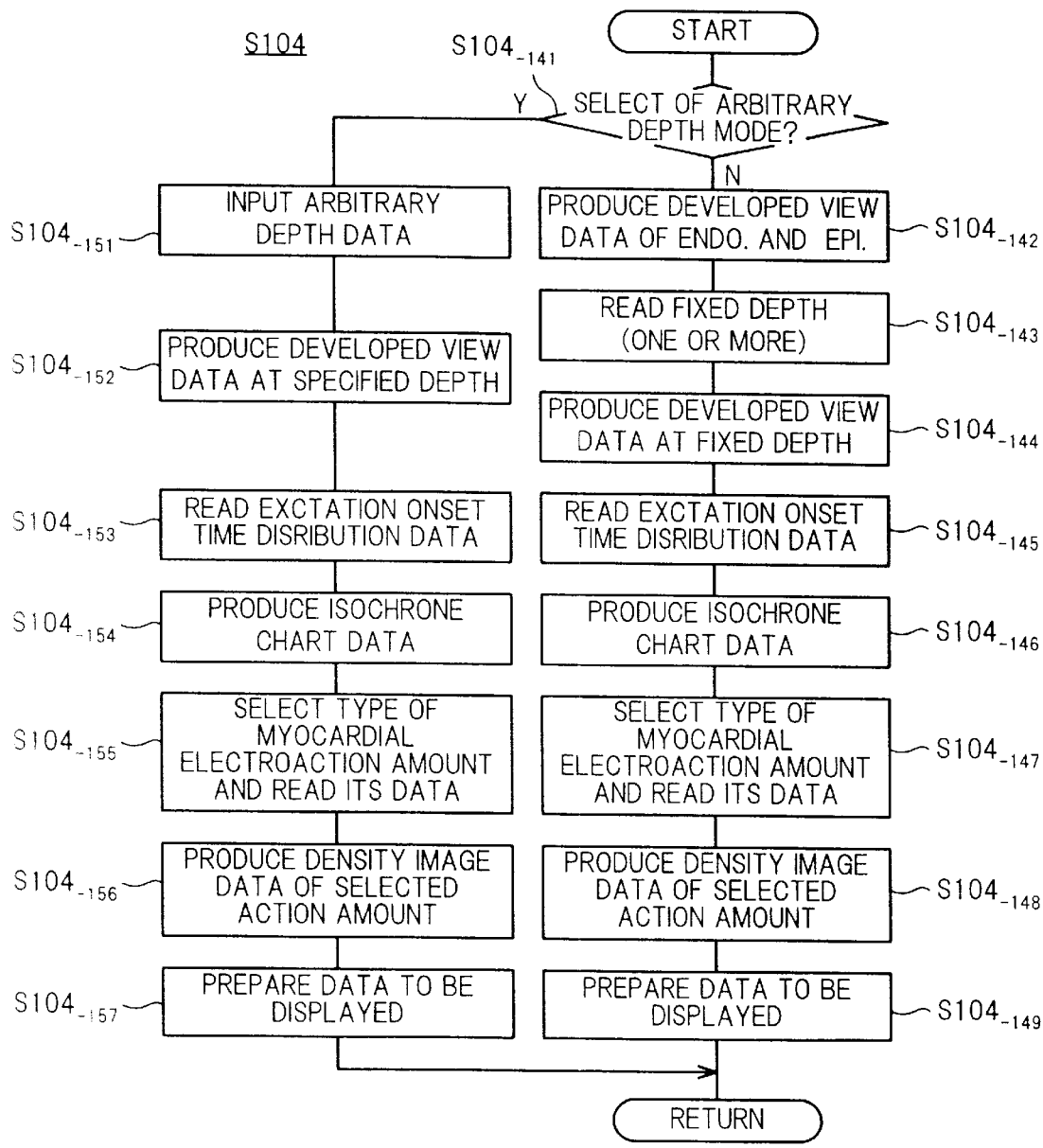
FIG. 51 is a flowchart for producing image data to be displayed in a fourteenth embodiment according to the present invention.
Figure 52:
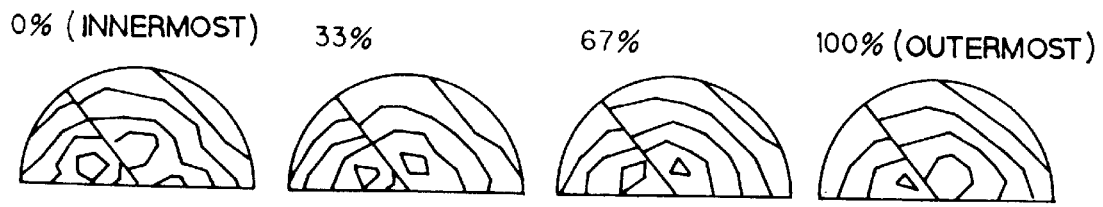
FIG. 52 exemplifies a display in which developed views are arranged in response to fixed depths.
Figure 53:
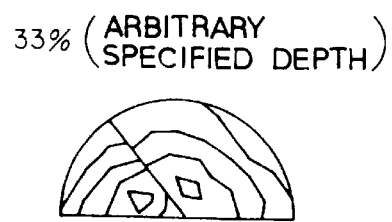
FIG. 53 exemplifies a display in which a developed view is displayed in response to a specified arbitrary depth.

Referring to FIGS. 51 to 53, a fourteenth embodiment of the present invention will be described. This embodiment is concerned with a diagnostic system that superposedly-displays intracardiac electrophysiological phenomena on ventricular developed views. Particularly, a feature is that depths between the epicardium and the endocardium can be set fixedly or freely for the superposition display. The term "depth" used herein means the distances in its wall thickness direction.

FIG. 51 shows the outline of processing executed by the CPU 120 as the production of data to be displayed. First the CPU 120 determines, based on operation information provided, if or not data of a developed view should be produced for an arbitrary depth (Step S104–141).

If NO in this determination, a command is for a fixed depth, executing to Steps S104–142 to -150 in sequence. At first, sets of data of developed views for the epicardium and endocardium surfaces are produced, like the foregoing fashion (Step S104–142). Data indicate of preset fixed depths are read from the memories 121 (Step S104–143). The number of the fixed depths are plural or single. If the number is single, it is specified as, for example, "a depth of 30% from the endocardium". If the number is plural, the depths are specified as, for example, "depths of 33% and 67% from the endocardium, respectively". Data of ventricular developed views at one or more specified fixed depths are then produced (Step S104–144). Like the foregoing, produced are data expressing intracardiac electrophysiological phenomena (such as isochrone char data of excitation onset time distributions and density image data for a myocardial electroaction amount) at each specified fixed depth (Step S104–145 to -148).

After such data completion, the data of electrophysiological phenomena are superposed on developed view data to form data to be displayed (Step S104–149). For instance, when the fixed depths are 33% and 67% from the endocardium, respectively, the endocardium and epicardium are added to provide four types of developed views, and those data are produced. As a result, as shown in FIG. 52, those four views are arranged from the left in turn, wherein the data of electrophysiological phenomena corresponding to each depth are superposed on each view, forming four views into a one image displayed at a time by the monitor 115 and/or printer 116 (Step S105 in FIG. 16).

In the example shown in FIG. 52, a developed view of the endocardium is present at the leftmost side position with its analyzed results, another developed view at a depth of 33% from the endocardium is present next to the leftmost one with its analyzed results, and another developed view at a depth of 67% from the endocardium is present next to the second one with its analyzed results. At the rightmost side position, a developed view of the epicardium is present with its analyzed results. Such display allows analyzed results surfaces (depths) other than the ventricular surfaces to be displayed. Hence this display is effective in understanding easily how deep lesions advance into the cardiac muscle form the surfaces.

By contrast, when YES in the determination at Step S104–141, the above display is performed with an arbitrarily specified depth. Thus specified depth information is acquired through the operation panel 117 from an operator, and data of a ventricular developed view at the specified arbitrary depth are produced (Step S104–151 and -152). Data expressing electrophysiological phenomena at the specified arbitrary depth are produced, and their data to be displayed are prepared (Steps S104–153 to -157).

As a result, by way of example, the monitor 115 and/or printer 116 visualize an image shown in FIG. 53, wherein a developed view at a specified arbitrary depth (for example, a depth of 33% from the endocardium) is shown with its analyzed results. Compared with display shown in FIG. 52, the view image can be larger in size, being superior in observing details.

In the foregoing, it is preferred that the preset fixed depths can be updated if necessary. To displayed images in FIGS. 52 and 53, a ventricular perspective projected view may be added in parallel.

Fifteenth Embodiment

Referring to FIGS. 54 and 55A to 55C, a fifteenth embodiment of the present invention will be described. In this embodiment, in lieu of an excitation onset time distribution, divergences in conduction velocities of excitation or excitation onset times is displayed.

A conduction velocity v of excitation of a divergence a in excitation onset times can be obtained from equations $$v=|1/\nabla t|$$
$$a=\nabla \cdot \nabla t$$

where t is an excitation onset time.

Because the cardiac muscular has anisotropy in the conduction of excitation, it is considered that the calculated velocity v may differ from an actual one in some cases. Therefore it is preferred to perform appropriate correction with the velocity.

Figures 55A, 55B, 55C:
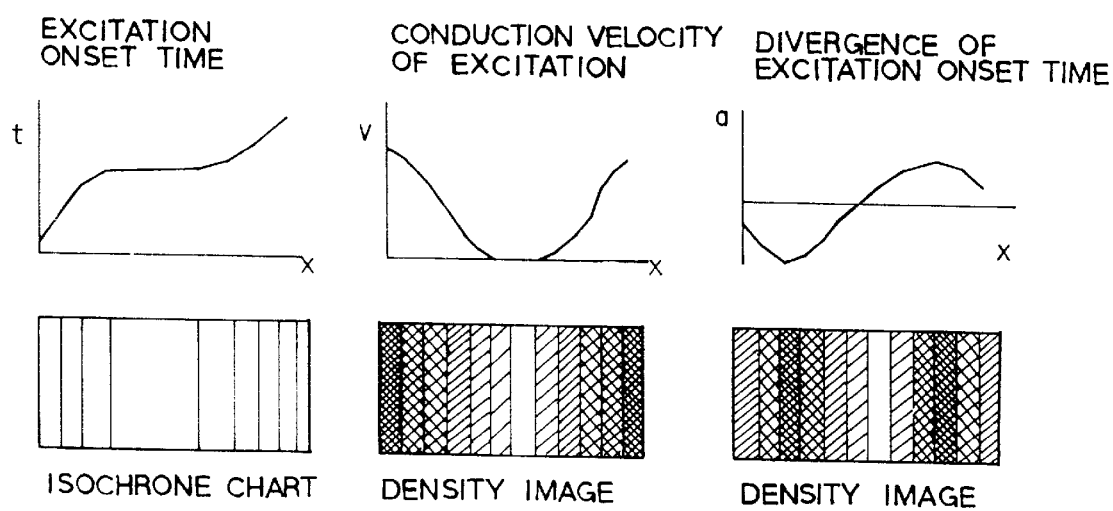
FIGS. 55A to 55C are graphs indicative of excitation onset times, conduction velocities of excitation, and divergence of the times.

FIGS. 55A to 55C pictorially show the relationship among excitation onset times t, conduction velocities v and divergences a in excitation onset times, wherein x shows distances in a certain direction. If it is assumes that the times t changes as shown in FIG. 55A, the conduction velocities v changes as shown in FIG. 55B, showing larger velocities at both the end sides on the graph. The divergences a expresses magnitudes of changes in the velocities. Thus as shown in FIG. 55C, its graph includes some larger absolute value ranges depending on larger changes in the velocities. Below the graphs, added are an isochrone chart of the excitation onset times t, a first density image of the excitation onset velocities, and a second density image of divergences a in the times.

Figure 54:
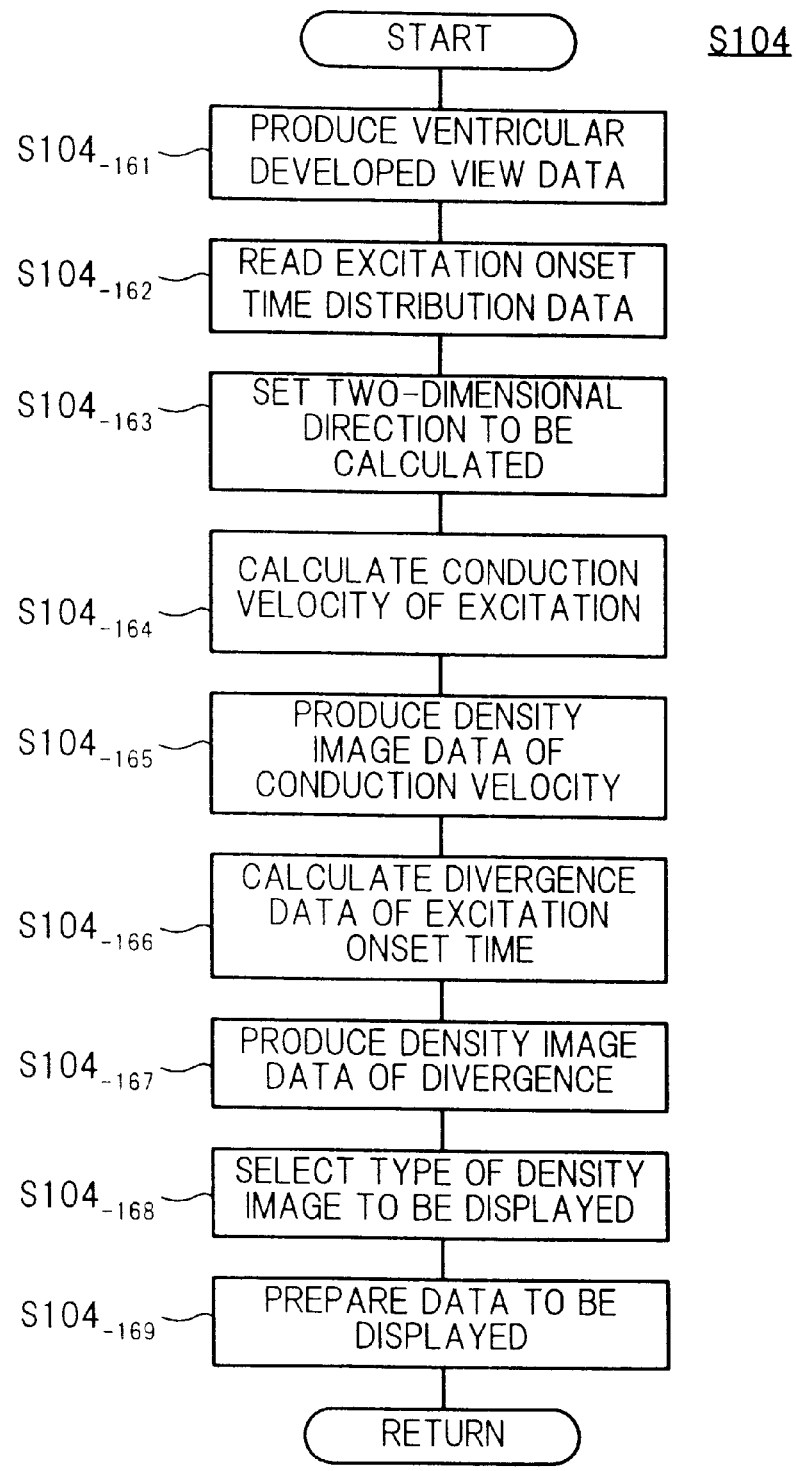
FIG. 54 is a flowchart for producing image data to be displayed in a fifteenth embodiment according to the present invention.

To display conduction velocities v or divergences a, the CPU 120 executes processing shown in FIG. 54. Developed view data of the epicardium and/or endocardium are produced, data of an excitation onset time distribution are read, calculating directions are set on the produced developed views (Steps S104–161 to -163). Every series of positions along each calculating direction, conduction velocities v of excitation are calculated based on the foregoing equation, and its density image data are produced (Steps S104–164 and -165). Also, every series of positions along each calculating direction, divergences a in the times are calculated based on the foregoing equation, and its density image data are produced (Steps S104–166 and -167). Either velocities v or divergences a is selected (Step S104–168), and the selected data are placed on the developed view data to form frame data to be displayed (Step S104–169), then displayed.

Therefore, in the case that the conduction velocities are displayed in place of excitation onset times, there is the advantage that lesions whose conduction velocities are smaller than normal values can be readily found. It is understood that larger divergences in excitation onset times express spatially steeper changes in conduction velocities. In normal regions, it is general that the conduction velocities do not show so steeper spatial changes. Accordingly, in the case of displaying the divergences, if larger divergences are found in the curve, there is a higher possibility that there is something wrong with the ventricles in corresponding regions. Thus, an advantage is that this display is sometimes effective in finding lesions, rather than the direct display of excitation onset times.

Alternative examples are follows. As preparation of data at Steps S104–168 and -169, the two same developed views may be arranged in parallel in a single image, where conduction velocities v are superposed on one developed view, while divergences a in excitation onset times t are superposed on the other developed view, both views being displayed at a time. In this display, a ventricular perspective projected view may additionally be displayed, on which information about electrophysiological phenomena are superposed.

Sixteenth Embodiment

Figure 56:
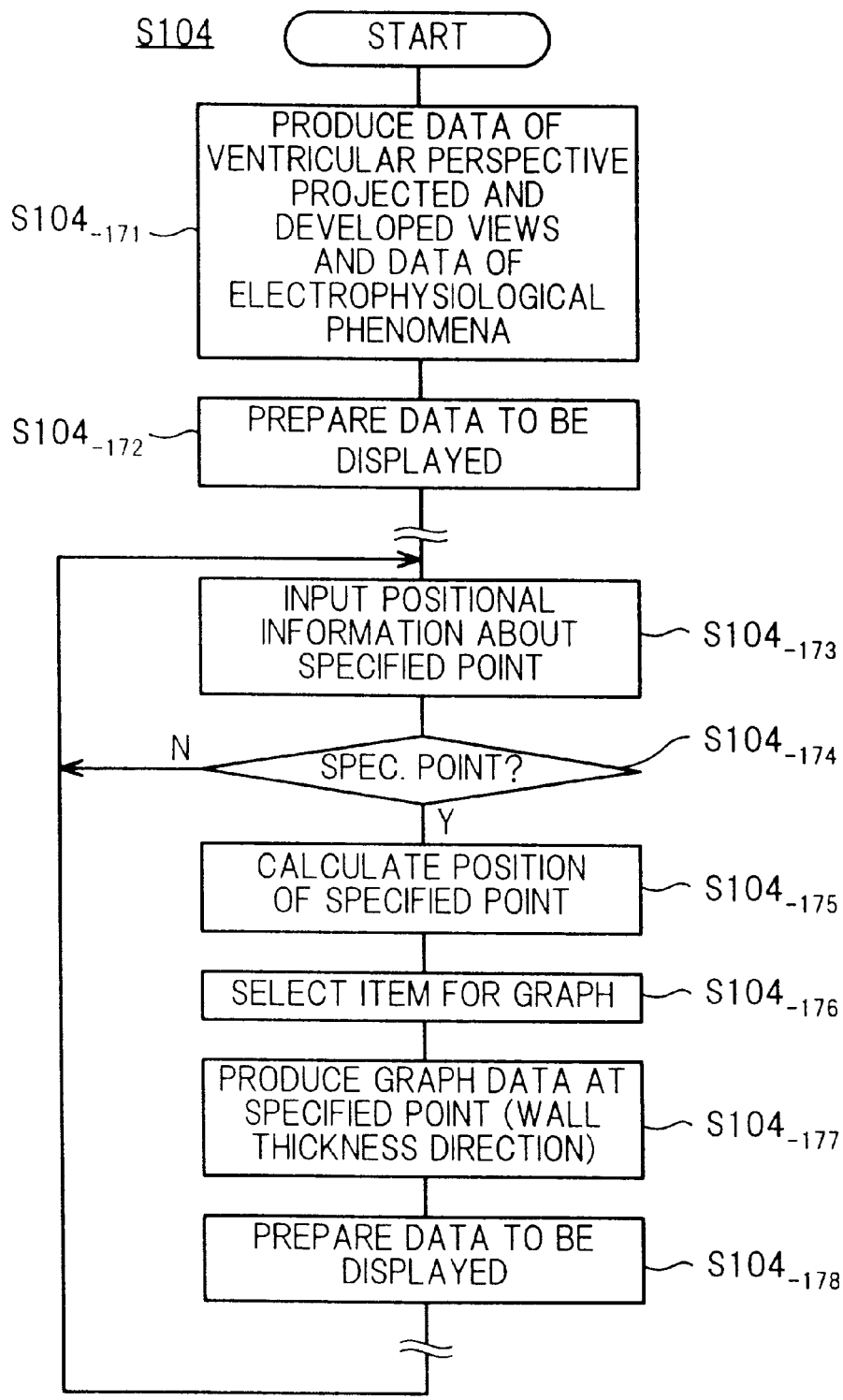
FIG. 56 is a flowchart for producing image data to be displayed in a sixteenth embodiment according to the present invention.
Figure 57:
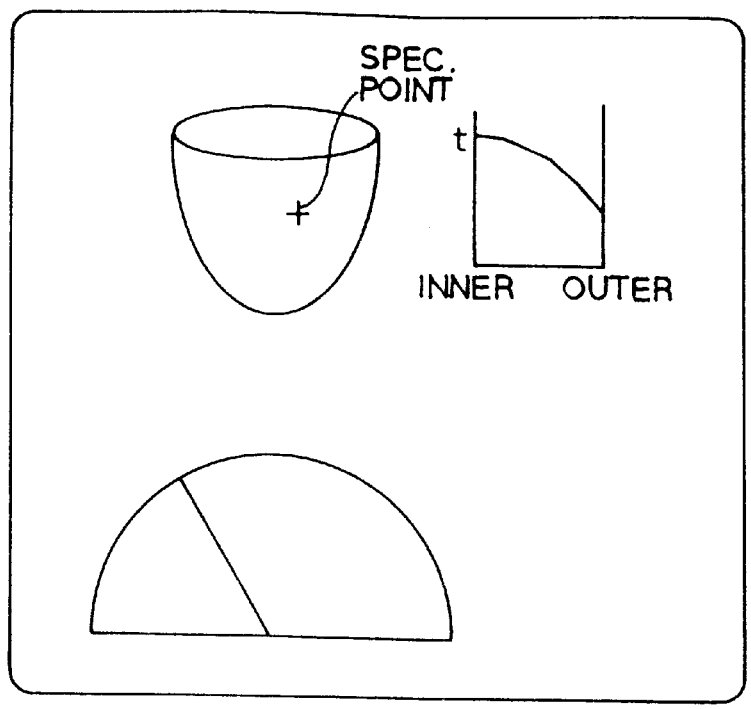
FIG. 57 is a pictorially shown display image with analysis in the wall thickness direction.
Figure 58:
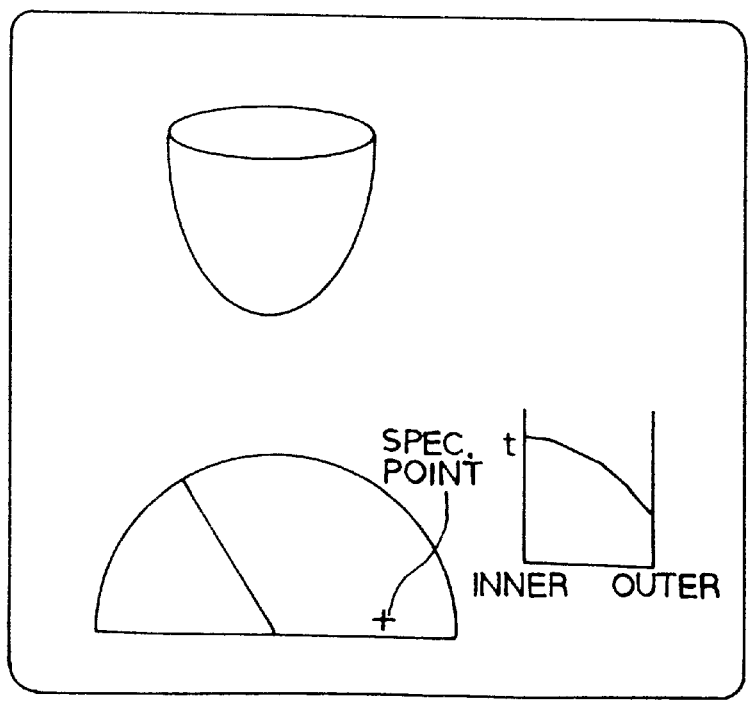
FIG. 58 is another pictorially shown display image with analysis in the wall thickness direction.

Referring to FIGS. 56 to 58, a sixteenth embodiment of the present invention will be described. In this embodiment, an excitation onset time distribution, a myocardial electroaction amount, and other related amounts are analyzed in the wall thickness (i.e., depth) direction of the cardiac muscle at specified positions on the ventricular surface.

The CPU 120 executes processing of FIG. 56. At first, produced are data including edge data of each of a ventricular perspective projected view and developed views of the epicardium and the endocardium, and data to express an excitation onset time distribution and/or a myocardial electroaction amount distribution, and then prepared are frame image data combined with the edge data and the data to be displayed (Steps S104–171 and -172). Accordingly an image is first displayed, on which data of electrophysiological phenomena are superposed on a projected and developed views separately placed in the screen.

An operator operates the operation panel 117 as observing the monitor screen, during which time the operator specifies a point with, for example, a cross marker, on a desired position on the projected or developed view (Steps S104–173 and -174). The position specified is calculated on either projected or developed view, and a desired type of excitation onset times (or, conduction velocities of excitation, divergences in excitation onset times) or a myocardial electroaction amount is selected on operation information (Steps S104–175 and -176). At the specified position, changes in a desired type of electrophysiological phenomenon are calculated, as graph data which is a function of a distance (wall thickness), along the myocardial wall thickness direction at the specified position (Step S104–177). Then, frame data to be displayed are prepared by superposing the graph data and graphic data of the marker on the projected or developed view (Step S104–178), and displayed (FIG. 16, Step S105).

Providing a specified point permits various amounts, including excitation onset times, conduction velocities, divergences in the excitation onset times, or any value or a myocardial electroaction amount, to automatically analyzed along the wall thickness direction at the specified position. In FIG. 57, a marker is given to a desired position on a projected view, while in FIG. 58, it is given to a developed view. The analyzed results at a specified position are automatically displayed on the monitor or outputted to the printer. One such example is a graph showing excitation onset times t over the distances between the epicardium and endocardium. Thus this play makes it easier to observe in detail the progress of lesions along the wall thickness direction.

Giving another specified position will repeat the above processing for each specified position, and a new analyzed graph is displayed quickly and automatically.

The foregoing display processing may be performed with either the perspective projected view or the developed view. Further the viewing direction may be changed at arbitrary directions in the foregoing display processing. With regard to the specified position, another configuration is also possible that a plurality of specified positions are given and the foregoing display processing is performed in parallel with the specified points.

Seventeenth Embodiment

Referring to FIGS. 59 and 60A to 60C, a seventeenth embodiment of the present invention will be described. In this embodiment, excitation onset times (or its relevant amounts) and/or a myocardial electroaction amount are analyzed along the wall thickness direction at each position on the ventricular surface, and the analyzed results are two-dimensionally displayed.

Figure 59:
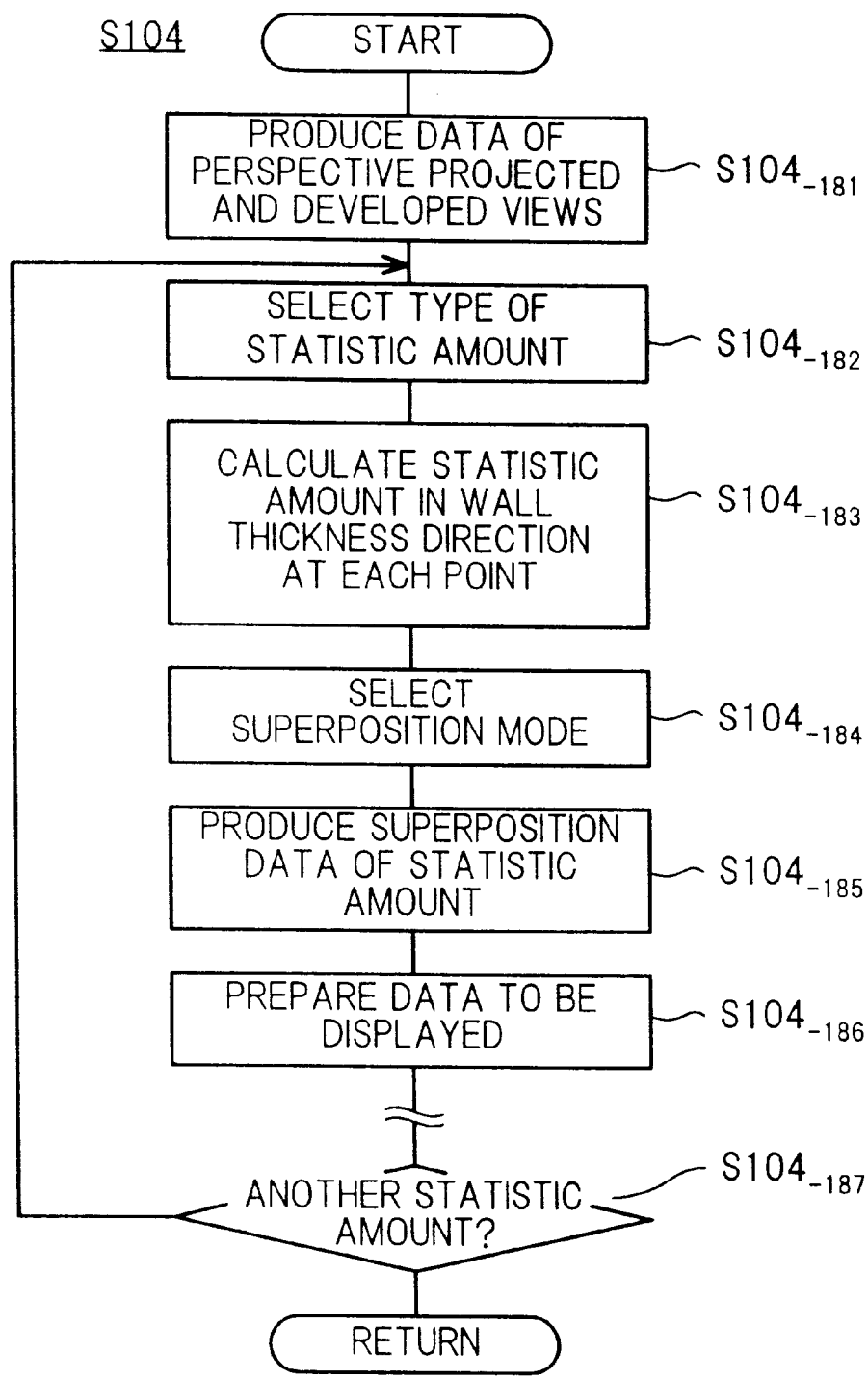
FIG. 59 is a flowchart for producing image data to be displayed in a seventeenth embodiment according to the present invention.

The CPU 120 executes processing to produce data to be displayed, as shown in FIG. 59. Edge data of a perspective projected view along a certain viewing direction and a developed view are formed, then a type of statistic amount to be analyzed regarding intracardiac electrophysiological phenomena is selected (Steps S104–181 and -182). This statistic amount includes averages, maximums, minimums, medians, and standard deviations in the wall thickness direction about excitation onset times (or its relevant amounts) or a myocardial electroaction amount.

Then, a statistic amount whose type has been selected is calculated along the wall thickness direction at each point which corresponds to each of the grid-like intersections virtually set one the ventricular surface (Step S104–183). How the calculated statistic amount is superposed on the projected and/or developed views are determined (selected) interactively with an operator (Step S104–184). As superposition modes for this, like the foregoing, there are provided a contour-line mode, density image mode, and color mode. The analyzed statistic amount data are produced or converted into data adapted to a selected superposition mode, and superposed (Step S104–185 and -186). In these successive processes, another statistic amount may be additionally selected for repeating the same processing.

Figures 60A, 60B, 60C:
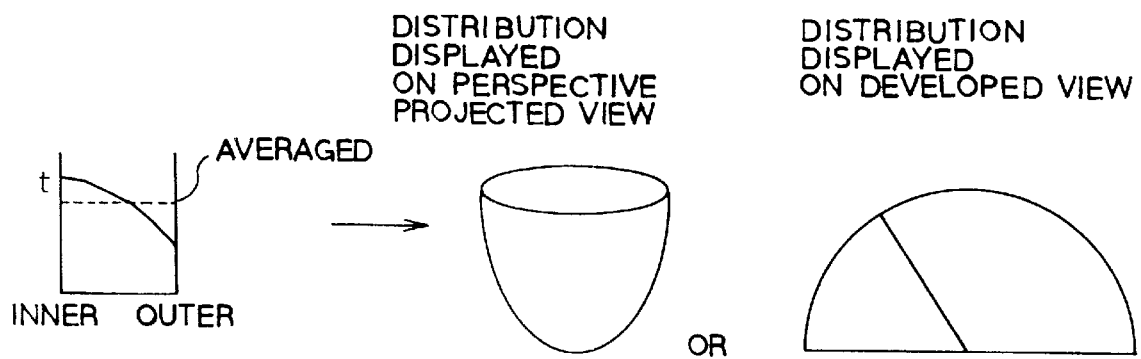
FIG. 60A is an illustration for obtaining a statistic amount.
FIGS. 60B and 60C are displayed images for superposing thereon a statistic amount.

Thus, the analyzed results concerning electrophysiological phenomena are displayed in a desired superposition mode as a two-dimensional distribution image of a statistic amount calculated in the wall thickness direction. For example, an average over excitation onset times t in the wall thickness direction is calculated at each surface position as shown in FIG. 60A, and their averages for two-dimensionally mapped surface positions are tow-dimensionally superposed on either the perspective projected view in FIG. 60B or the developed view in FIG. 60C in a selected superposition mode.

This display processing is nothing to do with the distribution of a statistic amount in the wall thickness direction, it is enough to display only the surface of a projected view or an epicardial developed view. Owing to the fact that it is unnecessary to visualize a plurality of views on the output screen or paper, the number of views to be interpreted is limited to one, simplifying interpretation. In general, there is a fear that lesions existing only within the ventricular wall might be dropped from being observed, if analyzed data distributions are displayed about the ventricular surface. By contrast, this embodiment produces a statistic amount on which electrophysiological phenomena in the inner wall are also reflected, preventing lesions existing in the wall from being dropped out of observation.

Eighteenth Embodiment

Figure 61:
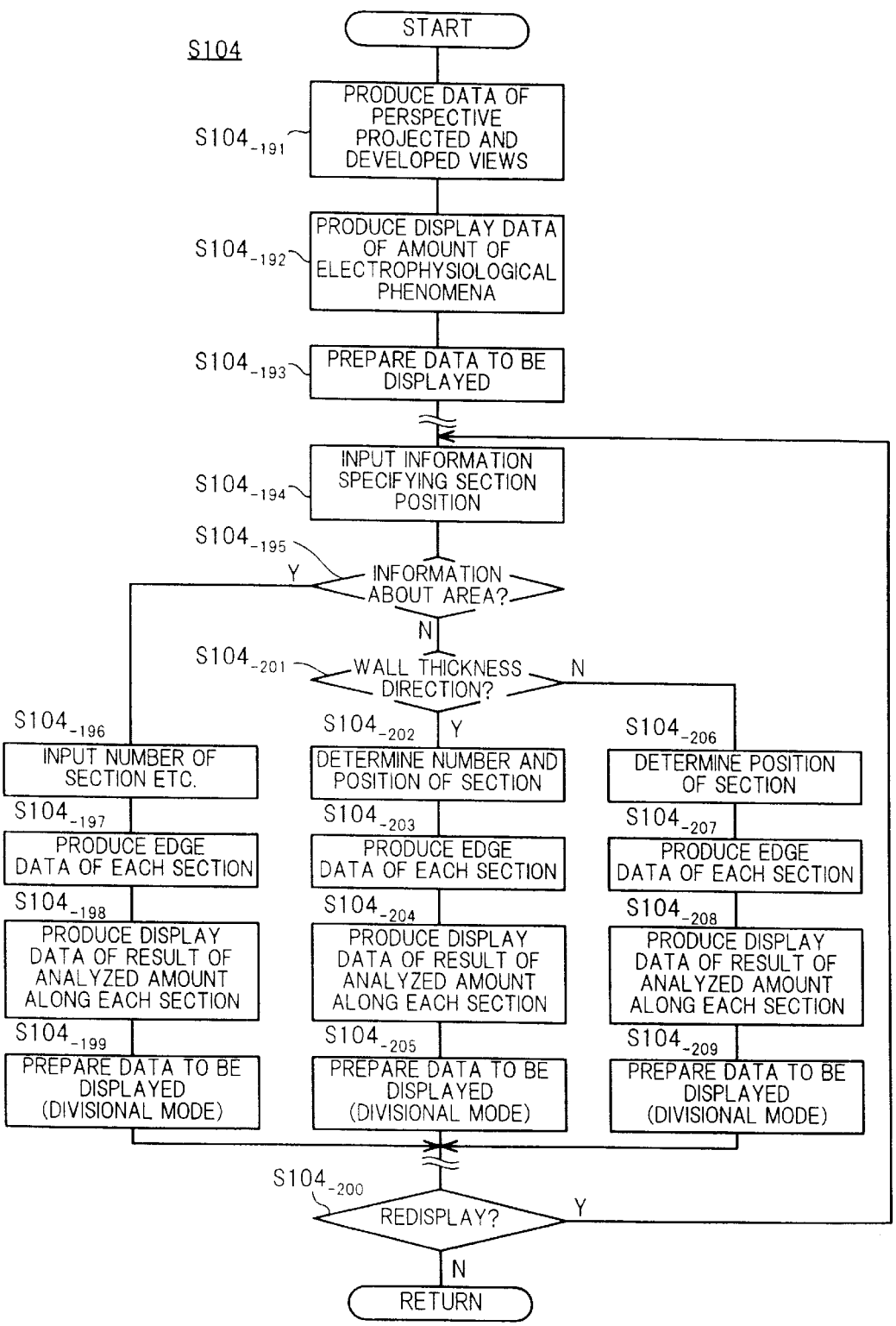
FIG. 61 is a flowchart for producing image data to be displayed in an eighteenth embodiment according to the present invention.
Figure 65:
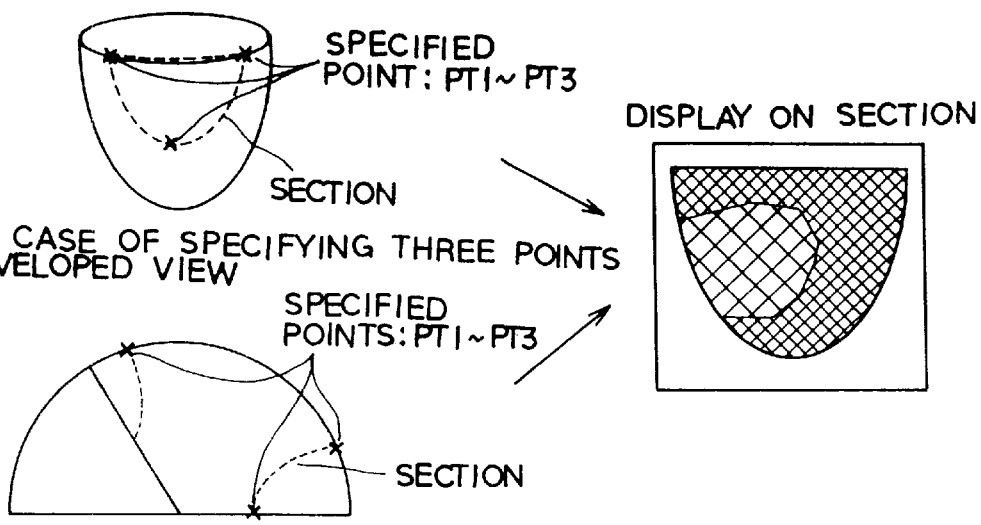
FIG. 65 is an illustration for explaining procedures for display of a specified cross section.

Referring to FIGS. 61 and 65, an eighteenth embodiment of the present invention will be described. In this embodiment, cross sections in agreement with directions specified on a ventricular perspective projected view or developed view are visualized with electrophysiological phenomenon amounts on their cross sections. A wide variety of variations are prepared for setting cross sections.

FIG. 61 outlines processing to produce data to be displayed, which is executed by the CPU 120. First, edge data of a perspective projected view along a given viewing direction and edge data of a given developed view of a desired ventricular portion are produced, then isochrone chart data of excitation onset times and/or density image data of a myocardial electroaction amount are produced (Step S104–191 and -192). These data, which are to be superposed, are produced to help an operator search a clinically interesting region on a displayed image. These data are therefore superposed on the edge data, and displayed (Step S104–193, Step S105 in FIG. 16).

For example, an isochrone chart is superposed on a ventricular projected view, while a density image of an action amount is superposed on a developed view, both the views being displayed on the same screen in parallel. In order to have cross sections of interesting regions displayed, an operator observes the displayed image and input through the operation panel 117 information specifying sections (Steps S104–194 and -195). As this information, prepared are a circular region CR (refer to FIG. 62) and points PT (a pair of PT1 and PT2, or a set of PT1 to PT3; refer to FIGS. 63 to 65). Information according to the points is classified into a first group that sets the sectional direction in the ventricular wall thickness direction (information based on one or two points) and a second group that set it in an arbitrary direction for the cardiac muscle (information based on three points).

Figure 62:
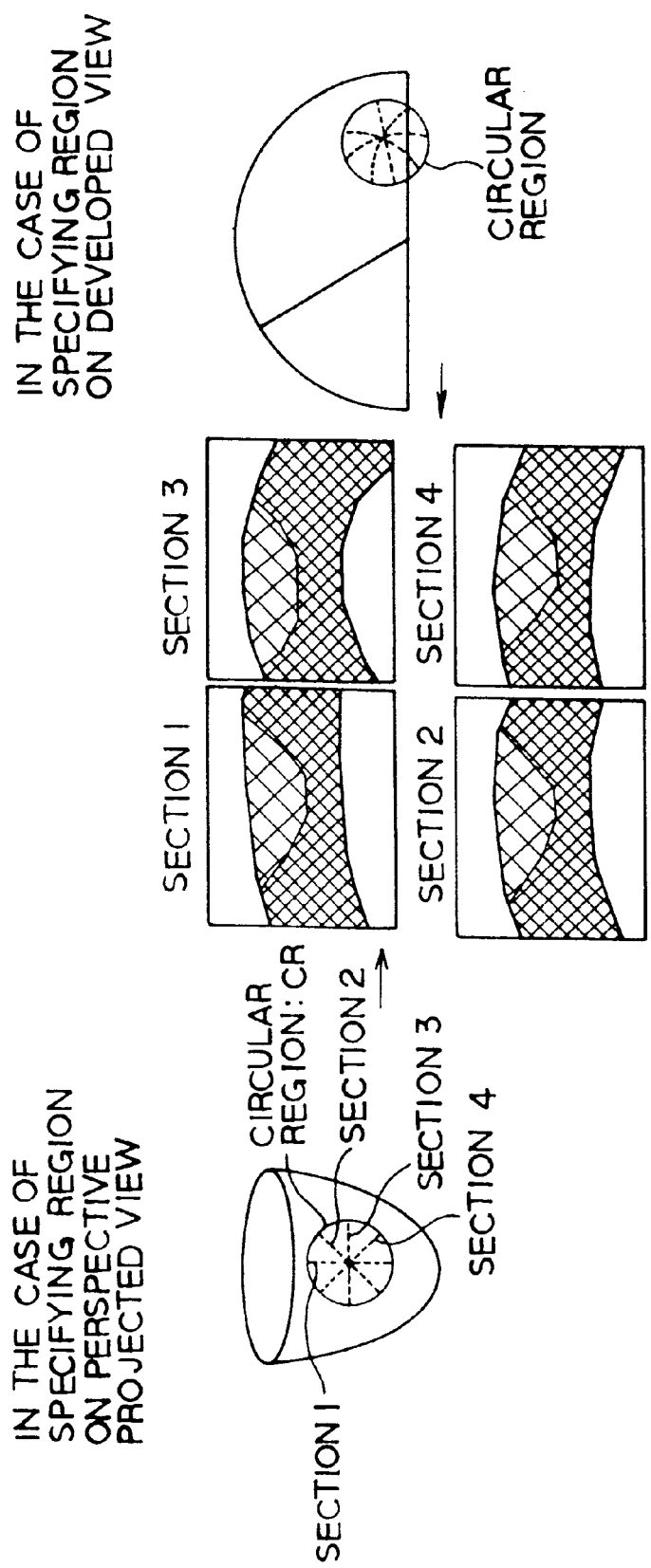
FIG. 62 is an illustration for explaining procedures for display of specified cross sections.

Thus, whether the section-specifying information is regional information or not (i.e., circular region or point(s)) is determined (Step S104–195). When the information is regional one (circular region), Steps S104–196 to -199 are processed in turn. One example is shown in FIG. 62, where a circular region CR is specified on a projected developed view. In response to this, four cross sections extending along four lines in the wall thickness direction are specified, which are divided into equal angular intervals as shown by dashed lines within the circular region CR, and edge data of each cross section are produced (Steps S104–196 and -197). Data indicative of electrophysiological phenomena caused on each cross section are produced using the analyzed results, and displayed (Steps S104–198 and -199). The cross sections are displayed in a divided display mode with characters placed in the neighborhood of the projected or developed view, expressing "section 1, section 2, section 3, section 4", as shown in FIG. 62. The sectional display is not limited to the divided display mode, such as display in a separate screen from the projected or developed view.

Since a plurality of cross sections differently oriented from each other can be displayed with one time of region specification, operation efficiency is excellent. It is also excellent in that local lesions can be observed in detail in terms of its sizes and spread. For example, the progress of myocardial infraction can be read readily.

Whether or not the above sectional display is repeated for another position or display mode is additionally determined, and if being repeated, the processing is returned to Step S104–194 (Step S104–200).

On one hand, the determination is NO at Step S104–195 (point information), if the sectional direction is the wall thickness direction or not is determined from the number of the specified points (Step S104–201). In this embodiment, when the number is one or two, the sectional direction is set to the wall thickness direction, while the number is three, the sectional direction is set to an arbitrary direction in agreement with the three specified points. If determined as the wall thickness direction (one or two specified points), the number of cross sections and their positions are decided, before edge data of the cross sections are produced, data to be displayed of electrophysiological phenomenon amounts residing along each cross section are produced, the data to be displayed are prepared, and the cross sections are displayed separately from the other views(Steps S104–202 to -205, Step S105 in FIG. 16).

Figure 63:
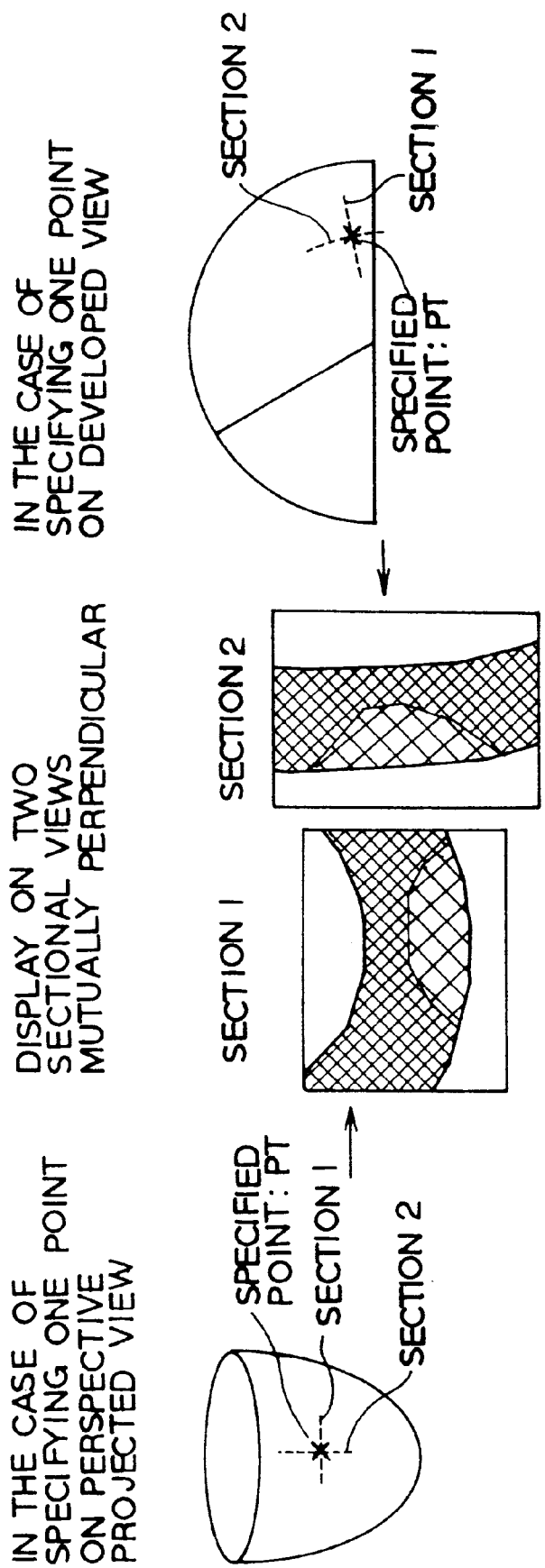
FIG. 63 is an illustration for explaining procedures for display of specified cross sections.
Figure 64:
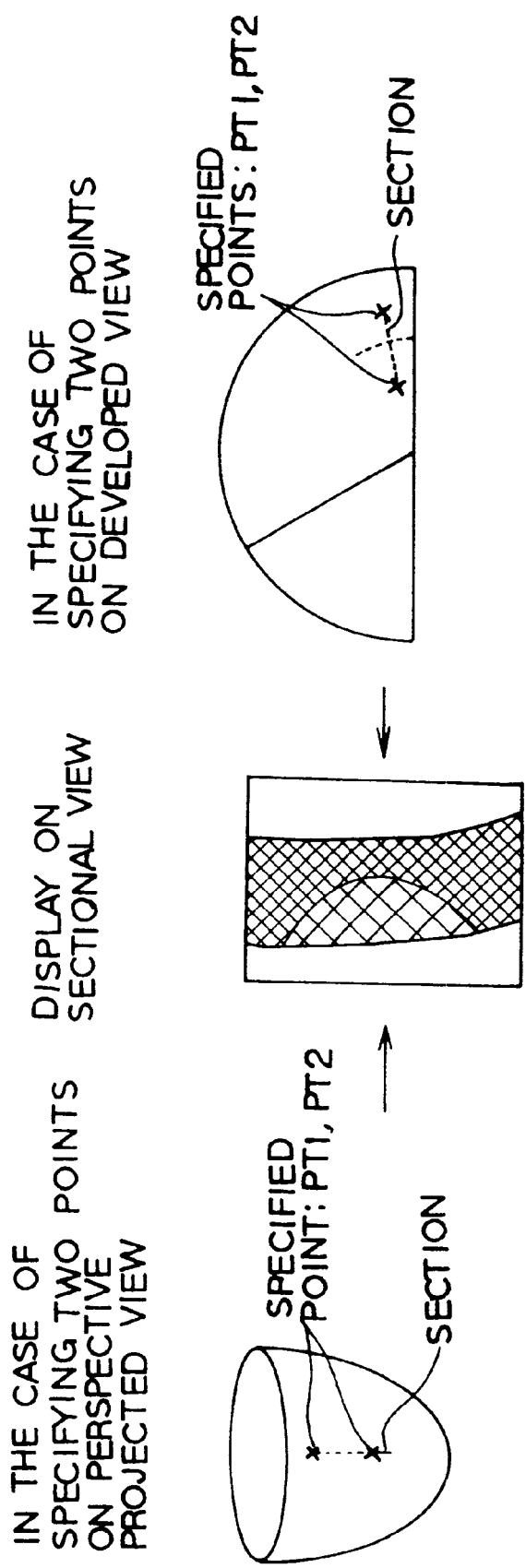
FIG. 64 is an illustration for explaining procedures for display of a specified cross section.

For example, as shown in FIG. 63, in cases a one point PT is specified on a projected or developed view, displayed cross sections pass the specified point PT, are perpendicular to the ventricular surface, and intersect at 90 degrees to each other. On one hand, as shown in FIG. 64, two points PT1 and PT2 are specified on a projected or developed view, a displayed cross section passes the specified points PT1 and PT2 and is almost perpendicular to the ventricular surface. For displaying either one cross section or two cross sections, these, as shown in FIG. 63 or FIG. 64, the same display as in FIG. 62 is performed.

If NO at Step S104–201 determination (i.e., three specified points, so arbitrary sectional direction), as shown in FIG. 65, a single sectional position passing the three points is calculated. Like the foregoing, for the single cross section, edge data are produced, data to be displayed of electrophysiological phenomenon amounts residing along the section are produced, the data to be displayed are prepared, and the cross section is displayed separately from the other views (Steps S104–206 to -209, Step S105 in FIG. 16). The three specified points may be specified on either projected or developed view.

Accordingly, the forgoing display of one or more cross section excludes complicated operation, such as rotation of the ventricles and movement of lines, which is necessary for displaying arbitrary cross sections. Only setting one, two three points on either a projected or developed view according to desired sectional positions enables display of cross sections at any positions, with an easy to operate manner.

Nineteenth Embodiment

Referring to FIG. 66, a nineteenth embodiment of the present invention will be described. In this embodiment, the ventricles are divided into a plurality of segments, a representative value (such as an average) of results of an electrophysiological phenomenon amount is computed for each segment, and the representative values are displayed in a table.

The CPU 120 executes the following processing at Step S104 in FIG. 16. First, a ventricular model is divided into, by way of example, three segments of a right ventricle free wall, septum, and left ventricle free wall, each segment is further divided into its anterior and posterior sides, and those six segments are each divided into a cardiac base side and apex side, thus forming twelve segments in all. For each of the twelve segments, an average, maximum and minimum over a certain period of excitation onset times and action potential amplitudes are computed. The computed results are displayed by the monitor 115 or printer 116 in a table, as exemplified in FIG. 66.

FIG. 66 shows one example of such table display, where averages of action potential amplitudes (uppermost), maximums thereof (middle), and minimums (lowermost) are practically computed for twelve segments and listed. Such display with a table enables an easier quantitative understanding of analyzed results.

This kind of table display or output is not restricted to the case of action potential amplitudes, other amounts are also available. Only one or more values selected from averages, maximums and minimums may be table-displayed.

Twentieth Embodiment

Figure 67:
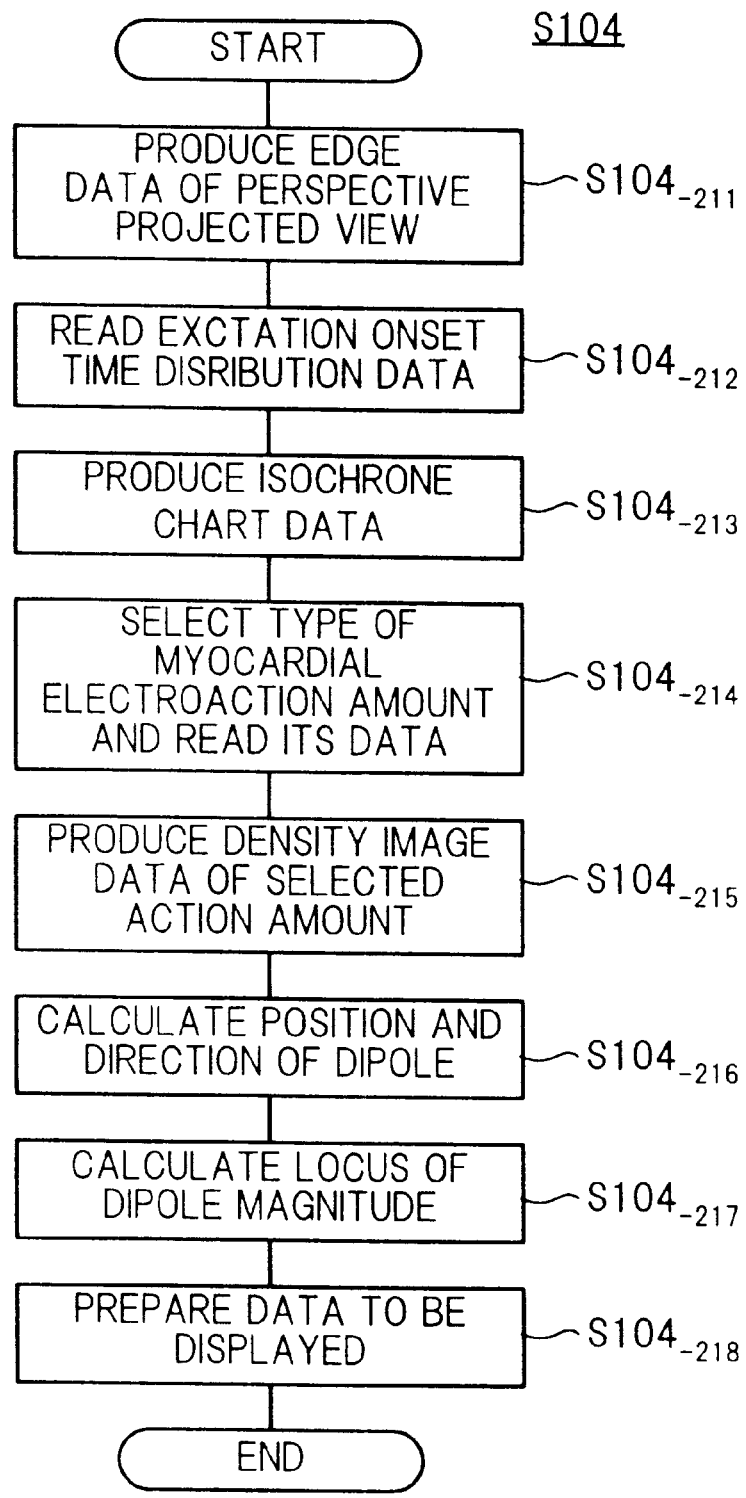
FIG. 67 is a flowchart for producing image data to be displayed in a twentieth embodiment according to the present invention.
Figure 68:
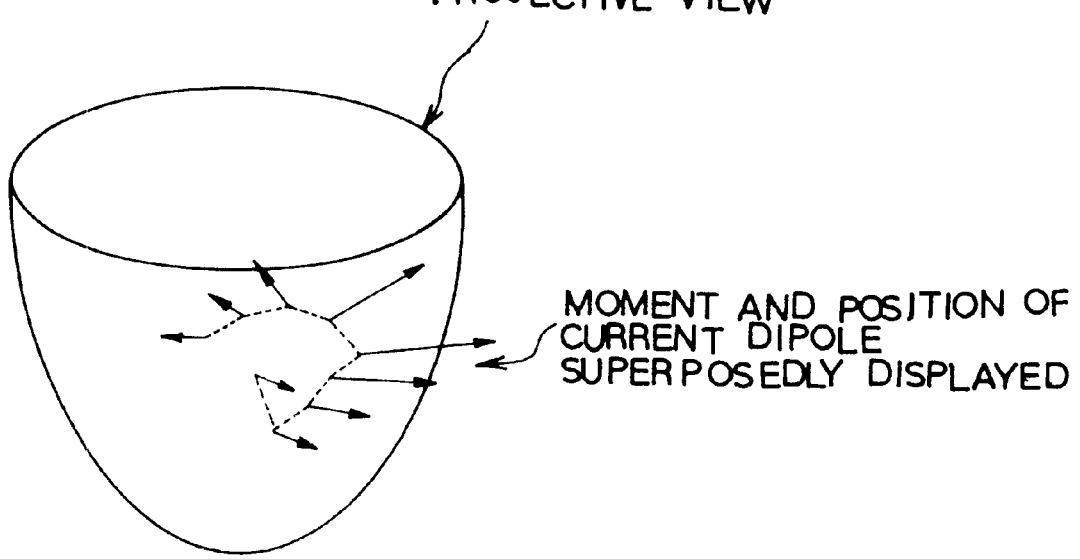
FIG. 68 is an illustration for display using dipoles.

Referring to FIGS. 67 to 68, a twentieth embodiment of the present invention will be described. A feature of this embodiment is that, in addition to superposition display of excitation onset time distributions and/or myocardial electroaction amount distributions, positions, directions and magnitudes of current dipoles inferred using the single dipole method are further superposed.

In FIG. 67 of which steps performed by the CPU 120, edge data of a projected perspective projected view having a given viewing direction toward the ventricles are formed, then isochrone data of an excitation onset time distribution and density image data representing a myocardial electroaction amount distribution are produced (Steps S104–211 to -215). Using the known single dipole method, current dipoles are inferred, and their positions and directions are calculated (Step S104–216). Then loci made up of the magnitudes of the dipoles are calculated (Step S104–217). The loci are obtained by projecting arrows along the same viewing direction as the projected view, and arranging those projections in the temporary order, the arrows standing at dipole positions inferred from potential distributions or flux distributions acquired at several time instants in a predetermined interval during a QRS interval. Then, the isochrone chart data and density image data are superposed on the edge data of the projected view, and concurrently, graphic data such as dashed line and arrows indicating the dipole positions and moments are further superposed (Step S104–218). The data thus-prepared are set out at Step S105 in FIG. 16.

FIG. 68 shows one such display. Although not shown, the isochrone chart and density image are superposed on the ventricular projected view. On the projected view, the dipole positions are expressed by a dashed line, whereas the dipole magnitudes (moments) by arrows, both being superposed on loci representing temporal changes.

On the projected view, either of the isochrone chart or the density image may selectively be superposed.

Since the dipole positions and directions are superposed on the distribution images of electrophysiological phenomena, those two types of information can be used in a complementary manner, providing an easy understanding of positional relationship between them. For example, early excitation regions can be observed with the loci based on the single dipole method, whereas the spread of excitation caused after the early excitation can be the excitation onset time distribution. This manner provides interpretation and diagnosis performed from a variety of aspects.

Twenty-first Embodiment

Referring to FIGS. 69A–69C to 71A and 71B, a twenty-first embodiment of the present invention will be described. In this embodiment, the ventricles partly cut out are displayed as a projected view on which various data indicating electrophysiological phenomena are superposed.

Figures 69A, 69B, 69C:
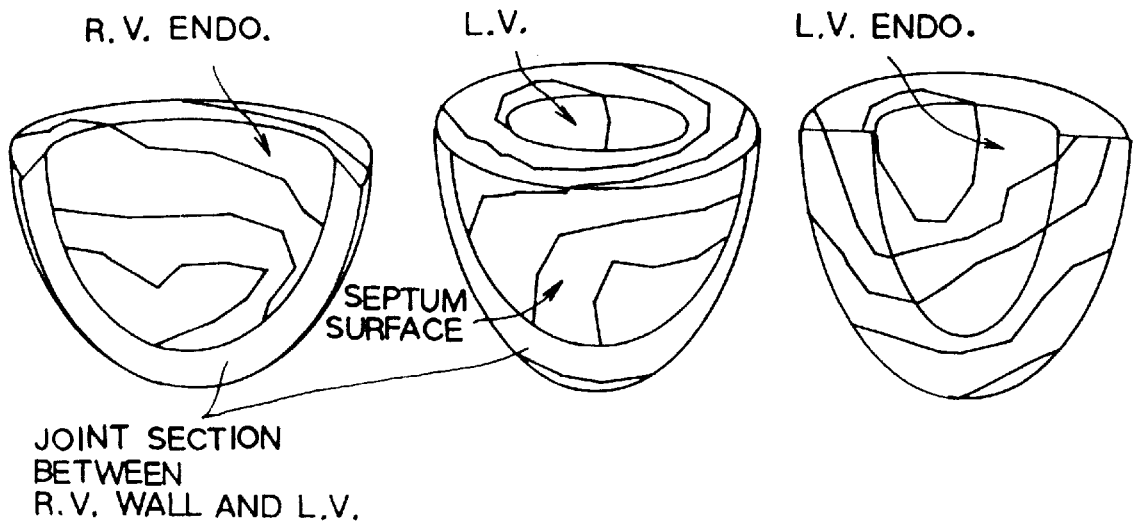
FIGS. 69A to 69C are first display examples according to the twenty-first embodiment of the present invention.

FIGS. 69A to 69C show one such display. In order to realize such display, the CPU 120 executes the following processing at the step to produce data to be displayed (Step S104 in FIG. 16). Firstly, a known viewing direction for a projected view is initially acquired, or a viewing direction is set interactively with an operator. Edge data of an entire ventricular model data, which is viewed along the set viewing direction, are produced from a ventricular shape model. Then, a partial ventricular region which is to be cut out is determined interactively with an operator, and three-dimensional edge data expressing the remaining ventricular region from which the partial region are cut out are produced. Then, data of electrophysiological phenomena, which are to be superposed on a projected view of the remaining region are produced. Finally the produced phenomenon data are superposed on the remaining three-dimensional edge data, and the superposed data are converted into a two-dimensional view in agreement with the viewing direction which has been set, providing data to be displayed.

As a result, as shown in FIG. 69A to 69C, it is allowed to selectively display various ventricular views of which three-dimensional partial regions have been cut out, respectively. In FIG. 69A, the right ventricle is partially cut to show its inner wall. In FIG. 69B, the right and left ventricles are separated by cutting to show the left ventricle side of the septum surfaces. In FIG. 69C, the left ventricle is longitudinally cut to show its inner wall.

The partial cutting of the ventricles makes it possible to understandably represent analyzed results indicating electrophysiological phenomenon on even its inner side wall which has been difficult to be observed by projected views. This enhances interpretation and diagnostic performance.

Figures 70A, 70B:
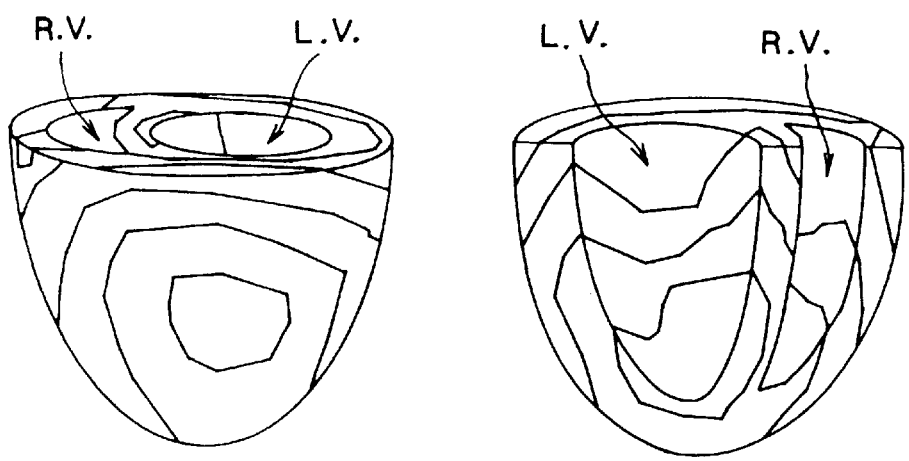
FIG. 70A and 70B are second display examples according to the twenty-first embodiment of the present invention.

A second display is shown in FIGS. 70A and 70B. The CPU 120 executes the following outlined processing at the step to produce data to be displayed (Step S104 in FIG. 16). The ventricles are displayed as a projected view being observed along a given or set viewing direction, as in FIG. 70A. On this projected view, an isochrone chart of an excitation onset time distribution and/or a density image of a myocardial electroaction amount are superposed. The ventricles are then cut along a plane at a given position or set position almost perpendicular to the viewing direction. The frontal portion which has been cut out are projected using an inverted viewing direction to produce three-dimensional edge data. On this edge data, the isochrone chart data and/or density image data are superposed, and displayed as in FIG. 70B. It is preferred that the partially-cut ventricles are displayed in parallel with the not-cut projected view. According to the partially-cut ventricles positioned back to front, its rear, that is, the endocardium surface can well be observed.

Comparing the not-cut view with the partially cut view visualizes any position on the ventricles as well as enhances diagnostic performance.

Figure 71A:
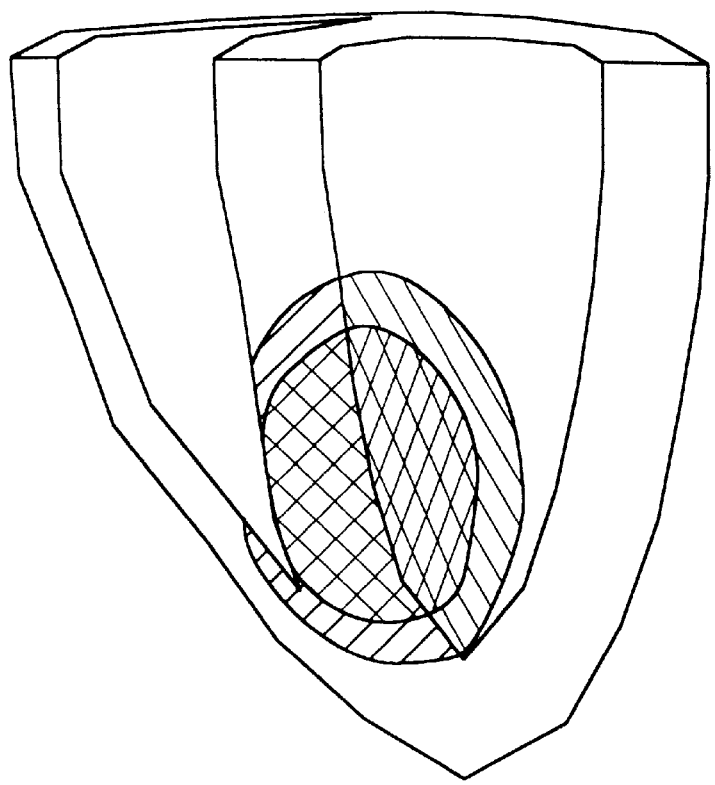
FIGS. 71A and 71B are third display examples according to the twenty-first embodiment of the present invention.
Figure 71B:
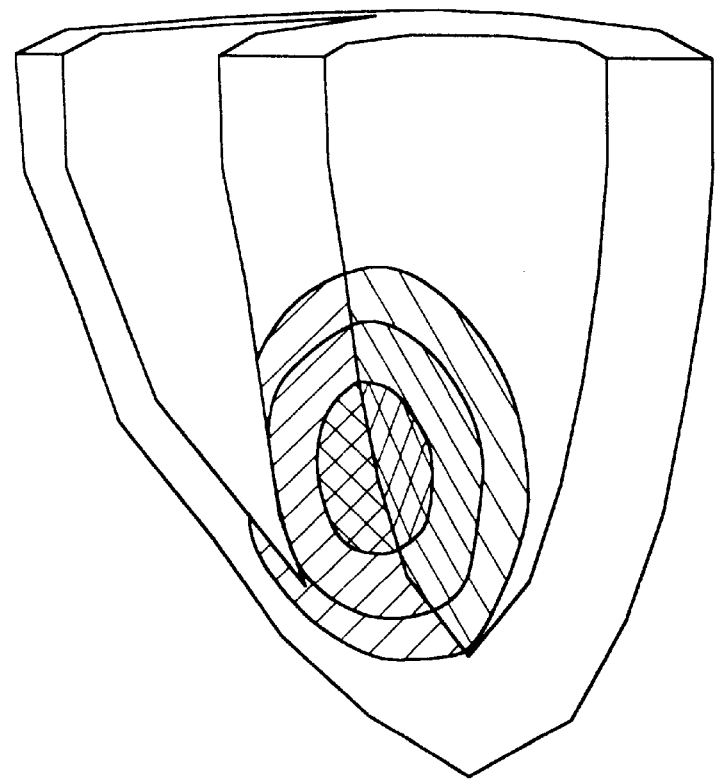

FIGS. 71A and 71B show a third display configuration where a density image superposed on partially-cut ventricles which undergoes the foregoing processing. Although FIGS. 69A–69C and 70C have been described about superposing an isochrone chart on a partially-cut ventricle(s), the superposition of the density image of potential can broaden the coverage of this display.

Twenty-second Embodiment

Figure 72:
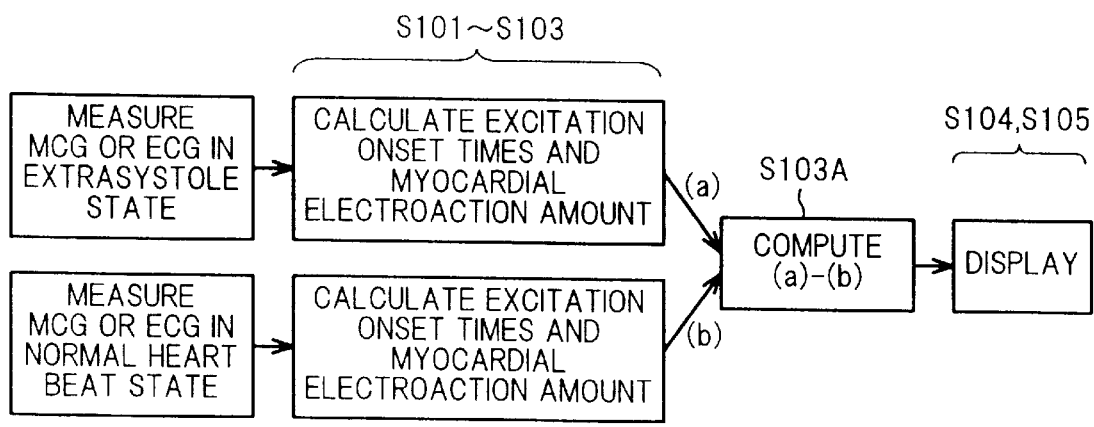
FIG. 72 is a schematic flowchart of a first example carried out to produce data to be displayed in a twenty-second embodiment of the present invention.
Figure 73:
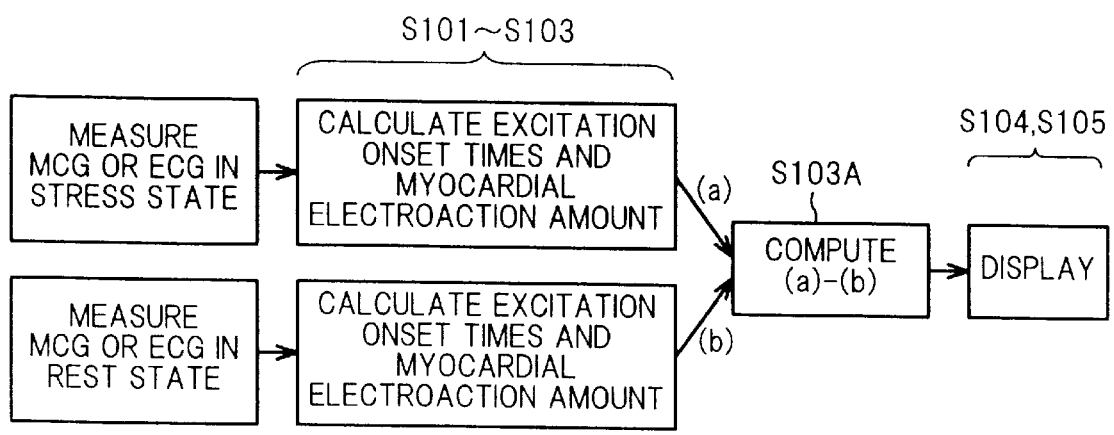
FIG. 73 is a schematic flowchart of a second example carried out to produce data to be displayed in the twenty-second embodiment.

Referring to FIGS. 72 and 73, a twenty-second embodiment will be described. A feature of the embodiment is to visualize differences between analyzed results of two types of sets of an electrophysiological phenomena (such as excitation onset times and/or a myocardial electroaction amount) based on electrocardiogram(ECG) data or magnetocardiogram (MCG) data acquired from the same patient.

A first display example of this embodiment is realized based on processing schematically shown in FIG. 72. That is, excitation onset times and a myocardial electroaction amount are analyzed using MCG data or ECG data acquired from a patient who is in a normal heart beat state (analyzed result (a)). Also the same tow amount items are analyzed using MCG data or ECG data acquired from the same patient who is in an extrasystole state(analyzed result (b)). This analysis is performed by the CPU 120 in parallel or serial as Steps S101 to 103 in FIG. 16.

Both the analyzed results (a) and (b) are subjected to difference calculation by the CPU 120 (Step S103A). The difference calculation is performed, with both ventricular models positioned to each other, every vertex of both the models for each type of electrophysiological phenomena. Therefore, differences "(a)–(b)" between the excitation onset time distributions and another differences "(a)–(B)" between the myocardial electroaction amount distributions are calculated type by type.

The differences "(a)–(b)" of the time distributions are formed into, for example, an isochrone chart data, whereas the differences "(a)–(b)" of the electroaction amount distributions are formed into, for example, a density image data. The formed isochrone chart data are superposed on, for example, a ventricular projected view, whereas the formed density image data are superposed on, for example, a ventricular developed view. This display processing is carried out by the CPU 120 correspondingly to Steps S104 and S105 in FIG. 16. As a result, by way of example, a isochrone chart expressing differences in excitation onset time distributions between the normal heart beat and extrasystole states are superposed on a projected image. Concurrently a density image expressing differences in myocardial electroaction amount distributions between the normal heart beat and extrasystole states are superposed on a developed image.

This display automatically provides information about troubles in myocardial electroaction in extrasystole of the same patient.

A second display example of this embodiment is performed with processing schematically shown in FIG. 73. In this example, the foregoing difference calculation is performed with a combination of an excitation onset time distribution and myocardial electroaction amount distribution analyzed in a rest heart beat state of a patient and another excitation onset time distribution and myocardial electroaction amount distribution analyzed in a stressed beat state of the same patient, and the display is also done in the same way as in the first example.

The amount analyzed at Steps S101 to S103 may be either the excitation onset time distribution or the myocardial electroaction amount distribution.

Twenty-third Embodiment

Figure 74:
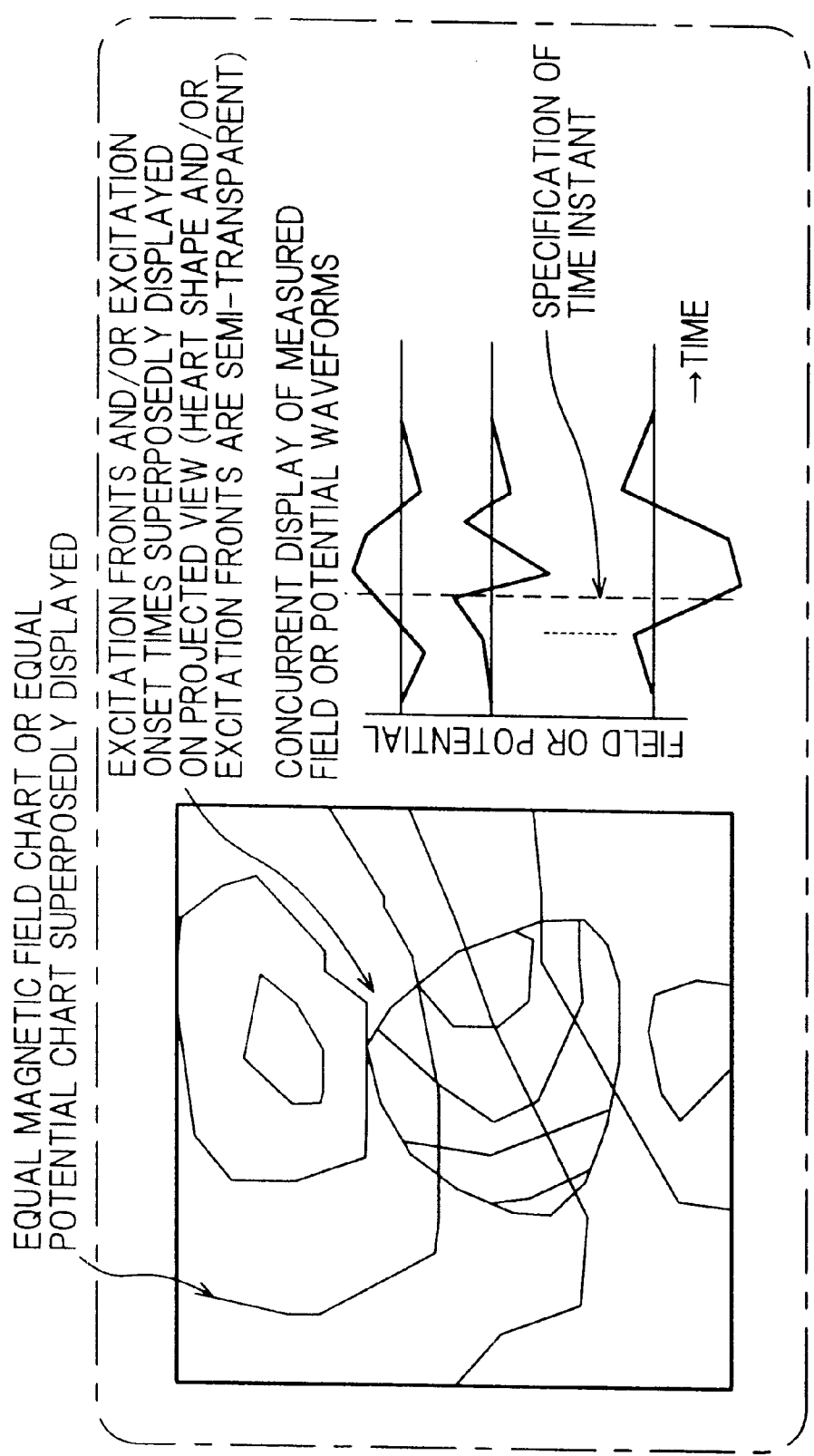
FIG. 74 is an example of a displayed image according to a twenty-third embodiment of the present invention.

Referring to FIG. 74, a twenty-third embodiment of the present invention will be described. This embodiment has a feature that MCG or ECG waveforms used to analyze distributions of electrophysiological phoneme are displayed concurrently with the analyzed results.

This display processing is carried out by the CPU 120 at Step S104 in FIG. 16.

In a display example shown in FIG. 74, analyzed results are displayed on a projected image, and MCG temporal waveforms (ECG waveforms) used for analysis are also displayed. In order to maintain an accurate positional relationship for display between MCG (or ECG) and a ventricular model, the same coordinate system is given the MCG (or ECG) and the model and the same viewing direction are used for projection in both of them.

Furthermore, in FIG. 74, on the MCG (or ECG) waveforms displayed together, a dashed line is placed longitudinally to specify a time instant. In response to the time instant specified by this line, the projected MCG (or ECG) view is updated.

It is preferred that the shapes of excitation fronts at the same specified time instant is displayed as a projected view. By this, the relationship between a magnetic field distribution (or potential distribution) and excitation fronts can precisely be observed.

Twenty-fourth Embodiment

Figure 75:
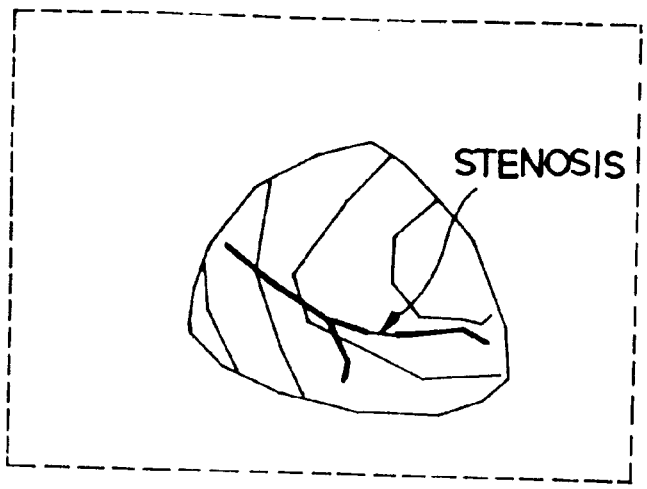
FIG. 75 is an example of display according to a twenty-fourth embodiment of the present invention.
Figure 76:
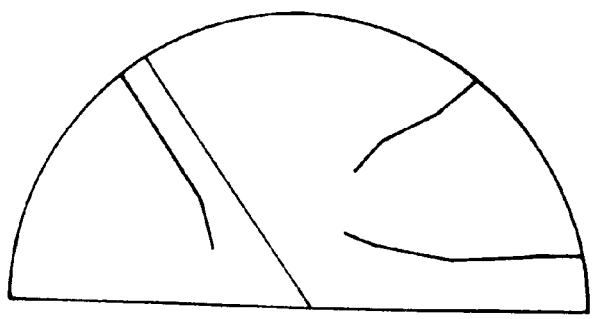
FIG. 76 is another example of display according to the twenty-fourth embodiment.

Referring to FIGS. 75 and 76, a twenty-fourth embodiment of the present invention will be described. This embodiment has a feature that vessel-enhanced images acquired by clinical imaging modalities, such as an X-ray system, X-CT scanner, diagnostic ultrasound apparatus, or MRI system, and analyzed results of at least one of distributions of excitation onset times and a myocardial electroaction amount are superposedly displayed.

The display processing is carried out by the CPU 120 correspondingly to Step S104 in FIG. 16.

FIG. 75 shows one display example. When an X-ray image and distributions of excitation onset times and a myocardial electroaction amount are mutually superposed, a viewing point for displaying a ventricular model is placed at an X-ray source. When the superposition is made with an ultrasound image (for example, ultrasound Doppler image), projection for producing a projected view is performed such that an ultrasound scanning section and a projected view plane becomes parallel. This causes analyzed results to be superposedly displayed on the same section as the ultrasound image. In the case of CT or MRI images, the images are three-dimensionally reconstructed, and projected in the same manner as a ventricular model. When projecting CT or MRI vessel-enhanced images, it is preferred that only the surface and its neighboring vessels, which can be seen when projecting a ventricular model, are projected. This projection can exclude vessels in the rear side of the model from being displayed, providing images easy to read.

FIG. 76 illustrates an example in which vessel-enhanced images are superposedly displayed on a developed view of a ventricular model. Three-dimensionally reconstructed images based on data acquired from MRI systems or CT scanners are used. A three-dimensional image including vessels is transferred in coordinate system into a ventricular model, each vexel of the three-dimensional image is calculated within the model. If each voxel position exists within a predetermined range from the ventricular surface, the voxel position is projected in the perpendicular direction to the ventricular surface move the position thereon. Next, using the same manner as in developing the ventricular surface, positions on the developed view are obtained depict the positions thereon.

According to this embodiment, vessel-enhanced images are superposed on a ventricular projected or developed view, and analyzed results are also superposed thereon. It is therefore possible to readily grasp the relationship between lesions in the distributions and the coronary artery. For example, if action potentials around peripherals of stenosis are lowered, it is easy to understand that the lowerd action potentials results from the stenosis.

Twenty-fifth Embodiment

Figure 77:
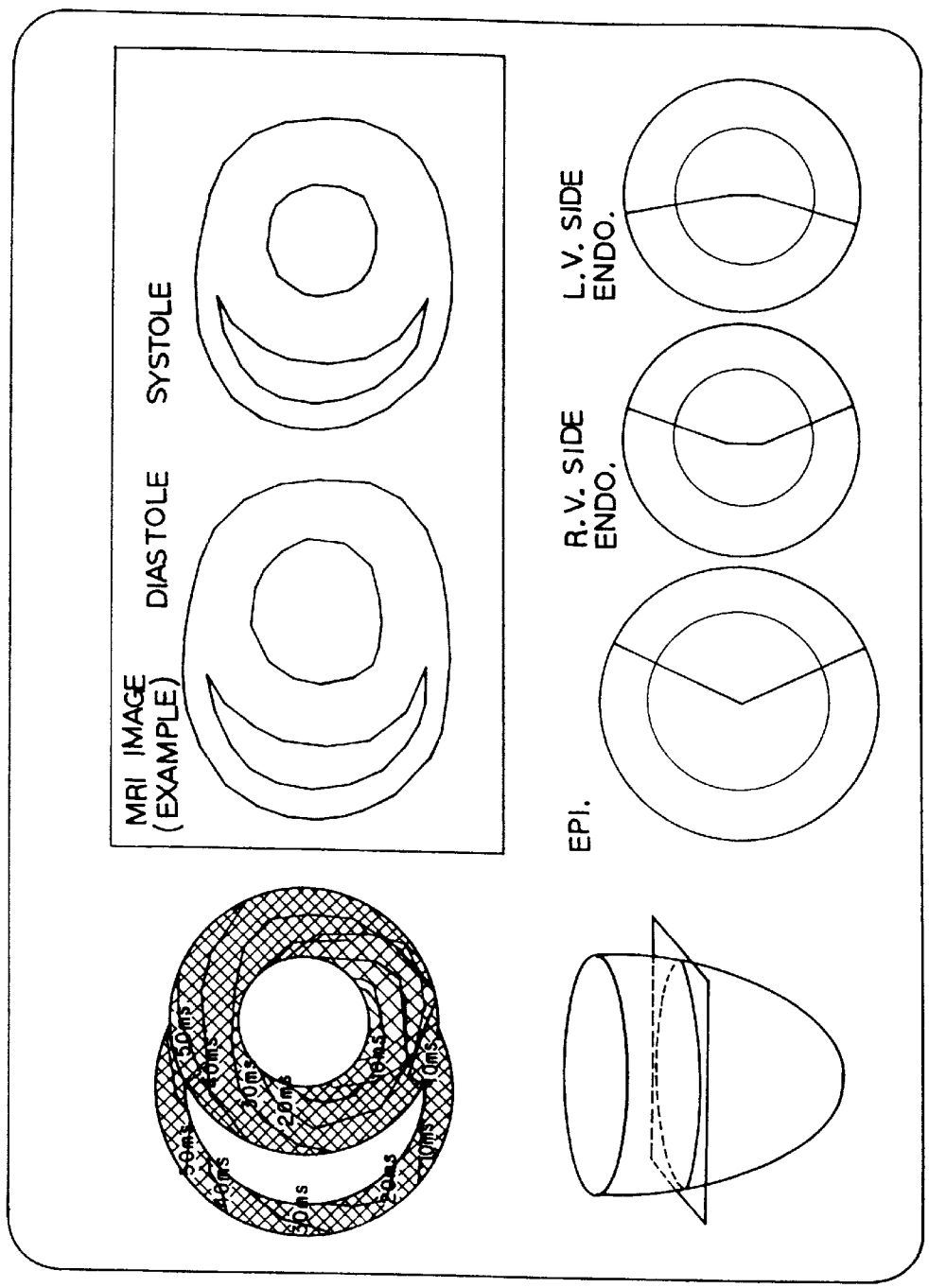
FIG. 77 is an example of display according to a twenty-fifth embodiment of the present invention.
Figure 78:
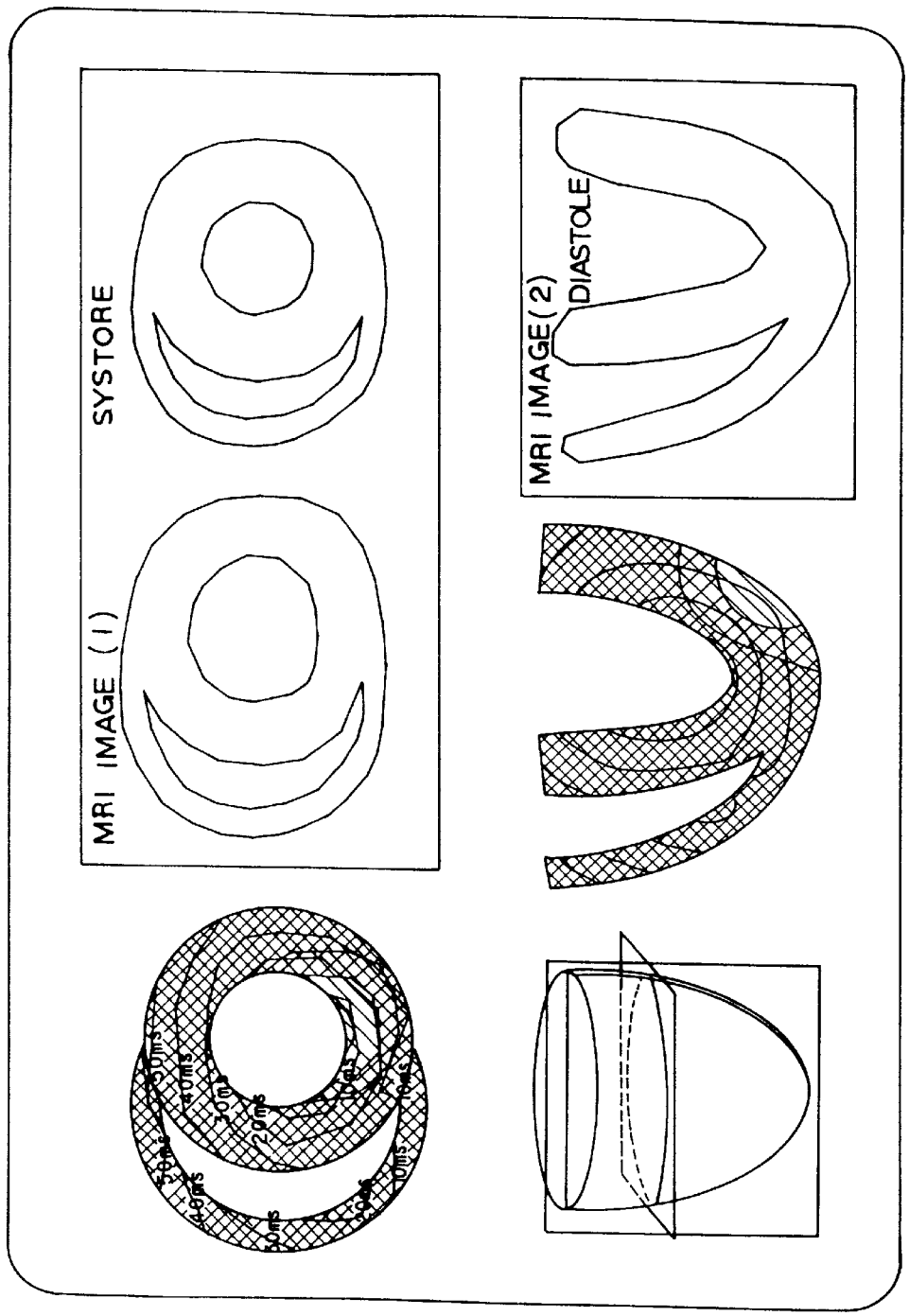
FIG. 78 is another example of display according to the twenty-fifth embodiment.

Referring to FIGS. 77 and 78, a twenty-fifth embodiment of the present invention will be described. In this embodiment, images in which analyzed results are superposed on a sectional view, projected view, and/or developed view and tomographic images acquired by clinical imaging modalities such as MRI systems, CT scanners, or diagnostic ultrasound apparatus are concurrently displayed.

The display processing is carried out by the CPU 120 correspondingly to Step S104 in FIG. 16.

FIG. 77 shows on display example. In this example, both images displayed on a ventricular sectional view, projected view, and developed views, and tomographic images acquired by an MRI system are displayed concurrently. Located at a lower left, upper left, lower right, and upper right are a projected view, a minor-axis sectional view, a plurality of types of developed views, and MRI tomographic images at end-diastole and end-systole. On the sectional image, an isochrone chart of an excitation onset time distribution is superposed, for example. On the projected view, a section is superposed to show the position of the minor-axis sectional view. On the developed views, density images of a myocardial electroaction amount distribution are superposed. Further, on the MRI tomographic images, a myocardial electroaction amount distribution may be placed.

When an operator specifies an arbitrary section on the projected, a minor-axis cross section positionally corresponding to the specified section is displayed. It is possible to select the same minor-axis cross section in sectional position as the MRI tomographic image section. The MRI tomographic images are arranged in parallel to show end-diastole and end-systole images as dynamic images or frozen images, or to show those images in a switching system. This enables examination of troubles in diastole or systole on the MRI images as well as examination of lesions in the ventricles using an excitation onset time distribution and a myocardial electroaction amount distribution displayed on the same sections as the MRI images. At the same time, a positional relationship between the MRI images and the distribution images can be examined. Moreover it is also possible that the MRI images and the distribution images are superposedly displayed to show a clearer positional relationship.

FIG. 78 is another display example of this embodiment, where concurrently displayed are both a plurality of MRI images and major-axis sectional views of a plurality of corresponding ventricular models, on which the foregoing distribution(s) are superposed. Such display make it possible to observe lesions of the ventricles from a plurality of cross sections. The remaining features in FIG. 78 are equivalent to those in FIG. 77.

Twenty-sixth Embodiment

Figure 79:
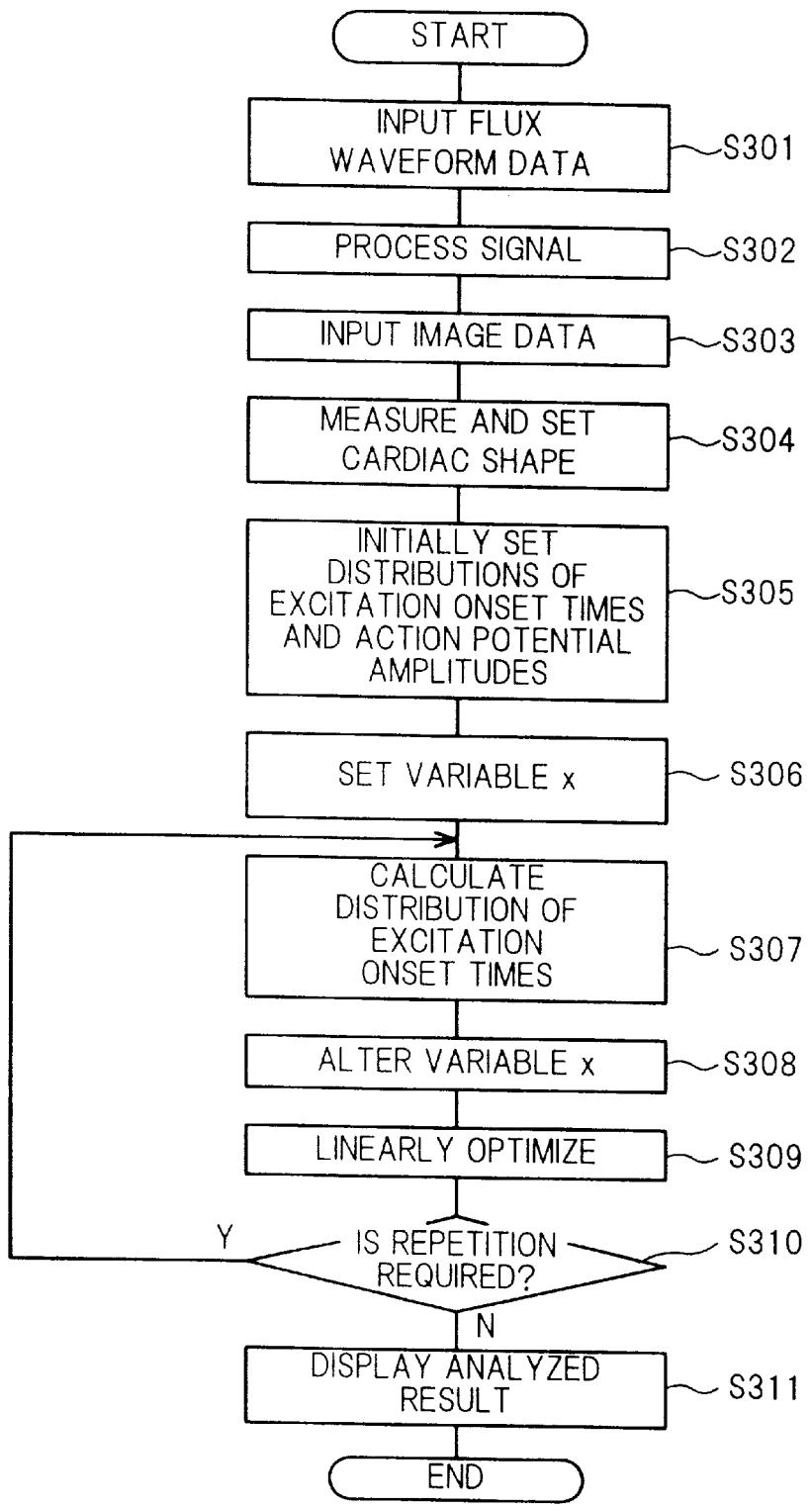
FIG. 79 is a schematic flowchart explaining analysis executed in a twenty-sixth embodiment of the present invention.

Referring to FIG. 79, a twenty-sixth embodiment of the present invention will be explained. This embodiment is concerned with analysis of electrophysiological phenomena, in particular, corresponds to alternative example of the foregoing the third embodiment.

A feature of this embodiment is to incorporate a linear-optimizing step with regard to an action potential amplitude distribution into analysis processing so as to eliminate the need for optimization of a variable y assigned to the action potential amplitude.

In consequence, owing to the face that the number of parameters which should be optimized can be reduced, the repetition times of calculation for simulation can also be lowered, raising efficiency in analysis. Further, introducing a penalty function with regard to the excitation onset time and/or the action potential amplitude can avoid search for distributions undesirable as solutions, contributing to raising efficiency in analysis.

A principle to realize the above object is as follows. In the embodiment, an object function to be optimized is given as the following equations.

$$e' = e + p_t(t) + p_\Phi(\Phi)$$

In this equation, "e" is an error described with the foregoing equation (3), $\Phi$ is a vector composed by longitudinally arranging an action potential amplitude at each vertex, like t, $p_t(t)$ is a penalty function with regard to the excitation onset time, and $p_\Phi(\Phi)$ is a penalty function with regard to the action potential amplitude. Each penalty function is a function that gets larger values against distributions of excitation onset times or action potential amplitude that are improper as solutions. When t is given and $\Phi$ is solely a variable, an optimum value of e' can be obtained quickly with known linear optimizing methods utilizing there exists an anticipating relationship between the action potential amplitude $\Phi$ and the magnetic waveform. Therefore, an optimum value E(t) of e' is independent from $\Phi$. As a result, setting of an initial value of the variable y, alteration thereof, and others are not necessary. At the same time, the numbers of parameters to be searched can be reduced.

FIG. 79 shows processing carried out by the CPU 120 to achieve the above. Steps S301 to 305 are the same in content as those in FIG. 12 described in the third embodiment. At Step S306, only a variable x concerning the excitation onset time is set. (In this case, a variable is not necessary to be set.) At Step S307, data of an excitation onset time distribution are solely calculated. At Step S308, processing for correcting an excitation onset time distribution is performed such that the foregoing object function E(t) gets smaller. The correction depends on the type of non-linear optimizing algorithm adopted. the excitation onset time t is calculated form the variable x. At Step S309, a linear optimization for $\Phi$ is performed to calculate the foregoing object function E(t). Steps S307 to S309 are repeated in accordance with requests from a non-linear optimizing algorithm adopted (Step S310). Finally at Step S311, analyzed results are displayed.

Although various embodiments have been given for the present invention, it is to be understood that these are illustrative purposed only. Various modifications and adaptations will be readily apparent to those skilled in the art without departing from the scope of the invention. Accordingly it is intended that the invention be limited only by the spirit and scope of the claims appended hereto.

What we claim is:

1. A diagnostic system for intracardiac electrophysiological phenomena, in which the phenomena are inferred based on at least one of a potential obtained from a patient having a heart and a magnetic field obtained from the patient:

inferably analyzing means for analyzing the at least one information so as to obtain a characteristic quantity associated with at least one of a magnitude and an interval of an electroaction in a cardiac muscle of the patient; and visualizing means for displaying the characteristic quantity as a distribution image.

2. The diagnostic system of claim 1, wherein the analyzing means are composed of means for analyzing not only the at least one information so as to obtain the characteristic quantity but also a further characteristic quantity associated with a temporal sequence of excitation of the cardiac muscle, and the visualizing means is composed of means for displaying not only the characteristic quantity as the distribution image but also the further characteristic quantity as a further distribution image.

3. The diagnostic system of claim 2, wherein the characteristic quantity is first information about a distribution of myocardial electroactions consisting of at least one of an action potential amplitude distribution on the cardiac muscle, a conductance distribution of the cardiac muscle, and a current dipole density of the cardiac muscle, and the further characteristic quantity is second information about a propagated excitation process consisting of at least one of an excitation onset time distribution on the cardiac muscle, an excitation conduction velocity distribution on the cardiac muscle, and a divergence distribution of excitation onset times of the cardiac muscle.

4. The diagnostic system of claim 3, wherein the visualizing means has a visualizing apparatus having a visualizing area and means for representing both the first information and second information on the visualizing area of the visualizing apparatus.

5. The diagnostic system of claim 4, wherein the visualizing apparatus is one of an electric monitor, a printing apparatus, and an imaging apparatus with a film.

6. The diagnostic system of claim 4, wherein the representing means is means that represents separately both the first information and the second on the visualizing area of the visualizing apparatus.

7. The diagnostic system of claim 6, wherein the representing means has sectional data producing means for producing cross sectional data of a ventricle of the heart, superposing means for producing image data on which both the first and second information are superposed separately, and outputting means for outputting the image data to the visualizing apparatus.

8. The diagnostic system of claim 7, wherein the representing means has data producing means for producing each of the first information and the second information into one of edge image data, density image data, and colored image data sent to the superposing means.

9. The diagnostic system of claim 8, wherein the data producing means includes means for obtain a local maximum value and a local minimum value for at least one of the first information and the second information, and means for providing the image data positional data indicative of positions of the local maximum and minimum values.

10. The diagnostic system of claim 8, wherein the data producing means consists of means for providing the image data discrete reading data produced in producing the image data of at least one of the first information and the second information.

11. The diagnostic system of claim 4, wherein the representing means is means that represents superposedly both the first information and the second on the visualizing area of the visualizing apparatus.

12. The diagnostic system of claim 11, wherein the representing means has sectional data producing means for producing cross sectional data of a ventricle of the heart, superposing means for producing image data on which both the first and second information are superposed, and outputting means for outputting the image data to the visualizing apparatus.

13. The diagnostic system of claim 12, wherein a cross section of the ventricle is either one of a major axis cross section and a minor axis cross section thereof.

14. The diagnostic system of claim 12, wherein the representing means has data producing means for producing either one of the first information and the second information into one of edge image data, density image data, and colored image data sent to the superposing means.

15. The diagnostic system of claim 14, wherein the data producing means includes means for obtain a local maximum value and a local minimum value for at least one of the first information and the second information, and means for providing the image data positional data indicative of positions of the local maximum and minimum values.

16. The diagnostic system of claim 14, wherein the data producing means consists of means for providing the image data discrete reading data produced in producing the image data of at least one of the first information and the second information.

17. The diagnostic system of claim 4, wherein the representing means includes means for displaying the second information using one of an edge image, a density image, and a colored image.

18. The diagnostic system of claim 4, wherein the representing means includes means for displaying the first information using one of an edge image, a density image, and a colored image.

19. The diagnostic system of claim 4, wherein the representing means includes means for displaying the first information and the second information superposedly one on another.

20. The diagnostic system of claim 3, wherein the visualizing means comprises means for producing one of sectional view data, developed view data, and projected view data of a ventricle of the heart and means for displaying one of the sectional view data, developed view data, and projected view data on which at least one of the first information and the second information is superposed.

21. The diagnostic system of claim 20, wherein the data produced by the producing means is the sectional data produced at an arbitrary sectional position for the ventricle.

22. The diagnostic system of claim 20, wherein the data produced by the producing means is the projected data projected along an arbitrary direction toward the ventricle.

23. The diagnostic system of claim 20, wherein the data produced by the producing means is the developed data produced by developing a ventricular surface of either one of an endocardium and an epicardium of the ventricle.

24. The diagnostic system of claim 3, wherein the visualizing means comprises first producing means for producing either one of minor-axis sectional view data and major-axis sectional view data of a ventricle of the heart, first display means for displaying the produced sectional view data, second producing means for producing sectional view data of the ventricle at a position changeably specified on a sectional image displayed,
   calculating means for calculating distribution information about at least one of the first information and the second information in a cross section corresponding to the specified position, and
   second means for superposedly displaying the sectional view data at the specified position and the calculated distribution information corresponding to the specified position.

25. The diagnostic system of claim 3, wherein the visualizing means comprises first producing means for producing either one of minor-axis sectional view data and major-axis sectional view data of a ventricle of the heart, first display means for displaying the produced sectional image data, second producing means for producing projected view data of the ventricle viewed along a viewing direction changeably specified on the sectional image displayed, calculating means for calculating distribution information about at least one of the first information and the second information on a surface of the ventricle when viewed along the specified viewing direction, and second means for superposedly displaying the projected view data along the specified viewing direction and the calculated distribution information in the specified viewing direction.

26. The diagnostic system of claim 3, wherein the visualizing means comprises producing means for producing projected view data and sectional view data of a ventricle of the heart and display means for concurrently displaying both the projected view data and the sectional view data on which at least one of the first information and the second information are individually superposed.

27. The diagnostic system of claim 26, wherein the sectional view data consist of data of a plurality of cross sections at a plurality of different positions set on a projected view according to the projected view data.

28. The diagnostic system of claim 3, wherein the visualizing means comprises producing means for producing projected view data and the developed view data on which at least one of the first information and the second information are individually superposed.

29. The diagnostic system of claim 28, wherein the developed view data consist of data of developed views at a plurality of different ventricular surfaces set on a projected view according to the projected view data.

30. The diagnostic system of claim 28, wherein the producing means is means that additionally form data of a grid superposed on projected and developed views according to the projected and developed view data, respectively.

31. The diagnostic system of claim 28, wherein the producing means is means that additionally form data of markers including characters, lines, graphics, and arrows superposed on projected and developed views according to the projected and developed view data, respectively.

32. The diagnostic system of claim 28, wherein the visualizing means has means for the projected view data so as to make it visible any position specified on a developed view according to the developed view data.

33. The diagnostic system of claim 3, wherein the visualizing means comprises producing means for producing image data composing a plane passing a specified depth position in a wall-thickness direction of the cardiac muscle, calculating means for calculating information on the plane from at least one of the first information and the second information, and displaying means for displaying the calculated information about the plane.

34. The diagnostic system of claim 33, wherein the specified depth position is either one of an arbitrary selectable position and a previously fixed position.

35. The diagnostic system of claim 34, wherein the plane is a developed view plane of the cardiac muscle.

36. The diagnostic system of claim 3, wherein the visualizing means comprises producing means for producing data indicative of a shape of a ventricle of the heart, first representing means for representing the shape data of the ventricle, specifying means for specifying a desired position on the displayed ventricle image, estimating at least one of the first information and the second information along the wall-thickness direction at the specified position, and second representing means for representing the estimated information.

37. The diagnostic system of claim 36, wherein the ventricular shape is expressed by either one of a projected view and a developed view, and the first and second representing means has a common monitor to represent the ventricular shape and the estimated information thereon.

38. The diagnostic system of claim 3, wherein the visualizing means has estimating means for estimating a two-dimensionally mapped statistic quantity of at least one of the first and second information in a wall-thickness direction of a ventricle of the heart at each position on a two-dimensionally distributed surface of the ventricle, producing means for producing data indicative of a shape of the ventricle, and representing means for representing the ventricle shape data and the two-dimensionally mapped statistic quantity superposed on the ventricle shape.

39. The diagnostic system of claim 38, wherein the statistic quantity is any of an average, minimum, maximum, median, and standard deviation of the distribution information along the wall-thickness direction at each of the points.

40. The diagnostic system of claim 3, wherein the visualizing means comprises first representing means for representing a diagram regarding a ventricular surface of the heart, providing means for providing section-specifying information specifying a sectional position and a sectional direction of the cardiac muscle on the displayed diagram, obtaining a cross section specified with the section-specifying information, calculating means for calculating information distributed along the obtained cross section based on at least one of the first and second information, and second representing means for the cross section and the distributed information superposed on the cross section.

41. The diagnostic system of claim 40, wherein the section-specifying information is information specifying a plurality of cross sections at a time in the wall-thickness direction of the ventricle.

42. The diagnostic system of claim 40, wherein the section-specifying information is information about a point specifying a cross section in the wall-thickness direction of the ventricle.

43. The diagnostic system of claim 40, wherein the section-specifying information is information specifying a cross section in any direction toward the cardiac muscle.

44. The diagnostic system of claim 3, wherein the visualizing means comprises calculating means for calculating a representative value of distributed information concerning at least one of the first and second information in each of a plurality of areas formed by dividing a ventricle of the heart, and representing means for representing the representative value.

45. The diagnostic system of claim 3, wherein the representative value includes any of an average, maximum, and minimum of the distributed information calculated area by area.

46. The diagnostic system of claim 3, wherein the visualizing means comprises means for calculating information about a current dipole causing the magnetic field based on a single dipole approach, means for obtaining data of a diagram indicative of a shape of a ventricle of the heart, and means for representing the shape data on which at least one of the first and second information as well as the current dipole information are superposed.

47. The diagnostic system of claim 3, wherein the visualizing means comprises means for producing data of a projected view for part remaining in a ventricle of the heart, the remaining part being formed by partially cutting out the ventricle, and means for representing the projected view data on which at least one of the first and second information is superposed.

48. The diagnostic system of claim 3, wherein the visualizing means comprises first means for producing data of a first projected view along a viewing direction set toward a ventricle of the heart, second means for producing data of a second projected view formed by not only cutting the ventricle with an approximately perpendicular plane to the viewing direction but also turning around a rear of a frontal cut portion so that the rear of the frontal cut portion becomes a front composing the second projected view, and means for representing at a time the first and second projected data on each of which at least one of the first and second information are superposed.

49. The diagnostic system of claim 3, wherein the analyzing means is composed of performing the analysis to obtain at least one of the first information and the second information with the patient, the analysis being performed for each of different heart beat states, and the visualizing means comprises means for calculating differences between different types of information obtained in the different heart beat states, and means for displaying the differences.

50. The diagnostic system of claim 3, wherein the different heart beat states are either one of a first combination of an extrasystole state and a normal heart beat state of the patient a second combination of a loaded state and a rest state of the patient.

51. The diagnostic system of claim 3, wherein the visualizing means comprises means for representing at a time either one of a temporal waveform and a spatial distribution of information about at least one of the potential and the magnetic field in addition to at least one of the first and second information.

52. The diagnostic system of claim 51, wherein the representing information comprises a member for displaying an excitation front at an arbitrarily specified time on a projected view image.

53. The diagnostic system of claim 3, wherein the visualizing means comprises means for producing image data indicative of a shape of a ventricle of the heart and means for representing the image data of the ventricular shape on which at least one of the first and second information and a blood vessel enhanced image data acquired by a clinical imaging modality are superposed.

54. The diagnostic system of claim 3, wherein the visualizing means comprises means for producing image data indicative of a shape of a ventricle of the heart, means for superposing at least one of the first and second information on the image data of the vernacular shape, and means for representing at a time the superposed data and a tomographic image data acquired by a clinical imaging modality.

55. The diagnostic system of claim 1, further comprising measuring means for measuring the magnetic field from a measuring point on a body surface of the patient, wherein the analyzing means comprising expressing means for expressing with a plurality of parameters information about the electrophysiological phenomena including the characteristic quantity, calculating means for calculating a temporal waveform of the magnetic field at each measuring point on the basis of the electrophysiological phenomena expressed with the plurality of parameters, and inferring means for inferably determining each value of the plurality of parameters by searching different values assigned to the plurality of parameters such that a difference between the calculated temporal waveform and information about the measured magnetic field is made small.

56. The diagnostic system of claim 55, wherein the measuring means is a multi-channel type SQUID flux meter measuring the magnetic field.

57. The diagnostic system of claim 55, wherein the electrophysiological phenomena includes not only the characteristic quantity but also a further characteristic quantity associated with a temporal sequence of excitation of the cardiac muscle, and visualizing means is composed of means for displaying not only the characteristic quantity as the distribution image but also the further characteristic quantity as a further distribution image.

58. The diagnostic system of claim 57, wherein the further characteristic quantity associated with the temporal sequence of excitation of the cardiac muscle is an excitation onset time as part of a propagated excitation process of the cardiac muscle.

59. The diagnostic system of claim 58, wherein the analyzing means further comprises model setting means for setting a heart model from image information of the patient.

60. The diagnostic system of claim 59, wherein the expressing means consist of means for expressing both a first distribution of the excitation onset time and a second distribution of an amount of the myocardial electroaction with the parameters in number less than representative points of the heart model, and the analyzing means comprises means for computing the first and second distributions using the less parameters.

61. The diagnostic system of claim 59, wherein the expressing means consist of means for expressing the excitation onset time at each representative point of the heart model, a first distribution of the excitation onset time expressed with an amount of the myocardial electroaction, and a second distribution of the amount of the myocardial electroaction with a linear function according to the parameters in number less than the representative points of the heart model, and the analyzing means comprises means for computing the first and second distributions using the less parameters expressed with the linear functions.

62. The diagnostic system of claim 61, wherein the functions are functions based on either one of a Fourier transform and an inverse Fourier transform.

63. The diagnostic system of claim 62, wherein the linear functions are functions based on matrixes.

64. The diagnostic system of claim 59, wherein the model setting means consist of means setting the heart model by combining a plurality of polyhedrons into a shape of a ventricle.

65. The diagnostic system of claim 64, wherein the polyhedrons are any of hexahedrons, pentahedrons, tetrahedrons, and polyhedrons made by combining thereof.

66. The diagnostic system of claim 59, further comprising image transferring means for receiving three-dimensional image data acquired by a separate clinical imaging modality as well as transferring the received three-dimensional image data to the model setting means as the image information.

67. The diagnostic system of claim 59, wherein the model setting means consist of means setting the heart model with regard to a position, direction, and shape of a ventricle thereof by performing at least either one of movement, rotation, deformation of a predetermined ventricular model and fitting of a surface of the predetermined ventricular model thus-performed with the image information using a non-linear optimization approach.

68. The diagnostic system of claim 67, wherein the model setting means comprise means for superposedly displaying both the imaging information and the heart model.

69. The diagnostic system of claim 58, wherein the visualizing means comprises means for displaying not only a first distribution of the excitation onset time with an isochrone chart but also a second distribution of an amount of the myocardial electroaction with either one of densities in color and differences in hues.

70. The diagnostic system of claim 69, wherein the displaying means is means that superposedly displays the first and second distributions.

71. The diagnostic system of claim 55, wherein the inferring means includes means for calculating an object function by linear optimization with at least one of the parameters to be optimized.

72. The diagnostic system of claim 55, wherein the inferring means includes means for avoiding an undesirable combination of the difference and the value of the parameter by using a penalty function.

* * * * *